(12) United States Patent
Barth et al.

(10) Patent No.: US 10,414,739 B2
(45) Date of Patent: Sep. 17, 2019

(54) COMPOUNDS AS INHIBITORS OF THE YAP/TAZ-TEAD INTERACTION AND THEIR USE IN THE TREATMENT OF MALIGNANT MESOTHELIOMA

(71) Applicant: INVENTIVA, Daix (FR)

(72) Inventors: Martine Barth, Asnieres les Dijon (FR); Sylvie Contal, Talant (FR); Christian Montalbetti, Hauteville les Dijon (FR); Luc Spitzer, Marcilly sur Tille (FR)

(73) Assignee: INVENTIVA, Daix (FR)

( * ) Notice: Subject to any disclaimer, the term of this patent is extended or adjusted under 35 U.S.C. 154(b) by 0 days.

(21) Appl. No.: 15/767,156

(22) PCT Filed: Oct. 14, 2016

(86) PCT No.: PCT/EP2016/074760
§ 371 (c)(1),
(2) Date: Apr. 10, 2018

(87) PCT Pub. No.: WO2017/064277
PCT Pub. Date: Apr. 20, 2017

(65) Prior Publication Data
US 2018/0297964 A1 Oct. 18, 2018

(30) Foreign Application Priority Data

Oct. 15, 2015 (EP) .................................... 15306651

(51) Int. Cl.
| | | |
|---|---|---|
| *C07D 275/06* | (2006.01) | |
| *A61K 31/428* | (2006.01) | |
| *C07D 417/12* | (2006.01) | |
| *A61P 35/00* | (2006.01) | |

(52) U.S. Cl.
CPC ............ *C07D 275/06* (2013.01); *A61P 35/00* (2018.01); *C07D 417/12* (2013.01)

(58) Field of Classification Search
CPC ............................ C07D 275/06; A61K 31/428
See application file for complete search history.

(56) References Cited

FOREIGN PATENT DOCUMENTS

| WO | 2004/087153 | 10/2004 |
|---|---|---|
| WO | 2013/123071 | 8/2013 |

OTHER PUBLICATIONS

CA Reg No. 353483-50-8, entered into Registry Aug. 29, 2001 (Year: 2001).*
Database Registry Chemical Abstracts Service, Dec. 28, 2000, XP002764557.
B. Zhao et al., "TEAD mediates YAP-dependent gene induction and growth control", Genes & Development, vol. 22, No. 14, Jul. 15, 2009, pp. 1962-1971, XP055096567.
M. Santucci et al., "The Hippo Pathway and . . . Cancer Treatment", Journal of Medicinal Chemistry, vol. 58, No. 12, Jun. 25, 2015, pp. 4857-4873, XP055322040.

* cited by examiner

*Primary Examiner* — Karen Cheng
(74) *Attorney, Agent, or Firm* — Clark & Brody

(57) ABSTRACT

The invention relates to compounds of formula (I):

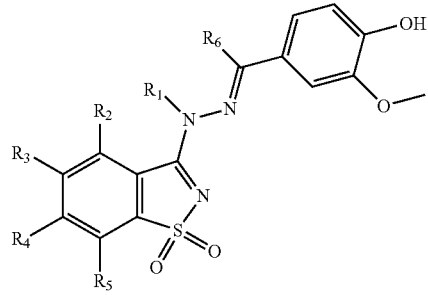

wherein $R_1$, $R_2$, $R_3$, $R_4$, $R_5$ and $R_6$ are as defined in the description.
The compounds of formula (I) are inhibitors of the YAP/TAZ-TEAD interaction.

18 Claims, 1 Drawing Sheet

COMPOUNDS AS INHIBITORS OF THE YAP/TAZ-TEAD INTERACTION AND THEIR USE IN THE TREATMENT OF MALIGNANT MESOTHELIOMA

FIELD OF THE INVENTION

The present invention concerns new compounds inhibitors of the YAP/TAZ-TEAD interaction, and their use in therapy, particularly in the treatment of malignant mesothelioma.

The hippo pathway regulates cell proliferation, cell death and cell differentiation in multicellular organisms to ensure normal tissue development (Tumaneng K et al., Curr Biol, 2013, 22, R368-379; Yu Fx et al., Genes Dev 2013, 27, 355-371). Over the past years, various genetic and biochemical studies in *Drosophila* and mammals have defined a highly conserved core hippo signaling module (Huang et al., Cell 2005, 122, 421-434; Zeng et al, Cancer Cell 208, 13, 188-192; Badouel et al., Curr Opin Cell Biol 2009, 21, 837-843).

Essentially, the core hippo signaling module is composed of members of Ste20-like kinase, (MST1/2) and a large tumor suppressor 1/2 (LATS1/2), together with MOB activator 1A (MOBIA) and MOB1B and the AGC (protein kinase A(PKA)/PKG/PKC-like) kinase families (Hong W et al., Cell Dev Biol 2012, 23, 785-793).

Lats1 and 2, AGC kinases (homologous to *Drosophila* Warts), are activated by association with Mob1 (Mps one binder kinase activator-like 1A and 1B) (Mats in *Drosophila*) and also by phosphorylation by the STE20 family protein kinases MST1 and 2 (Hippo in *Drosophila*).

The final output of hippo signaling is the inhibition of the transcriptional co-activators YAP (Yes-associated protein; Yorkie in *drosophila*)/TAZ (transcriptional co-activator with PDZ-binding motif) by phosphorylation by the complex Lats/Mob, in flies and mammals (Hong W et al., Cell Dev Biol 2012, 23, 785-793; Zhao et al., Cancer Res 2009, 69, 1089-98; Lei et al., Mol Cell Biol 2008, 28, 2426-2436).

Functionally, when the hippo pathway is activated, YAP and TAZ are sequestered in the cytoplasm and degraded. Conversely, when the Hippo pathway is deactivated, YAP and TAZ translocate into the nucleus and promote transcription of downstream genes by forming complexes with transcription factors, such as transcriptional enhancer factors (TEF; also referred to as TEAD) and others. TEADs seems to be the key mediators of the growth and the tumorigenic potential of YAPITAZ. (Zhao et al., Gens Dev 2008, 22, 1962-1971; Harvey et al., Nat Rev Cancer, 2013, 13, 246-257) by inducing the expression of target genes, such as CTGF, Cyr61, FGF1 (Wang L et al., Tumour Biol 2014, 14, 463-468).

Hyperactivation of YAP and TAZ subsequent to a deregulation of the hippo pathway is widespread in cancer, indeed, the levels and nuclear localization of YAP/TAZ are elevated in many tumors such as lung, thyroid, skin, ovarian, colorectal, prostate, pancreas, esophagus, liver and breast cancer (Harvey et al., Nat Rev Cancer 2013, 13, 246-257; Avruch et al., Cell Cycle 2012, 1090-1096; De Christofaro T, Eur J Cancer 2011, 926-933; Zhou et al., Oncogene 2011, 30, 2181-2186; Wang et al., Cancer Sci 2010, 101, 1279-85; Chad et al., Cancer Res 2010, 70, 8517-25; Steinhardt et al., Hum. Pathol 2008, 39, 1582-9, Zhao et al. Genes Dev 2007, 21: 2747-2761; Dong et al. Cell, 2007, 130: 1120-1133 Steinhardt et al., Hum Pathol 2008, 39, 1582-1589).

Although hippo signaling is clearly altered in human cancer, only few germline and somatic mutation of hippo signaling components have been described so far, this is especially true of the core hippo pathway genes. Only neurofibromin 2 (NF2 or merlin in *Drosophila*) an upstream component of the hippo pathway core component has been linked to a heritable cancer syndrome and classified as a tumor suppressor gene. Hundreds of somatically acquired mutation have been reported in NF2, predominantly in meningiomas, mesotheliomas and peripheral nerve sheath tumors, but also in other cancer types. (Harvey et al., Nat Rev Cancer 2013, 13, 246-257; Bianchi et al., Nat Genet 1994, 6, 185-192; Ruttledge et al., Nat Genet 1994, 6, 180-184).

Malignant pleural mesothelioma (MPM) is an aggressive human malignancy, mostly associated with asbestos exposure (Carbone et al., Clin Cancer Res 2012, 18, 598-604). About 3 out of 4 mesotheliomas are pleural mesotheliomas. MPM is a rare disease with a 15-year cumulative frequency during 1994-2008 in the 56 countries reporting MPM to be 174300 cases (Park et al., Environ Health Perspect 2011, 119, 514-518). However the real incidence of MPM is unknown, since there are countries for which MPM mortality is not reported, including asbestos producers. Despite treatment with chemotherapy, radiation therapy or surgery, the prognosis is poor, the median survival time of patients after diagnosis is only 7-12 months. (Bianchi et al. Natl Acad. Sci. USA, 1995, 92, 10854-10858; Sekido et al., Cancer Res 1995, 55, 1227; Deguen et al., Int J Cancer 1998, 77, 554-560).

Malignant pleural mesothelioma shows frequent inactivation of the NF2-tumor suppressor gene, indeed data mining of the catalogue of somatic mutations in cancers shows that the genes that are mostly mutated in MPM are cyclindependant kinase activator (CDKN2A), neurofibromatosis type 2 and BRCA-associated protein 1 (BAP1) (Forbe et al., Nucleic Acids Res 2011, 39, D945-950).

Recently, besides the NF2 mutation, genetic alterations in the components of the hippo signaling pathway have also been identified, including inactivating mutations of Lats1/2 and amplification of YAP. Together with NF2 mutation, MPM shows frequent Merlin-Hippo pathway inactivation, which leads to YAP activation over 70% of MPM cases (Bott et al., Nat Genet 2011, 43, 668-672; Murakami et al., Cancer Res 2011, 71, 873-883; Yokoyama et al., Carcinogenesis 2008, 29, 2139-2146; Sekido et al., Pathol int 2011, 61, 331-344).

Inhibition of the activity of Hippo pathway effectors YAP and TAZ is likely to represent a valuable approach for the treatment of several cancers since the Hippo pathway deregulation is largely observed in many cancers, leading to YAP/TAZ nuclear translocation.

Therefore disruption of hippo pathway downstream YAPITAZ-TEAD interaction is believed to abrogate the oncogenic property of YAP/TAZ. The compounds of invention are designed to block this interaction upon binding to TEAD and can be further developed into drugs for cancers especially for the treatment of malignant mesothelioma.

WO 2004/087153 and WO 2013/123071 disclose hundreds of small molecules susceptible to be used generally in relation with cancer treatments. Two hydrozobenzothiazole derivatives, different from the one disclosed in the present application, are disclosed but no YAP/TAZ-TEAD interaction inhibiting activity is reported, not to mention specific anticancer activity.

The invention provides new compounds identified as inhibitors of the YAP/TAZ-TEAD interaction, and particularly new hydrozobenzothiazole derivatives inhibiting YAP/TAZ-TEAD interaction.

GENERAL DISCLOSURE OF THE INVENTION

The present invention concerns a compound of formula (I), inhibitor of the YAP/TAZ-TEAD interaction,

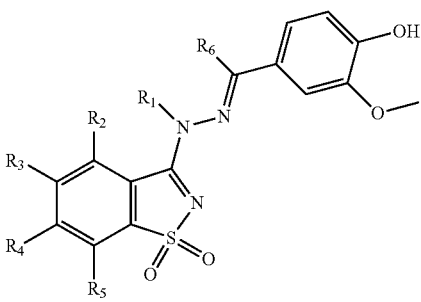

(I)

wherein:

$R_1$ is H, alkyl or alkyl-$R_7$ or -aryl-$R_7$;

$R_2$, $R_3$, $R_4$, $R_5$ are independently H, halo, —B(O—$R_{11}$)$_2$, alkyl, alkoxyl, hydroxycarbonyl, —COO$R_{11}$, —CO—N$R_8R_9$ or aryl;

$R_6$ is H or alkyl; or $R_1$ and $R_6$ are bound together to form a 5 or 6-member heterocycle;

$R_7$ is hydroxyl, alkylhydroxyl, —N$R_8R_9$, —CO—X—$R_{10}$, —CN, —CF$_3$, aryl;

$R_8$ and $R_9$ are independently H, alkyl or form together with the nitrogen atom a 3 to 6-member cyclic group;

X is —O— or —N$R_{11}$—;

$R_{10}$ is H, alkyl or hydroxyalkyl;

$R_{11}$ is H or alkyl;

and pharmaceutically acceptable salts thereof.

The invention particularly concerns a compound of formula (I) and pharmaceutically acceptable salts thereof, wherein at least one of $R_3$, $R_4$ and $R_5$ is not a hydrogen.

The invention also concerns a pharmaceutical composition comprising a compound of formula (I) or one of its pharmaceutically acceptable salts and at least one pharmaceutically acceptable vehicle.

The compounds of formula (i) described herein and their pharmaceutically acceptable salts are representatives of a new class of compounds identified as inhibitors of the YAP/TAZ-TEAD interaction. Therefore, the present invention also concerns the inhibitors of the YAP/TAZ-TEAD interaction, and among them the compounds of formula (I) as described herein, for their use in therapy, particularly in the treatment of any cancer indication where YAP is localized in the nucleus of the tumor cells, such as lung, thyroid, ovarian, colorectal, prostate, pancreas, esophagus, liver, breast and skin cancer, more particularly in the treatment of malignant mesothelioma.

BRIEF DISCLOSURE OF THE FIGURES

DETAILED DISCLOSURE OF THE INVENTION

Figure 1:
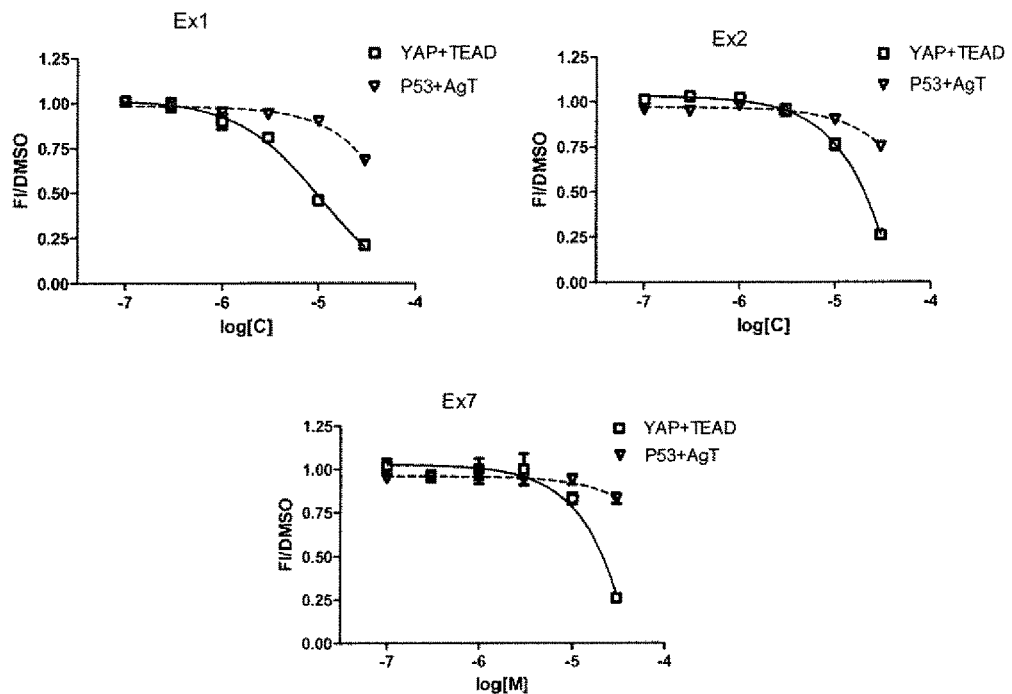
FIG. 1 represents the transactivation activity of compounds of examples 1, 2 and 7 as compounds representatives of the inhibitor of the YAP/TAZ-TEAD interaction of the invention in co-transfected HEK293 cells.

According to the present invention, an inhibitor of the YAP/TAZ-TEAD interaction is a small molecule having a molecular weight of less than 1000 daltons, preferably less than 900 daltons, and generally between 300 and 600 daltons, having the ability to bind to TEAD to inhibit the interaction between YAP/TAZ and TEAD. More particularly, the small molecule inhibits the interaction between YAP/TAZ and TEAD by binding to TEAD.

These inhibitors can be identified in screening small molecules in biological assays, such as an alpha screen assay (ASA) and/or a transactivation assay (TA) as described below. More preferably, the inhibitor of the YAP/TAZ-TEAD interaction is a small molecule showing activity in both the alpha-screen and the transactivation assays (ASA and TA). The skilled person knows how to obtain small molecules for screening and how to screen and select the molecules showing an activity in these biological tests. Once a small molecule is selected, with a known chemical structure, the person skilled in the art knows how to prepare new molecules of the same structure using his usual knowledge of chemical synthesis.

The compounds of formula (I) described herein and their pharmaceutically acceptable salts are representatives of this new class of compounds.

According to the present invention, the term "alkyl" of the prefix "alk" means a linear or branched $C_1$-$C_6$ alkyl moiety, particularly a $C_1$-$C_4$ alkyl moiety, more particularly $C_1$, $C_2$, $C_3$ or $C_4$ alkyl moieties, including the groups methyl or methylene, ethyl or ethylene, propyl or propylene, isopropyl or isopropylene, butyl or butylene, isobutyl or isobutylene and tertiobutyl or tertiobutylene. In particular embodiments, the alkyl moieties are selected among methyl or methylene, ethyl or ethylene, propyl or propylene.

According to the present invention, the "halo" group is selected among F, Cl, Br or I, particularly F or Cl, more particularly F.

According to the present invention, "aryl" means an aromatic (hetero)cycle comprising 1 or 2 rings, including phenyl, naphthyl, pyrazolyl, pyridyl, indolyl, thienyl, and derivatives thereof. The aryl derivatives are aryls substituted by one or more substituent selected among alkyl and halo groups.

According to the invention, pharmaceutically acceptable salts are salts of acids or bases, known for their use in the preparation of active principles for their use in therapy. Examples of pharmaceutically acceptable acids suitable as source of anions are those disclosed in the *Handbook of Pharmaceutical Salts: Properties, Selection and Use* (P. H. Stahl and C. G. Wermuth, Weinheim/Zürich:Wiley-VCHN-HCA, 200).

$R_1$ is particularly selected among methyl, ethyl, n-propyl, hydroxyethyl, hydroxyl-n-propyl, morpholinoethyl, morpholino-n-propyl, methoxyethyl, methoxypropyll dimethylamino-n-propyl, $CH_2COOH$, $CH_2CH_2COOH$ and $CH_2CONHCH_2CH_2OH$.

When $R_8$ and $R_9$ together with the nitrogen atom a 3 to 6-member cyclic group, including 3, 4, 5 or 6-member cycles, it is preferably selected among the group consisting of aziridinyl, azetidinyl, diazetidinyl, pyrrolidinyl, pyrrolinyl, pyrrolyl, imidazolidinyl, imidazolyl, pyrazolidinyl, pyrazolyl, piperidinyl, piperazinyl, pyrazinyl, triazinyl, morphonlinyl, oxazinyl, thiomorpholinyl, thiazinyl. A preferred cyclic group is morpholinyl. The 3 to 6-member cyclic group may be substituted by one or more groups selected among alkyl, and halo.

When $R_1$ and $R_6$ are bound together to form a 5 or 6-member heterocycle, they particularly represent an alkylene moiety selected among —C$R_{12}R_{13}$ and —C$R_{12}$—C$R_{13}$— wherein $R_{12}$ and $R_{13}$ are independently H, alkyl, alkyl-$R_7$ or -aryl-$R_7$. In a particular embodiment, $R_{12}$ and $R_{13}$ are H. In another embodiment, at least one of $R_{12}$ and $R_{13}$ is H and the other is an alkyl group, particularly $R_{12}$ is an alkyl group and $R_{13}$ is H.

According to an embodiment of the present invention the compound of formula (I) is a compound of formula (I'):

(I')

wherein:
$R_a$ is H, alkyl or $R_f$-alkyl;
$R_b$, $R_c$, $R_d$, $R_e$ are independently H, halo, alkyl, alkoxyl, or hydroxycarbonyl;
$R_f$ is hydroxyl, alkylhydroxyl, —$NR_gR_h$ or —CO—X—$R_i$;
$R_g$ and $R_h$ are independently H, alkyl or form together with the nitrogen atom a morpholino group;
X is —O— or —$NR_j$—;
$R_i$ is H, alkyl or hydroxyalkyl;
$R_j$ is H or alkyl;
or a pharmaceutically acceptable salt thereof.

According to an embodiment of the invention, $R_2$, $R_3$, $R_4$ and $R_5$ are H. The compound of formula (I) is particularly selected among:

4-[(E)-[(1,1-dioxo-1,2-benzothiazol-3-yl)-methyl-hydrazono]methyl]-2-methoxy-phenol 4-[(E)-[(1,1-dioxo-1,2-benzothiazol-3-yl)-(2-hydroxyethyl) hydrazono]methyl]-2-methoxy-phenol 4-[(E)-[(1,1-dioxo-1,2-benzothiazol-3-yl)-ethyl-hydrazono]methyl]-2-methoxy-phenol 4-[(E)-[(1,1-dioxo-1,2-benzothiazol-3-yl)-(2-morpholinoethyl)hydrazono]methyl]-2-methoxy-phenol hydrochloride 4-[(E)-[(1,1-dioxo-1,2-benzothiazol-3-yl)-(3-hydroxypropyl)hydrazono]methyl]-2-methoxy-phenol 4-[(E)-[3-(dimethylamino)propyl-(1,1-dioxo-1,2-benzothiazol-3-yl)hydrazono]methyl]-2-methoxy-phenol hydrochloride 4-[(E)-[(1,1-dioxo-1,2-benzothiazol-3-yl)-(2-methoxyethyl)hydrazono]methyl]-2-methoxy-phenol 3-[(1,1-dioxo-1,2-benzothiazol-3-yl)-[(E)-(4-hydroxy-3-methoxy-phenyl)methylene amino]amino]propanoic acid 2-[(1,1-dioxo-1,2-benzothiazol-3-yl)-[(E)-(4-hydroxy-3-methoxy-phenyl)methylene amino]amino]-N-(2-hydroxyethyl)acetamide 4-[(E)-[(1,1-dioxo-1,2-benzothiazol-3-yl)-(3-methoxypropyl)hydrazono]methyl]-2-methoxy-phenol 4-[(E)-[(1,1-dioxo-1,2-benzothiazol-3-yl)-isopropyl-hydrazono]methyl]-2-methoxy-phenol 4-[(E)-[(1,1-dioxo-1,2-benzothiazol-3-yl)-(2,2,2-trifluoroethyl)hydrazono]methyl]-2-methoxy-phenol 4-[(1,1-dioxo-1,2-benzothiazol-3-yl)-[(E)-(4-hydroxy-3-methoxy-phenyl) methyleneamino]amino]benzoic acid and pharmaceutically acceptable salts thereof.

According to an embodiment of the invention, $R_3$ is halo, alkyl, alkoxyl, or hydroxycarbonyl. Particularly $R_3$ is halo, alkyl, alkoxyl, or hydroxycarbonyl and $R_2$, $R_4$ and $R_5$ are H. Particularly $R_3$ is selected among methyl, methoxyl and F.

The compound of formula (I) is particularly selected among:

4-[(E)-[2-hydroxyethyl-(5-methoxy-1,1-dioxo-1,2-benzothiazol-3-yl)hydrazono]methyl]-2-methoxy-phenol 2-methoxy-4-[(E)-[(5-methoxy-1,1-dioxo-1,2-benzothiazol-3-yl)-(2-morpholinoethyl) hydrazono]methyl]phenol 2-methoxy-4-[(E)-[(5-methoxy-1,1-dioxo-1,2-benzothiazol-3-yl)-(3-morpholino propyl)hydrazono]methyl]phenol hydrochloride 4-[(E)-[3-hydroxypropyl-(5-methoxy-1,1-dioxo-1,2-benzothiazol-3-yl)hydrazono]methyl]-2-methoxy-phenol 2-methoxy-4-[(E)-[(5-methoxy-1,1-dioxo-1,2-benzothiazol-3-yl)-(2-methoxyethyl) hydrazono]methyl]phenol 2-methoxy-4-[(E)-[methyl-(5-methyl-1,1-dioxo-1,2-benzothiazol-3-yl)hydrazono]methyl]phenol 2-methoxy-4-[(E)-[(5-methyl-1,1-dioxo-1,2-benzothiazol-3-yl)-(2-morpholinoethyl) hydrazono]methyl]phenol hydrochloride 4-[(E)-[2-hydroxyethyl-(5-methyl-1,1-dioxo-1,2-benzothiazol-3-yl)hydrazono]methyl]-2-methoxy-phenol 2-methoxy-4-[(E)-[2-methoxyethyl-(5-methyl-1,1-dioxo-1,2-benzothiazol-3-yl) hydrazono]methyl]phenol 2-methoxy-4-[(E)-[(5-methoxy-1,1-dioxo-1,2-benzothiazol-3-yl)-methyl-hydrazono]methyl]phenol 4-[(E)-[(5-fluoro-1,1-dioxo-1,2-benzothiazol-3-yl)-methyl-hydrazono]methyl]-2-methoxy-phenol and pharmaceutically acceptable salts thereof.

According to another embodiment of the invention, $R_4$ is halo, alkyl, alkoxyl, or hydroxycarbonyl. Particularly $R_4$ is halo, alkyl, alkoxyl, or hydroxycarbonyl and $R_2$, $R_3$ and $R_5$ are H. Particularly $R_4$ is selected among methyl, F, methoxy and hydroxycarbonyl.

The compound of formula (I) is particularly selected among:

2-methoxy-4-[(E)-[methyl-(6-methyl-1,1-dioxo-1,2-benzothiazol-3-yl)hydrazono]methyl]phenol 3-[[[(E)-(4-hydroxy-3-methoxy-phenyl)methyleneamino]-methyl-amino]-1,1-dioxo-1,2-benzothiazole-6-carboxylic acid 2-methoxy-4-[(E)-[(6-methoxy-1,1-dioxo-1,2-benzothiazol-3-yl)-methyl hydrazono]methyl]phenol 4-[(E)-[(6-fluoro-1,1-dioxo-1,2-benzothiazol-3-yl)-methyl-hydrazono]methyl]-2-methoxy-phenol and pharmaceutically acceptable salts thereof.

According to another embodiment of the invention, $R_5$ is halo, alkyl, alkoxyl, or hydroxycarbonyl. Particularly $R_5$ is halo, alkyl, alkoxyl, or hydroxycarbonyl and $R_2$, $R_3$ and $R_4$ are H. Particularly $R_5$ is selected among methyl and methoxyl.

The compound of formula (I) is particularly selected among:

2-methoxy-4-[(E)-[(7-methoxy-1,1-dioxo-1,2-benzothiazol-3-yl)-methyl-hydrazono]methyl]phenol 4-[(E)-[2-hydroxyethyl-(7-methoxy-1,1-dioxo-1,2-benzothiazol-3-yl)hydrazono]methyl]-2-methoxy-phenol 2-methoxy-4-[(E)-[(7-methoxy-1,1-dioxo-1,2-benzothiazol-3-yl)-(2-morpholinoethyl) hydrazono]methyl]phenol hydrochloride 2-methoxy-4-[(E)-[(7-methoxy-1,1-dioxo-1,2-benzothiazol-3-yl)-(2-methoxyethyl) hydrazono]methyl]phenol and pharmaceutically acceptable salts thereof.

In another embodiment, both $R_3$ and $R_5$ independently are halo, alkyl, alkoxyl, or hydroxycarbonyl and $R_2$ and $R_4$ are H.

The compound of formula (I) is particularly selected among

4-[(E)-[(5,7-dimethoxy-1,1-dioxo-1,2-benzothiazol-3-yl)-methyl-hydrazono]methyl]-2-methoxy-phenol 4-[(E)-[(5,7-dimethoxy-1,1-dioxo-1,2-benzothiazol-3-yl)-(2-hydroxyethyl)hydrazono]methyl]-2-methoxy-phenol 4-[(E)-[(5,7-dimethoxy-1,1-dioxo-1,2-benzothiazol-3-yl)-(2-morpholinoethyl) hydrazono]methyl]-2-methoxy-phenol hydrochloride 4-[(E)-[(5,7-dimethoxy-1,1-dioxo-1,2-benzothiazol-3-yl)-(2-methoxyethyl)hydrazono]methyl]-2-methoxy-phenol 4-[(E)-[(5-fluoro-7-methyl-1,1-dioxo-1,2-benzothiazol-3-yl)-methyl-hydrazono]methyl]-2-methoxy-phenol 4-[(E)-[2-hydroxyethyl-(7-methoxy-5-methyl-1,1-dioxo-1,2-benzothiazol-3-yl) hydrazono]methyl]-2-methoxy-phenol 2-methoxy-4-[(E)-[2-methoxyethyl-(7-methoxy-5-methyl-1,1-dioxo-1,2-benzothiazol-3-yl)hydrazono]methyl]phenol 2-methoxy-4-[(E)-[(7-methoxy-5-methyl-1,1-dioxo-1,2-benzothiazol-3-yl)-methyl-hydrazono]methyl]phenol 2-methoxy-4-[(E)-[(7-methoxy-5-methyl-1,1-dioxo-1,2-benzothiazol-3-yl)-(2-morpholinoethyl)hydrazono]methyl]phenol hydrochloride and pharmaceutically acceptable salts thereof.

The present invention also concerns a pharmaceutical composition comprising at least one compound of formula (I) or one of its pharmaceutically acceptable salts as the active principle. Pharmaceutical compositions and method for their preparation are well known in the art. Particularly, the composition comprises at least the compound of general formula (I) or one of its pharmaceutically acceptable salts as the active principle and at least one pharmaceutically acceptable excipient.

The pharmaceutical composition of the invention is formulated for its administration by usual routes particularly to be administered by oral, sublingual, subcutaneous, intramuscular, intravenous, transdermal, local or rectal route. The form of the pharmaceutical composition is particularly chosen among the group consisting of tablets, capsules, powders, granules and oral solutions or suspensions, sublingual forms of administration, subcutaneous, topical, intramuscular, intravenous, intranasal or intraocular forms of administration and rectal forms of administration.

Such forms, excipients and methods for their preparation are well known in the art, such as described (Handbook of pharmaceutical Excipients, Rowe et al, seventh edition, June 2012; Rules and Guidance For Pharma Manufacturers and distributors 205, Medicines and Healthcare products Regulatory Agency, London UK)

Therefore, the present invention also concerns the inhibitors of the YAP/TAZ-TEAD interaction, and among them the compounds of formula I as described herein, for their use in therapy, particularly in the treatment of any cancer indication where YAP is localized in the nucleus of the tumor cells, such as lung, thyroid, ovarian, colorectal, prostate, pancreas, esophagus, liver, breast and skin cancer, more particularly in the treatment of malignant mesothelioma.

The invention also concerns a method for treating cancer in a patient in need thereof, comprising administering an appropriate dose of an inhibitor of the YAP/TAZ-TEAD interaction, and particularly the compounds of formula (I) as described herein, wherein the cancer is any cancer indication where YAP is localized in the nucleus of the tumor cells, such as lung, thyroid, ovarian, colorectal, prostate, pancreas, esophagus, liver, breast and skin cancer, particularly malignant mesothelioma.

The appropriate dose of inhibitors and the administration regimen is determined by the skilled practitioner, depending on the activity of the small molecule and the body weight of the patient. They are generally between 5 mg and 1000 mg per day orally for an adult. In general the doctor will determine the appropriate dosage depending on the age, weight and any other factors specific to the subject to be treated.

In a particular embodiment, the inhibitor of the YAP/TAZ-TEAD interaction, and particularly the compounds of formula I is used together or separately in combination with another treatment of cancer, particularly malignant mesothelioma, such as surgery, chemotherapy (with among other cisplatin, carboplatin, alimta (pemetrexed), gemcitabine and doxorubicin) and radiation.

General Synthetic Schemes

Compounds of the invention may be prepared using the synthetic transformations illustrated in schemes I-V. Starting materials are commercially available or may be prepared by procedures described herein, by literature procedures, or by procedures well known to one skilled in the art of organic chemistry.

In scheme I, step a, commercially available 3-methoxy-4-hydroxy-benzaldehyde in solution in alcohol is reacted with hydrazines and an organic or mineral base (like sodium acetate, triethylamine, sodium hydrogenocarbonate, potassium carbonate . . . ) (for example, Kurian et al. Bioorganic & Medicinal Chemistry Letters, 24(17), 4176-4180; 2014 or Loghmani-Khouzani et al. Journal of Chemical Research, Synopses, (2), 80-81; 2001). Step b, saccharin analogs (commercially available or prepared following schemes III-V) are reacted with thionyl chloride in presence of dimethylformamide or other chlorinating agent such as phosphorous pentachloride, phosphorous oxychloride, oxalyl chloride (for example, Differding et al. Helvetica Chimica Acta, 72(6), 1248-52; 1989, or Raw et al. Tetrahedron Letters, 52(50), 6775-6778; 2011). Step c, 2-methoxy-4-hydrazonomethyl-phenols obtained in step a and 3-chloro-1,2-benzothiazole 1,1-dioxides obtained in step b can react together using or not an organic or mineral base (for example, Haffner et al. Bioorganic & Medicinal Chemistry Letters, 20(23), 6989-6992; 2010 or Haffner et al. Bioorganic & Medicinal Chemistry Letters, 20(23), 6983-6988; 2010) to give 1,1-dioxo-1,2-benzothiazol-3yl hydrazonomethyl-2-methoxy-phenols.

Scheme I

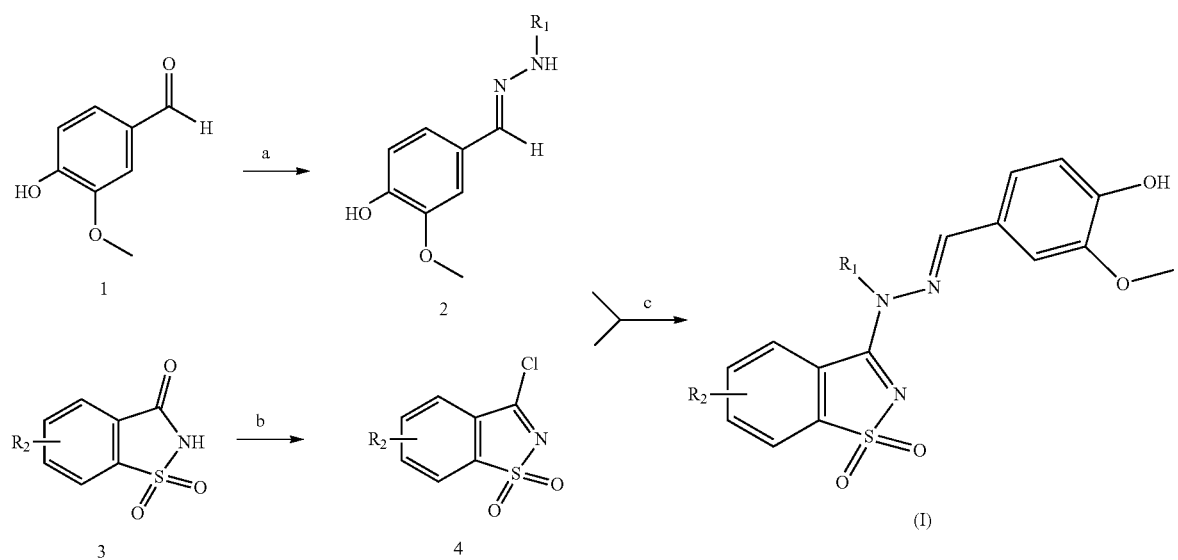

In scheme 2, step a, aromatic substitution of saccharins (commercially available or prepared using transformations described in schemes III-V) with hydrazines may be done in similar conditions as described in scheme i step c. Step b, 1,1-dioxo-1,2-benzothiazol-3-yl-hydrazines obtained in step a are reacted with commercially available 3-methoxy-4-hydroxy-benzaldehyde in similar conditions as described in scheme i, step a.

Scheme II

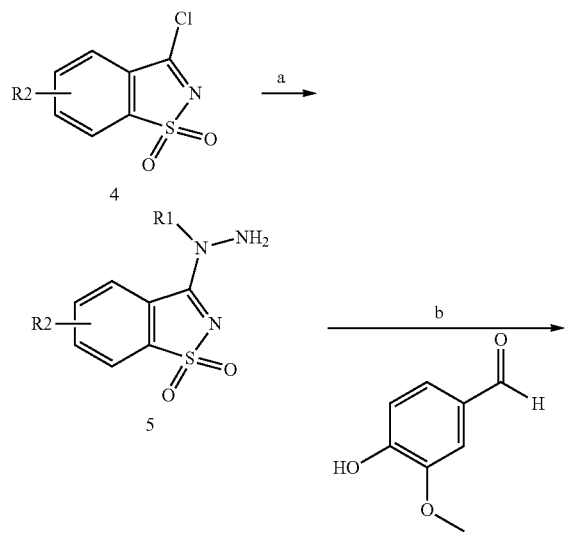

Saccharin derivatives may be prepared by transformations described in schemes III-V. In scheme III, step a, commercially available cumylamine can be sulfonylated with phenylsulfonyl chloride (commercially available or prepared following scheme V) in presence of an organic or mineral base (like triethylamine, pyridine, potassium carbonate) (for example, Blanchet et al. Journal of Organic Chemistry, 72(9), 3199-3206; 2007 or Schneider et al. Organic Letters, 13(14), 3588-3591; 2011). In step b, ortho lithiation of sulfonamide derivatives obtained in step a made using a strong base (like s-BuLi or n-BuLi), followed by acylation with diethylcarbamoyl chloride can give intermediate 11 (for example, Blanchet et al. Journal of Organic Chemistry, 72(9), 3199-3206; 2007). Step c, cleavage of cumyl protective group may be achieved in acidic media like trifluoroacetic acid (for example, Blanchet et al. Journal of Organic Chemistry, 72(9), 3199-3206; 2007 or Perez-Serrano et al. Organic Letters, 1(8), 1183-1186; 1999). Step d, cyclisation towards saccharin can be done in acetic acid at high temperature (for example, Blanchet et al. Journal of Organic Chemistry, 72(9), 3199-3206; 2007 or Ranjit et al. Journal of Organic Chemistry, 59(23), 7161-7163; 1994).

Scheme III

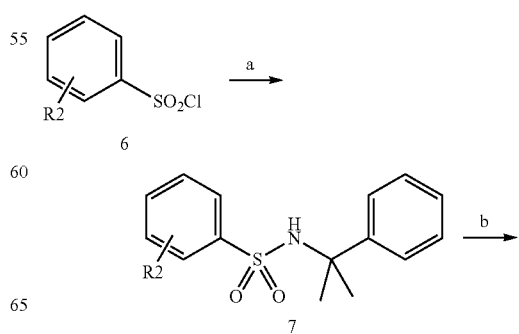

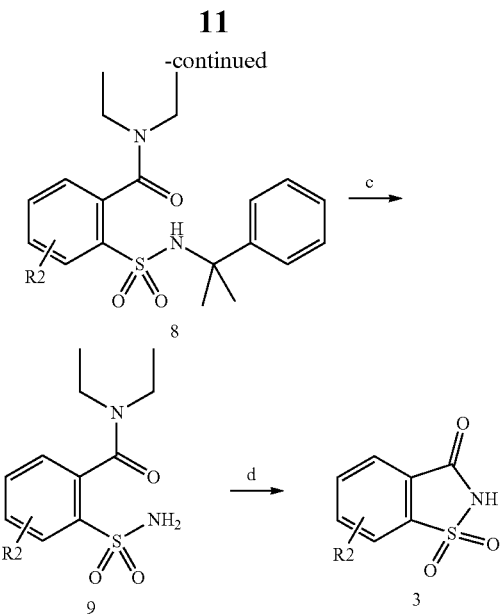

8

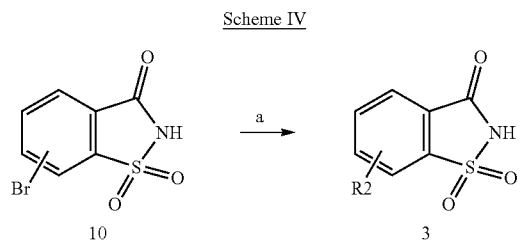

9      3

In scheme IV, step a, R₂ substituent can be introduced by a Suzuki reaction using well described palladium catalysts (for example, Gray et al. Tetrahedron Letters, 41(32), 6237-6240; 2000)

Scheme IV

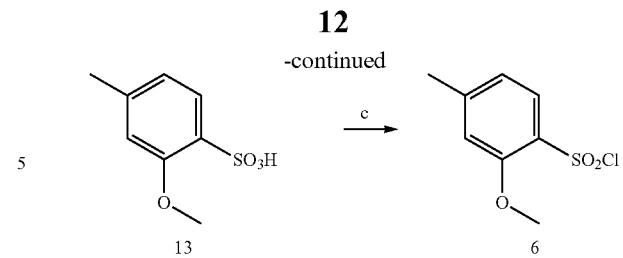

13      6

Abbreviations

Ac Acetyl
AcOH Acetic acid
ACN Acetonitrile
Boc t-Butoxycarbonyl
Boc₂O Di-tert-butyl-dicarbonate
BSA Bivine serum albumin
n-BuLi n-Butyllithium
s-BuLi sec-Butyllithium
t-BuLi tert-Butyllitium
Bu₄NBr Tetrabutylammonium bromide
CaCl₂ Calcium chloride
CDCl₃ Chloroform deutered
Cs₂CO₃ Cesium carbonate
d Doublet
DCE Dichlororethane
DCM Dichloromethane
dd Doublet of doublets
DMF N,N-Dimethylformamide
DMSO Dimethylsulfoxide
dppf 1,1'-bis(diphenylphosphino)ferrocene
eq Equivalent(s)
EtOAc Ethyl acetate
Et₂O Ether
EtOH Ethanol
g Gram(s)
h Hour(s)
HATU O-(7-azabenzotriazol-1-yl)-N,N,N',N'-tetramathyluroniom hexafluorophosphate
HCl Hydrochloric acid
Hz Hertz
HOBt Hydroxybenzotriazole
KF Potassium fluoride
K₂CO₃ Potassium carbonate
LC/MS Liquid chromatography/mass spectrometry
LDA Lithium diisopropylamide
LiAlH₄ Lithium aluminium hydride
LiHMDS Lithium bis(trimethylsilyl)amide
m Multiplet
MeOH Methanol
mg Milligram
MgSO₄ Magnesium sulfate
min Minute(s)
mmol Millimole
mp Melting point
MW Microwave
N Normal
NaCl Sodium chloride
NaH Sodium hydride
NaHCO₃ Sodium bicarbonate
NaBH₃CN Sodium cyanoborohydride
Na₂CO₃ Sodium carbonate
NaOH Sodium hydroxide
Na₂SO₄ Sodium sulfate
NH₃ Ammonia In scheme V, step a, aromatic sulfonylation of commercially 2-bromo-5-methoxytoluene can be done using sulfuric acid by a method known to one skilled in the art (for example, Challenger et al. PCT Int. Appl., 9920323; 29 Apr. 1999). Step b, removal of halogen may be achieved by hydrogenation under pressure using classical catalysts (like palladium, nickel . . . ) (For example, Challenger et al. PCT Int. Appl., 9920323; 29 Apr. 1999 or Courtin et al. Helvetica Chimica Acat, 66(1), 68-75; 1983). Step c, sulfonic acid obtained in step b can be transform to the corresponding sulfonyl chloride analog using thionyl chloride (for example, Thea et al. Journal of Organic Chemistry, 50(12), 2158-2165; 1985).

Scheme V

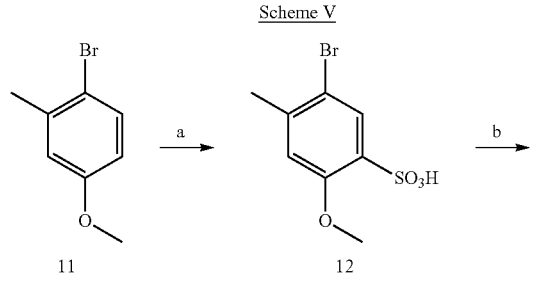

11      12

NH₄Cl Ammonium chloride
NMM N-methylmorpholine
NMR Nuclear magnetic resonance
PBS Phosphate buffered saline
Pd/C Palladium on carbon
PdCl₂(dppf) Dichloro[1,1'-bis(diphenylphosphino)ferrocene] palladium (11)
Pd₂(dba)₃ Bis(dibenzylideneacetone)palladium(0)
Pd(OAc)₂ Palladium (II) acetate
Pd(PPh₃)₄ Tetrakis(triphenylphosphine)palladium (0)
Ph Phenyl
ppm Parts per million
PrOH Propanol
PSI Pounds per square inch
q Quadruplet
quant Quantitative
quint Quintuplet
rt Room temperature
s singlet
t triplet
TBAF Tetrabutylammonium fluoride
TEA Triethylamine
TFA Trifluoroacetic acid
THF Tetrahydrofuran
TMEDA N,N,N',N'-tretramethylethylenediamine General Reagents and solvents obtained from commercial suppliers are used without further purification unless otherwise stated, Analytical data is included within the procedures below. ¹H NMR spectra were recorded on a Bruker Advance spectrometer. Chemical shifts are reported in ppm (3) and were calibrated using the undeuterated solvent resonance as internal standard. Melting points were determined on a hostage apparatus and are uncorrected.

Example 1: 4-[(E)-[(1,1-dioxo-1,2-benzothiazol-3-yl)-methyl-hydrazono]methyl]-2-methoxy-phenol Step A: 3-chloro-1,2-benzothiazole 1,1-dioxide

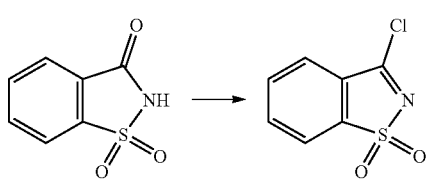 [SMILES: O=C1NS(=O)(=O)c2ccccc21 ; O=S1(=O)N=C(Cl)c2ccccc21]

A mixture of saccharin (4.00 g; 21.84 mmol; 1 eq.), thionyl chloride (2.38 mL; 32.75 mmol; 1.5 eq.) and a catalytic amount of DMF (120 μL) in 1,4-dioxane (20 mL) was heated for 24 h under reflux. The reaction mixture was concentrated and the residue was recrystallized from toluene, filtered, washed by cold toluene and dried under vacuum at 50° C. to give of a broken white solid. The filtrate was concentrated under reduced pressure and was recrystallized from toluene, filtered, washed by cold toluene. The combined solids were washed by cold toluene and dried under vacuum at 50° C. to give 3-chloro-1,2-benzothiazole 1,1-dioxide (3.28 g; 74%). ¹H NMR (DMSO-d₆, 300 MHz): δ 8.19 (dd, J=1 Hz, J=7 Hz, 1H); 7.99 (m, 3H).

Step B: 2-methoxy-4-[(E)-(methylhydrazono)methyl]phenol

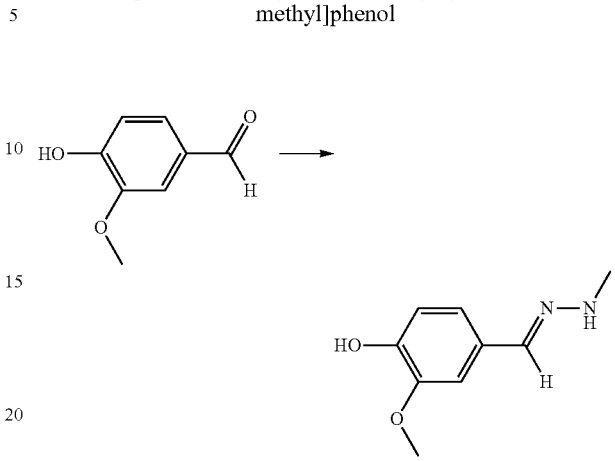

To a solution of 4-hydroxy-3-methoxybenzaldehyde (1.00 g; 6.57 mmol; 1 eq.) in EtOH (25 mL) was added methyl hydrazine (525 μL; 9.86 mmol; 1.5 eq.) and sodium acetate (808.8 mg; 9.86 mmol; 1.50 eq.). The solution was heated at 80° C. under MW irradiation for 5 min. The reaction mixture was concentrated under vacuum. The solid was triturated into water, filtered and washed with water to give after drying at 50° C. 2-methoxy-4-[(E)-(methylhydrazono)methyl]phenol (870.0 mg; 73%) as a beige solid. ¹H NMR (DMSO-d₆, 300 MHz): δ 8.97 (s, 1H); 7.36 (s, 1H); 7.11 (d, J=1.8 Hz, 1H); 6.91 (d, J=4.8 Hz, 1H, NH); 6.84 (dd, J=1.8 Hz, J=8.1 Hz, 1H); 6.70 (d, J=8.1 Hz, 1H); 3.76 (s, 3H); 2.75 (d, J=4.8 Hz, 3H).

Step C: 4-[(E)-[(1,1-dioxo-1,2-benzothiazol-3-yl)-methyl-hydrazono]methyl]-2-methoxy-phenol

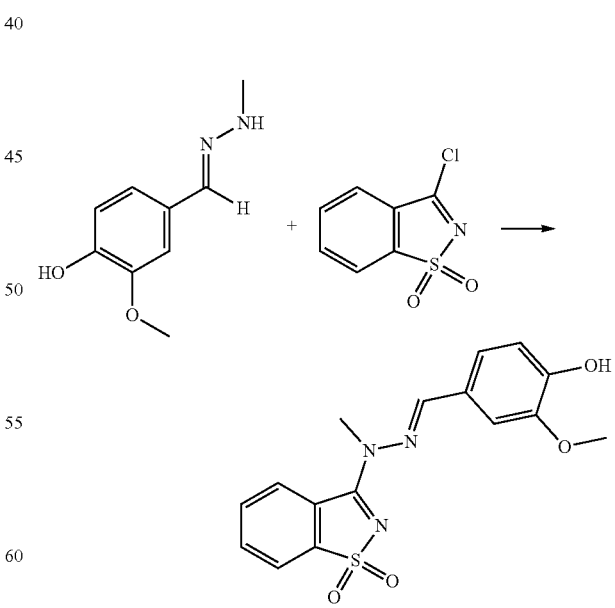

3-chloro-1,2-benzothiazole 1,1-dioxide (813.8 mg; 4.04 mmol; 1 eq.) was dissolved into dry THF (5 mL) and then added dropwise to a solution of 2-methoxy-4-[(E)-(methylhydrazono)methyl]phenol (800.0 mg; 4.44 mmol; 1.10 eq.)

in THF (12 mL). The resulting mixture was stirred under reflux for 1 h30 and then concentrated under vacuum. The solid was triturated into ACN, filtered, washed with ACN and dried, to give 4-[(E)-[(1,1-dioxo-1,2-benzothiazol-3-yl)-methyl-hydrazono]methyl]-2-methoxy-phenol (810.0 mg; 58%) as a yellow powder. ¹H NMR (DMSO-d₆, 400 MHz): δ 9.76 (s, 1H); 8.91 (d, J=7.6 Hz, 1H); 8.37 (s, 1H); 7.90 (m, 2H); 7.42 (s, 1H); 7.34 (d, J=8.4 Hz, 1H); 6.94 (d, J=8.4 Hz, 1H); 3.88 (s, 1H); 3.78 (s, 1H). mp: 218° C.

Example 2: 4-[(E)-[(1,1-dioxo-1,2-benzothiazol-3-yl)-(2-hydroxyethyl)-hydrazono]methyl]-2-methoxy-phenol Step A: 4-[(E)-(2-hydroxyethylhydrazono)methyl]-2-methoxy-phenol

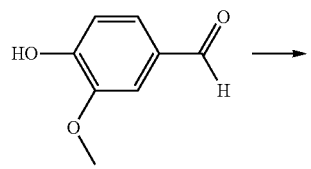

The compound was prepared using the same procedure detailed in example 1 step B starting from 4-hydroxy-3-methoxybenzaldehyde (1.00 g; 6.57 mmol; 1 eq.) and 2-hydroxyethylhydrazine (446 µL; 6.57 mmol; 1 eq.), giving 4-[(E)-(2-hydroxyethylhydrazono)methyl]-2-methoxy-phenol (1.84 g, 89%) as a yellow solid. ¹H NMR (DMSO-de, 300 MHz): δ 7.54 (s, 1H); 7.08 (d, J=1.8 Hz, 1H); 6.82 (dd, J=1.8 Hz, J=8.4 Hz, 1H); 6.74 (d, J=8.4 Hz, 1H); 3.79 (s, 3H); 3.54 (t, J=6 Hz, 2H); 3.13 (m, 2H).

Step B: 4-[(E)-[(1,1-dioxo-1,2-benzothiazol-3-yl)-(2-hydroxyethyl)hydrazono]methyl]-2-methoxy-phenol

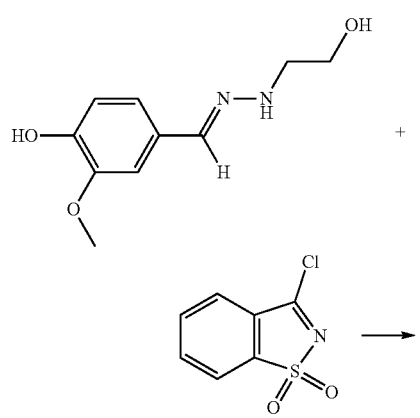

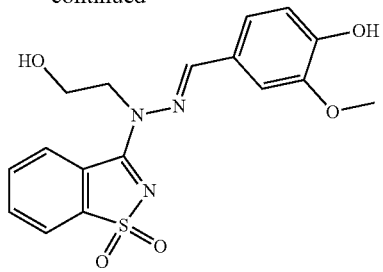

The compound was prepared using the same procedure detailed in example 1 step C starting from 4-[(E)-(2-hydroxyethylhydrazono)methyl]-2-methoxy-phenol (800.0 mg; 3.81 mmol; 1.1 eq.) and 3-chloro-1,2-benzothiazole 1,1-dioxide (Example 1, step A, 697.5 mg; 3.46 mmol; 1 eq.), giving 4-[(E)-[(1,1-dioxo-1,2-benzothiazol-3-yl)-(2-hydroxyethyl) hydrazono]methyl]-2-methoxy-phenol (1.08 g, 83%) as a yellow powder. ¹H NMR (DMSO-d₆, 400 MHz): δ 9.79 (s, 1H); 8.84 (d, J=7.6 Hz, 1H); 8.57 (s, 1H); 8.07 (dd, J=0.8 Hz, J=6.4 Hz, 1H); 7.89 (m, 2H); 7.42 (d, J=1.5 Hz, 1H); 7.31 (dd, J=1.5 Hz, J=8.2 Hz, 1H); 6.95 (d, J=8.2 Hz, 1H); 5.14 (s broad, 1H, OH); 4.42 (t, J=6 Hz, 2H); 3.88 (s, 3H); 3.78 (t, J=6 Hz, 2H). mp: 264° C.

Example 3: 4-[(E)-[(1,1-dioxo-1,2-benzothiazol-3-yl)-ethyl-hydrazono]methyl]-2-methoxy-phenol Step A: 4-[(E)-(ethyl-hydrazono)methyl]-2-methoxy-phenol

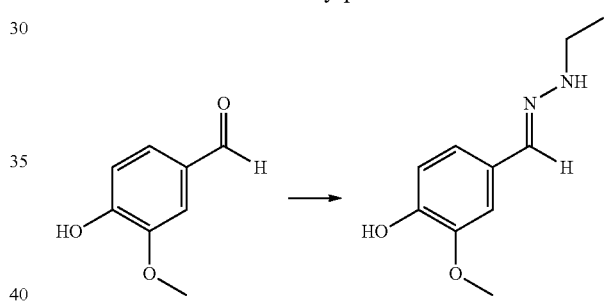

The compound was prepared using the same procedure detailed in example 1 step B starting from 4-hydroxy-3-methoxybenzaldehyde (150.0 mg; 0.99 mmol; 1 eq.) and ethylhydrazine hydrochloride (104.7 mg; 1.08 mmol; 1.1 eq.) giving 4-[(E)-(ethyl-hydrazono)methyl]-2-methoxy-phenol (218.6 mg, 93%) as an orange solid. ¹H NMR (DMSO-d₆, 300 MHz): δ 8.50 (s, 1H); 7.31 (d, J=1.8 Hz, 1H); 7.20 (dd, J=1.8 Hz, J=8.1 Hz, 1H); 6.89 (d, J=8.1 Hz, 1H); 3.81 (s, 3H); 3.26 (d, J=7.2 Hz, 2H); 1.25 (t, J=7.2 Hz, 3H).

Step B: 4-[(E)-[(1,1-dioxo-1,2-benzothiazol-3-yl)-ethyl-hydrazono]methyl]-2-methoxy-phenol

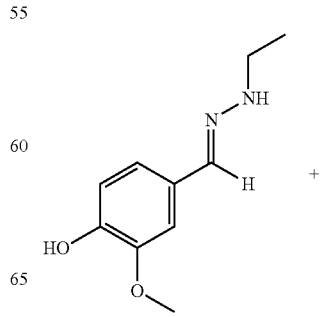

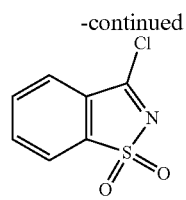

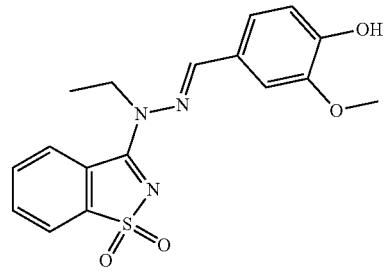

The compound was prepared using the same procedure detailed in example 1 step C starting from 4-[(E)-(ethylhydrazono)methyl]-2-methoxy-phenol (215.0 mg; 1.11 mmol; 1.1 eq.) and 3-chloro-1,2-benzothiazole 1,1-dioxide (Example 1, step A, 202.9 mg; 1.01 mmol; 1 eq.) giving 4-[(E)-[(1,1-dioxo-1,2-benzothiazol-3-yl)-ethyl-hydrazono]methyl]-2-methoxy-phenol (138.5 mg, 38%) as a pale yellow powder. $^1$H NMR (DMSO-$d_6$, 500 MHz): δ 9.80 (s, 1H); 8.86 (d, J=7.5 Hz, 1H); 8.44 (s, 1H); 8.07 (dd, J=0.8 Hz, J=7 Hz, 1H); 7.89 (m, 2H); 7.45 (d, J=2 Hz, 1H); 7.35 (dd, J=2 Hz, J=8.5 Hz, 1H); 6.94 (d, J=8.5 Hz, 1H); 4.38 (d, J=7 Hz, 2H); 3.88 (s, 3H); 1.29 (t, J=7 Hz, 3H). mp: 200-202° C.

Example 4: 4-[(E)-[(1,1-dioxo-1,2-benzothiazol-3-yl)-(2-morpholinoethyl)hydrazono]methyl]-2-methoxy-phenol hydrochloride Step A: 2-methoxy-4-[(E)-(2-morpholinoethylhydrazono)methyl]phenol

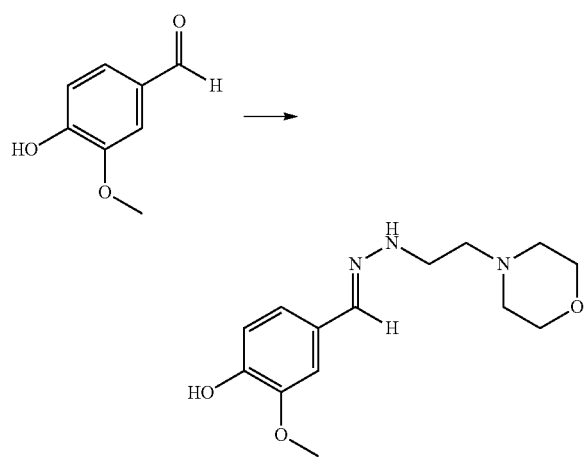

The compound was prepared using the same procedure detailed in example 1 step B starting from 4-hydroxy-3-methoxybenzaldehyde (150.0 mg; 0.99 mmol; 1 eq.) and 4-(2-hydrazinylethyl)morpholine (157.5 mg; 1.08 mmol; 1.1 eq.) giving 2-methoxy-4-[(E)-(2-morpholinoethylhydrazono)methyl]phenol (84.1 mg, 30%) as an orange solid, used without further purification in the following step. $^1$H NMR (CDCl$_3$, 300 MHz): δ 7.58 (s, 1H); 7.25 (d, J=1.8 Hz, 1H); 6.90 (dd, J=1.8 Hz, J=8.1 Hz, 1H); 6.87 (d, J=8.1 Hz, 1H); 3.93 (s, 3H); 3.72 (m, 4H); 3.31 (t, J=6.3 Hz, 2H); 2.63 (m, 2H); 2.48 (m, 4H).

Step B: 4-[(E)-[(1,1-dioxo-1,2-benzothiazol-3-yl)-(2-morpholinoethyl)hydrazono]methyl]-2-methoxy-phenol hydrochloride The compound was prepared using the same procedure detailed in example 1 step C starting from 2-methoxy-4-[(E)-(2-morpholinoethylhydrazono)methyl]phenol (84.0 mg; 0.30 mmol; 1.1 eq.) and 3-chloro-1,2-benzothiazole 1,1-dioxide (Example 1, step A, 55.1 mg; 0.27 mmol; 1 eq.) giving 4-[(E)-[(1,1-dioxo-1,2-benzothiazol-3-yl)-(2-morpholinoethyl) hydrazono]methyl]-2-methoxy-phenol hydrochloride (44.9 mg; 33%) as a yellow powder. $^1$H NMR (DMSO-$d_6$, 400 MHz): δ 10.45 (m broad, 1H); 9.85 (s, 1H); 8.87 (d, J=8 Hz, 1H); 8.60 (s, 1H); 8.10 (d, J=7.2 Hz, 1H); 7.95 (m, 2H); 7.47 (s, 1H); 7.38 (d, J=7.2 Hz, 1H); 6.97 (d, J=8.4 Hz, 1H); 4.78 (m, 2H); 3.92 (m, 2H); 3.88 (s, 3H); 3.62 (m, 4H); 3.55 (m, 2H); 3.27 (m, 2H). mp: 222-248° C.

Example 5: 4-[(E)-[(1,1-dioxo-1,2-benzothiazol-3-yl)-(3-hydroxypropyl)hydrazono]-methyl]-2-methoxy-phenol Step A: 4-[(E)-(3-hydroxypropylhydrazono)methyl]-2-methoxy-phenol

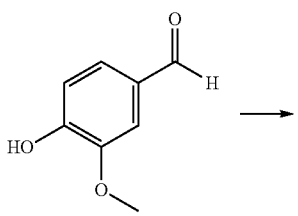

-continued

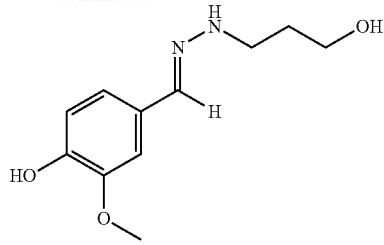

The compound was prepared using the same procedure detailed in example 1 step B starting from 4-hydroxy-3-methoxybenzaldehyde (200.0 mg; 1.31 mmol; 1 eq.) and 3-hydrazinylpropan-1-ol (130.3 mg; 1.45 mmol; 1.1 eq.) giving 4-[(E)-(3-hydroxy propylhydrazono)methyl]-2-methoxy-phenol (815.8 mg, quant.) as a yellow powder, used directly in the next step without further purification.

Step B: 4-[(E)-[(1,1-dioxo-1,2-benzothiazol-3-yl)-(3-hydroxypropyl)hydrazono]methy]-2-methoxy-phenol

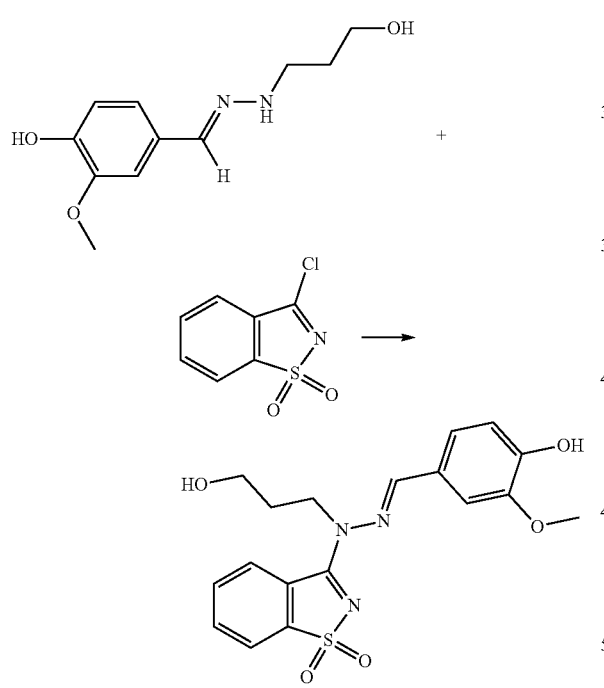

The compound was prepared using the same procedure detailed in example 1 step C starting from 4-[(E)-(3-hydroxypropylhydrazono)methyl]-2-methoxy-phenol (290.0 mg; 1.29 mmol; 1.1 eq.) and 3-chloro-1,2-benzothiazole 1,1-dioxide (Example 1, step A, 237.0 mg; 1.18 mmol; 1 eq.) giving 4-[(E)-[(1,1-dioxo-1,2-benzothiazol-3-yl)-(3-hydroxypropyl) hydrazono]methyl]-2-methoxy-phenol (164.1 mg; 36%) as a yellow powder. $^1$H NMR (DMSO-$d_6$, 400 MHz): δ 9.77 (s, 1H); 8.84 (dd, J=1.6 Hz, J=8.8 Hz; 1H); 8.44 (s, 1H); 8.06 (m, 1H); 7.90 (m, 2H); 7.42 (d, J=2.4 Hz, 1H); 7.30 (dd, J=2.4 Hz, J=10.8 Hz, 1H); 6.93 (d, J=10.8 Hz, 1H); 4.72 (t, J=5.2 Hz, 1H); 4.36 (dt, J=5.2 Hz, J=10.8 Hz, 2H); 3.89 (s, 3H); 3.56 (t, J=8.4 Hz, 2H); 1.85 (m, 2H). mp: 231-233° C.

Example 6: 4-[(E)-[3-(dimethylamino)propyl-(1,1-dioxo-1,2-benzothiazol-3-yl)hydrazono] methyl]-2-methoxy-phenol hydrochloride Step A: 4-[(E)-[3-(dimethylamino)propylhydrazono] methyl]-2-methoxy-phenol The compound was prepared using the same procedure detailed in example 1 step B starting from 4-hydroxy-3-methoxybenzaldehyde (200.0 mg; 1.31 mmol; 1 eq.) and [3-(dimethylamino)propyl]hydrazine dihydrochloride (374.9 mg; 1.97 mmol; 1.5 eq.) giving 4-[(E)-[3-(dimethylamino)propylhydrazono]methyl]-2-methoxy-phenol (585.0 mg; quant.) as a yellow oil, used without further purification in the next step. $^1$H NMR (DMSO-$d_6$, 300 MHz): δ 7.54 (s, 1H); 7.07 (d, J=3.3 Hz, 1H); 6.84 (dd, J=3.3 Hz, J=8.1 Hz, 1H); 6.74 (d, J=8.1 Hz, 1H); 3.77 (s, 3H); 3.12 (t, J=6.9 Hz, 2H); 2.92 (m, 2H); 2.62 (s, 6H); 1.87 (m, 2H).

Step B: 4-[(E)-[3-(dimethylamino)propyl-(1,1-dioxo-1,2-benzothiazol-3-yl)hydrazono]methyl]-2-methoxy-phenol hydrochloride

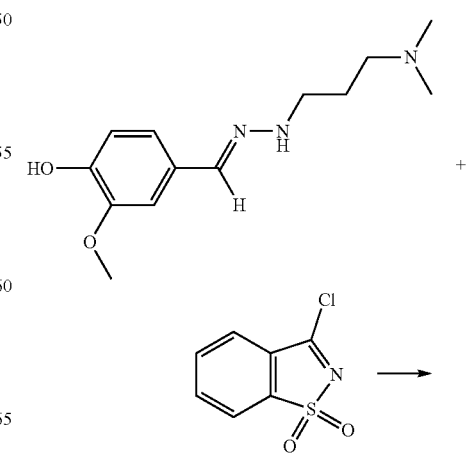

-continued

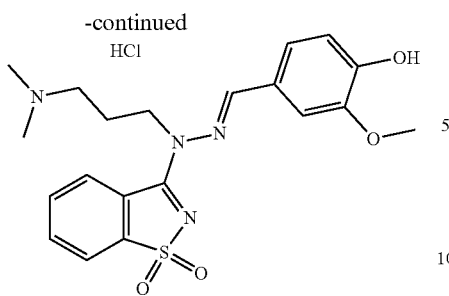

The compound was prepared using the same procedure detailed in example 1 step C starting from 4-[(E)-[3-(dimethylamino)propylhydrazono]methyl]-2-methoxy-phenol (330.0 mg; 1.31 mmol; 2 eq.) and 3-chloro-1,2-benzothiazole 1,1-dioxide (Example 1, step A, 132.4 mg; 0.66 mmol; 1 eq.) giving 4-[(E)-[3-(dimethylamino)propyl-(1,1-dioxo-1,2-benzothiazol-3-yl)hydrazono]methyl]-2-methoxy-phenol hydrochloride (205.0 mg; 69%) as a yellow powder. $^1$H NMR (DMSO-d$_6$, 400 MHz): δ 10.18 (m broad, 1H); 9.85 (s, 1H); 8.86 (dd, J=0.8 Hz, J=7.2 Hz, 1H); 8.52 (s, 1H); 8.09 (dd, J=0.8 Hz, J=7.2 Hz, 1H); 7.92 (m, 2H); 7.47 (d, J=2 Hz, 1H); 7.37 (dd, J=2 Hz, J=8.4 Hz, 1H); 6.98 (d, J=8.4 Hz, 1H); 4.43 (m, 2H); 3.89 (s, 3H); 3.24 (m, 2H); 2.78 (s, 6H); 2.14 (m, 2H). mp: 252-258° C.

Example 7: 4-[(E)-[(1,1-dioxo-1,2-benzothiazol-3-yl)-(2-methoxyethyl)hydrazono]-methyl]-2-methoxy-phenol Step A: 2-methoxy-4-[(E)-(2-methoxyethylhydrazono)methyl]phenol

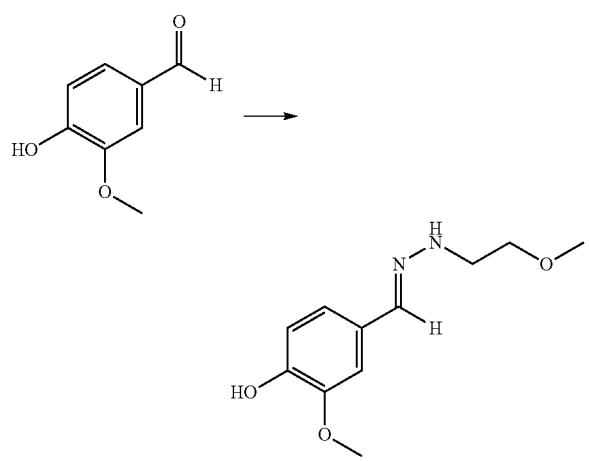

The compound was prepared using the same procedure detailed in example 1 step B starting from 4-hydroxy-3-methoxybenzaldehyde (150.0 mg; 0.99 mmol; 1 eq.) and 2-methoxyethylhydrazine hydrochloride (124.8 mg; 0.99 mmol; 1 eq.) giving 2-methoxy-4-[(E)-(2-methoxyethylhydrazono)methyl]phenol (255.0 mg; quant.) as an orange solid used without further purification in the next step. $^1$H NMR (DMSO-d$_6$, 300 MHz): δ 7.86 (s, 1H); 7.16 (d, J=2.1 Hz, 1H); 6.94 (dd, J=1.8 Hz, J=8.1 Hz, 1H); 6.77 (d, J=8.4 Hz, 1H); 3.77 (s, 3H); 3.52 (t, J=5.4 Hz, 2H); 3.30 (m, 2H); 3.29 (s, 3H).

Step B: 4-[(E)-[(1,1-dioxo-1,2-benzothiazol-3-yl)-(2-methoxyethyl)hydrazono]methyl]-2-methoxy-phenol

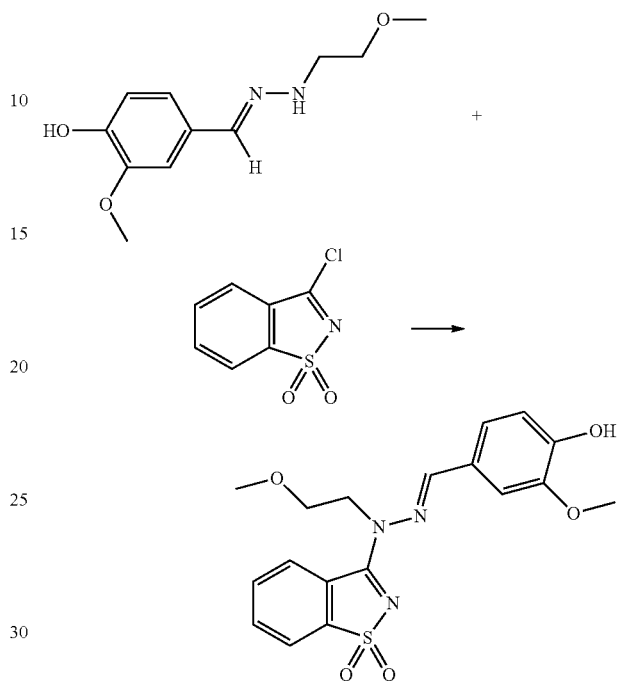

The compound was prepared using the same procedure detailed in example 1 step C starting from 2-methoxy-4-[(E)-(2-methoxyethylhydrazono)methyl]phenol (221.0 mg; 0.99 mmol; 1.1 eq.) and 3-chloro-1,2-benzothiazole 1,1-dioxide (Example 1, step A, 180.6 mg; 0.90 mmol; 1 eq.) giving 4-[(E)-[(1,1-dioxo-1,2-benzothiazol-3-yl)-(2-methoxyethyl) hydrazono]methyl]-2-methoxy-phenol (188.6 mg; 52%) as an orange powder. $^1$H NMR (DMSO-d$_6$, 400 MHz): δ. 9.78 (s, 1H); 8.84 (d, J=9.2 Hz, 1H); 8.50 (s, 1H); 8.08 (dd, J=2 Hz, J=9.2 Hz, 1H); 7.90 (m, 2H); 7.41 (d, J=2.4 Hz, 1H); 7.30 (dd, J=2 Hz, J=10.8 Hz, 1H); 6.94 (d, J=10.8 Hz, 1H); 4.55 (t, J=7.6 Hz, 2H); 3.89 (s, 3H); 3.72 (t, J=7.6 Hz, 2H); 3.30 (s, 3H). mp: 233° C.

Example 8: 3-[(1,1-dioxo-1,2-benzothiazol-3-yl)-[(E)-(4-hydroxy-3-methoxy-phenyl) methyleneamino]amino]propanoic acid Step A: 3-[(2E)-2-[(4-hydroxy-3-methoxy-phenyl)methylene]hydrazino]propanoic acid

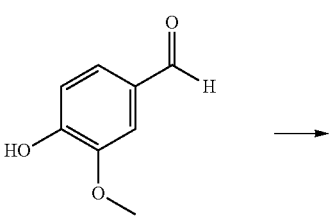

-continued

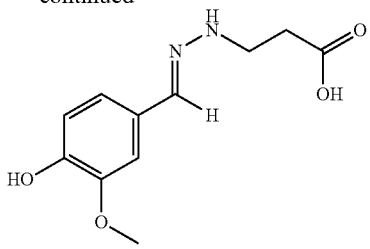

The compound was prepared using the same procedure detailed in example 1 step B starting from 4-hydroxy-3-methoxybenzaldehyde (200.0 mg; 1.31 mmol; 1 eq.) and 3-hydrazinopropanoic acid (164.2 mg; 1.58 mmol; 1.2 eq.) giving 3-[(2E)-2-[(4-hydroxy-3-methoxy-phenyl)methylene] hydrazino]propanoic acid (542.0 mg; quant.) as a brown oil used without further purification in the next step.

Step B: 3-[(1,1-dioxo-1,2-benzothiazol-3-yl)-[(E)-(4-hydroxy-3-methoxy-phenyl)methylene amino]amino]propanoic acid

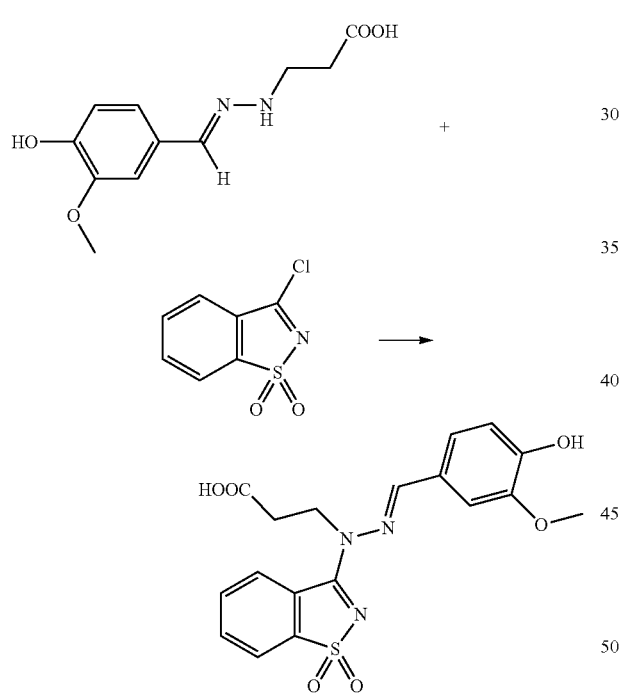

The compound was prepared using the same procedure detailed in example 1 step C starting from 3-[(2E)-2-[(4-hydroxy-3-methoxy-phenyl)methylene]hydrazino]propanoic acid (100.0 mg; 0.42 mmol; 1.1 eq.) and 3-chloro-1,2-benzothiazole 1,1-dioxide (Example 1, step A, 77.0 mg; 0.38 mmol; 1 eq.). The crude mixture which was purified by chromatography (Column: C18, 21.2×150 mm 5 μm phenomenex, Mobile phase: H₂O, 0.1% formic acid/ACN, 0.1% formic acid, Flowrate 25 ml/min, Gradient: 10-40-55-100 ACN) to give 3-[(1,1-dioxo-1,2-benzothiazol-3-yl)-[(E)-(4-hydroxy-3-methoxy-phenyl)methylene amino]amino]propanoic acid (22.4 mg; 14%) as a beige powder. $^1$H NMR (DMSO-d$_6$, 400 MHz): δ 12.5 (s broad, 1H); 9.77 (s, 1H); 8.84 (dd, J=0.8 Hz, J=6.8 Hz, 1H); 8.49 (s, 1H); 8.08 (m, 1H); 7.90 (m, 2H); 7.43 (d, J=2 Hz, 1H); 7.33 (dd, J=2 Hz, J=8.4 Hz, 1H); 6.94 (d, J=8 Hz, 1H); 4.52 (t, J=8 Hz, 2H); 3.88 (s, 3H); 2.72 (t, J=8 Hz, 2H).

Example 9: 2-[(1,1-dioxo-1,2-benzothiazol-3-yl)-[(E)-(4-hydroxy-3-methoxy-phenyl) methyleneamino]amino]-N-(2-hydroxyethyl)acetamide Step A: ethyl 2-[(2E)-2-[(4-hydroxy-3-methoxy-phenyl)methylene]hydrazino]acetate

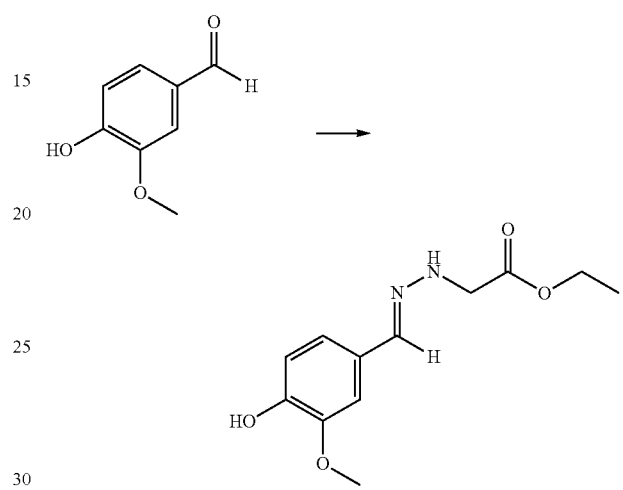

The compound was prepared using the same procedure detailed in example 1 step B starting from 4-hydroxy-3-methoxybenzaldehyde (500.0 mg; 3.29 mmol; 1 eq.) and ethyl hydrazinoacetate hydrochloride (508.0 mg; 3.29 mmol; 1 eq.) giving ethyl 2-[(2E)-2-[(4-hydroxy-3-methoxy-phenyl)methylene]hydrazino]acetate (1.01 g; quant.) used without further purification in the next step. $^1$H NMR (DMSO-d$_6$, 300 MHz): δ 7.68 (s, 1H); 7.10 (d, J=1.8 Hz, 1H); 6.88 (dd, J=1.8 Hz, J=8.1 Hz, 1H); 6.75 (d, J=8.1 Hz, 1H); 4.10 (q, J=6 Hz, 2H); 3.94 (s, 2H); 3.76 (s, 3H); 1.20 (t, J=6 Hz, 3H).

Step B: ethyl 2-[(1,1-dioxo-1,2-benzothiazol-3-yl)-[(E)-(4-hydroxy-3-methoxy-phenyl) methyleneamino]amino]acetate

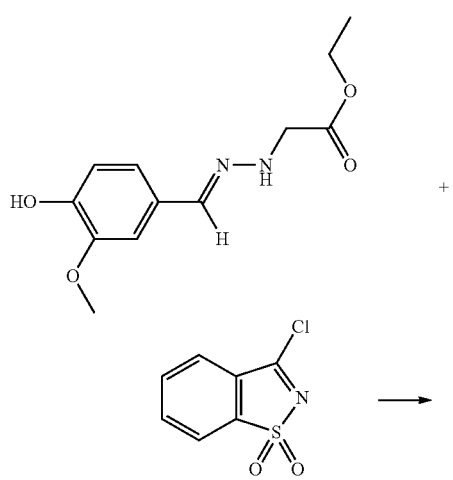

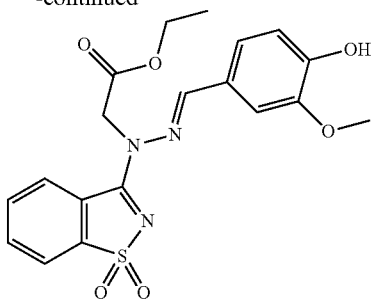

The compound was prepared using the same procedure detailed in example 1 step C starting from ethyl 2-[(2E)-2-[(4-hydroxy-3-methoxy-phenyl)methylene]hydrazino]acetate (829.0 mg; 3.29 mmol; 1.1 eq.) and 3-chloro-1,2-benzothiazole 1,1-dioxide (Example 1, step A, 602.4 mg; 2.99 mmol; 1 eq.) giving ethyl 2-[(1,1-dioxo-1,2-benzothiazol-3-yl)-[(E)-(4-hydroxy-3-methoxy-phenyl)methyleneamino]amino]acetate (930.0 mg; 74%) as a pale yellow powder. $^1$H NMR (DMSO-$d_6$, 300 MHz): δ 9.82 (s, 1H); 8.90 (dd, J=1.2 Hz, J=9.2 Hz, 1H); 8.34 (s, 1H); 8.10 (m, 1H); 7.94 (m, 2H); 7.40 (d, J=1.8 Hz, 1H); 7.30 (dd, J=2.1 Hz, J=8.4 Hz, 1H); 6.94 (d, J=8.4 Hz, 1H); 5.21 (s, 2H); 4.22 (q, J=6.9 Hz, 2H); 3.89 (s, 3H); 1.24 (t, J=6.9 Hz, 3H).

Step C: 2-[(1,1-dioxo-1,2-benzothiazol-3-yl)-[(E)-(4-hydroxy-3-methoxy-phenyl)methylene amino]amino]acetic acid

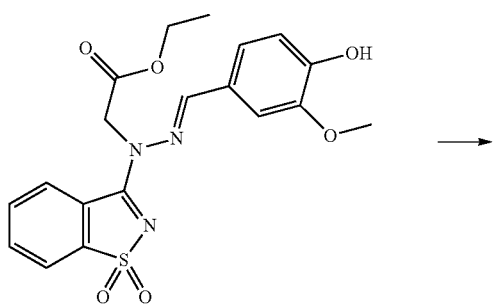

To a solution of ethyl 2-[(1,1-dioxo-1,2-benzothiazol-3-yl)-[(E)-(4-hydroxy-3-methoxy-phenyl)methyleneamino]amino]acetate (500.0 mg; 1.2 mmol; 1 eq.) in THF (15 mL) and water (10 mL) was added LiOH monohydrate (150.8 mg; 3.59 mmol; 3.00 eq.). The reaction mixture was stirred at room temperature for 1 h then concentrated under vacuum. Water was added followed by HCl 1 N until pH 2. The solid was filtered through a sintered-glass funnel, washed with water and dried to give 2-[(1,1-dioxo-1,2-benzothiazol-3-yl)-[(E)-(4-hydroxy-3-methoxy-phenyl)methyleneamino]amino]acetic acid (402.3 mg; 72%) as a pale yellow powder, used directly in the next step without further purification.

Step D: 2-[(1,1-dioxo-1,2-benzothiazol-3-yl)-[(E)-(4-hydroxy-3-methoxy-phenyl)methylene amino]amino]-N-(2-hydroxyethyl)acetamide

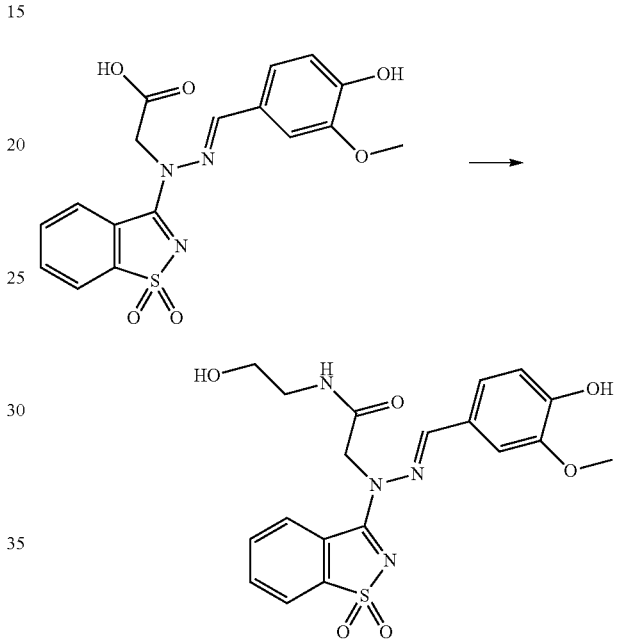

In a 10 mL round-bottom flask, 2-[(1,1-dioxo-1,2-benzothiazol-3-yl)-[(E)-(4-hydroxy-3-methoxy-phenyl)methyleneamino]amino]acetic acid (100.0 mg; 0.26 mmol; 1 eq.) was dissolved in DMF (1.2 mL). Then NMM (37 μL; 0.33 mmol; 1.3 eq.) was added followed by the addition of HATU (126.9 mg; 0.33 mmol; 1.3 eq.) and the reaction mixture was stirred at room temperature for 40 min. 2-aminoethanol (20 μL; 0.33 mmol; 1.30 eq.) was added and the reaction mixture was stirred at room temperature for 21 h. The mixture was concentrated under reduce pressure and EtOH was added. The mixture was filtered through a sintered-glass funnel and the filtrate was concentrated under reduce pressure. The crude residue was purified by chromatography (Column: SUNFIRE C18, 30×100 mm 5 μm (WATERS), Flowrate: 42 ml/min, Mobile phase: H$_2$O/ACN, Gradient: 10-30-45-90 ACN) to give 2-[(1,1-dioxo-1,2-benzothiazol-3-yl)-[(E)-(4-hydroxy-3-methoxy-phenyl)methylene amino]amino]-N-(2-hydroxyethyl)acetamide (38.8 mg; 35%) as a beige powder. $^1$H NMR (DMSO-$d_6$, 400 MHz): δ 9.77 (s broad, 1H); 8.90 (d, J=7.6 Hz, 1H); 8.38 (t, J=5.6 Hz, 1H); 8.16 (s, 1H); 8.08 (m, 1H); 7.92 (m, 2H); 7.37 (d, J=1.6 Hz, 1H); 7.27 (dd, J=2 Hz, J=8 Hz, 1H); 6.92 (d, J=8 Hz, 1H); 5.05 (s, 2H); 4.76 (m, 1H); 3.89 (s, 3H); 3.45 (m, 2H); 3.20 (q, J=5.6 Hz, 2H). mp: 234° C.

Example 10: 4-[(E)-[(1,1-dioxo-1,2-benzothiazol-3-yl)-(3-methoxypropyl)hydrazono]-ethyl]-2-methoxyphenol

Step A: 2-methoxy-4-[(E)-(3-methoxypropylhydrazono)methyl]phenol

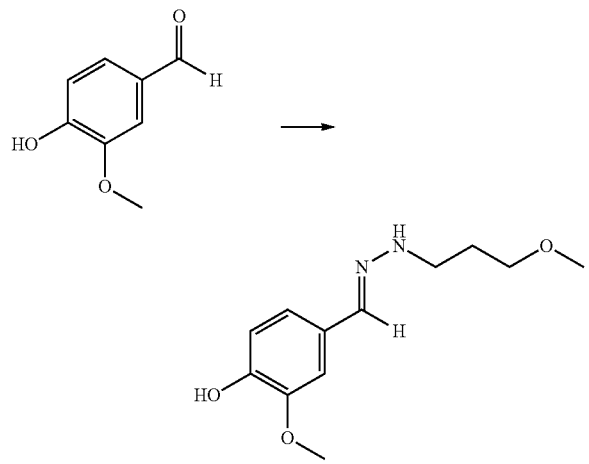

The compound was prepared using the same procedure detailed in example 1 step B starting from 4-hydroxy-3-methoxybenzaldehyde (200.0 mg; 1.31 mmol; 1 eq.) and (3-methoxypropyl)hydrazine hydrochloride (184.8 mg; 1.31 mmol; 1 eq.) giving 2-methoxy-4-[(E)-(3-methoxypropylhydrazono)methyl]phenol (379.1 mg; 87%) as an orange solid, used without purification in the next step. $^1$H NMR (DMSO-$d_6$, 300 MHz): δ 9.77 (s, 1H); 8.53 (s, 1H); 7.31 (d, J=1.8 Hz, 1H); 7.20 (dd, J=2.1 Hz, J=8.1 Hz, 1H); 6.90 (d, J=8.4 Hz, 1H); 3.86 (m, 2H); 3.84 (s, 3H); 3.25 (s, 3H); 3.24 (m, 2H); 1.95 (m, 2H).

Step B: 4-[(E)-[(1,1-dioxo-1,2-benzothiazol-3-yl)-(3-methoxypropyl)hydrazono]methyl]-2-methoxyphenol

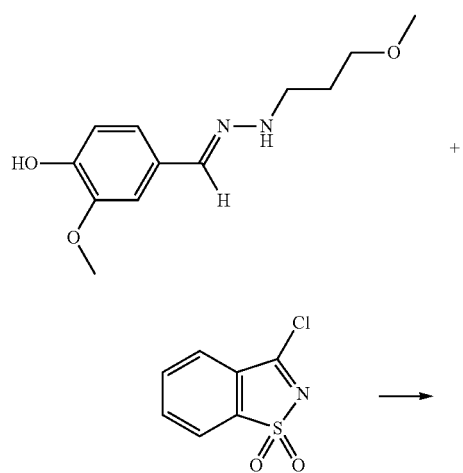

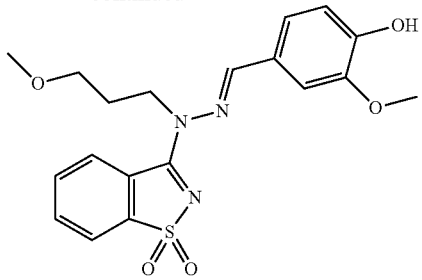

The compound was prepared using the same procedure detailed in example 1 step C starting from 2-methoxy-4-[(E)-(3-methoxypropylhydrazono)methyl]phenol (370.0 mg; 1.55 mmol; 1.1 eq.) and 3-chloro-1,2-benzothiazole 1,1-dioxide (Example 1, step A, 284.6 mg; 1.41 mmol; 1 eq.) giving 4-[(E)-[(1,1-dioxo-1,2-benzothiazol-3-yl)-(3-methoxypropyl) hydrazono]methyl]-2-methoxy-phenol (132.8 mg; 22%) as a yellow powder. $^1$H NMR (DMSO-$d_6$, 400 MHz): δ 9.78 (s broad, 1H); 8.85 (d, J=6.8 Hz, 1H); 8.41 (s, 1H); 8.07 (m, 1H); 7.90 (m, 2H); 7.43 (d, J=2 Hz, 1H); 7.32 (dd, J=2 Hz, J=8.4 Hz, 1H); 6.95 (d, J=8 Hz, 1H); 4.40 (t, J=7.6 Hz, 2H); 3.89 (s, 3H); 3.45 (t, J=7.2 Hz, 2H); 3.26 (s, 3H); 1.95 (quint., J=7.6 Hz, 2H). mp: 210° C.

Example 11: 4-[(E)-[2-hydroxyethyl-(5-methoxy-1,1-dioxo-1,2-benzothiazol-3-yl)hydrazono]methyl]-2-methoxy-phenol

Step A: 3-chloro-5-methoxy-1,2-benzothiazole 1,1-dioxide

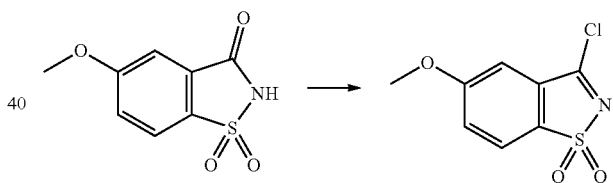

The compound was prepared using the same procedure detailed in example 1 step A starting from 5-methoxy-2,3-dihydro-1λ$^6$,2-benzothiazole-1,1,3-trione (1.00 g; 4.69 mmol; 1 eq.) to give 3-chloro-5-methoxy-1,2-benzothiazole 1,1-dioxide (1.03 g; 95%). $^1$H NMR (DMSO-$d_6$, 300 MHz): δ 8.08 (d, J=8.4 Hz, 1H); 7.46 (m, 2H); 3.94 (s, 3H).

Step B: 4-[(E)-[2-hydroxyethyl-(5-methoxy-1,1-dioxo-1,2-benzothiazol-3-yl)hydrazono]methyl]-2-methoxy-phenol

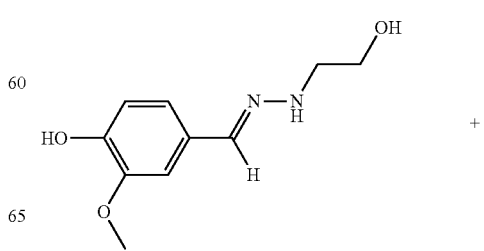

-continued

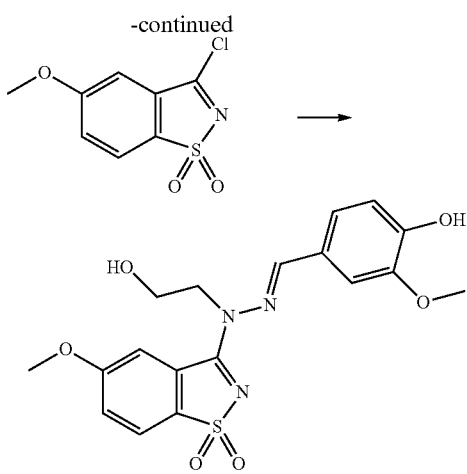

The compound was prepared using the same procedure detailed in example 1 step C starting from 3-chloro-5-methoxy-1,2-benzothiazole 1,1-dioxide (404.0 mg; 1.74 mmol; 1 eq.) and 4-[(E)-(2-hydroxyethylhydrazono)methyl]-2-methoxy-phenol (example 2, step A, 550.0 mg; 2.62 mmol; 1.5 eq.) giving 4-[(E)-[2-hydroxyethyl-(5-methoxy-1,1-dioxo-1,2-benzothiazol-3-yl)hydrazono]methyl]-2-methoxy-phenol (305.3 mg; 42%) as a pale yellow powder. $^1$H NMR (DMSO-$d_6$, 400 MHz): δ 9.80 (s broad, 1H); 8.54 (s, 1H); 8.39 (d, J=2 Hz, 1H); 7.99 (d, J=8.4 Hz, H); 7.40 (m, 2H); 7.29 (dd, J=2 Hz, J=8.4 Hz, 1H); 6.94 (d, J=8 Hz, 1H); 5.12 (m, 1H); 4.39 (t, J=6 Hz, 2H); 3.92 (s, 3H); 3.87 (s, 3H); 3.78 (m, 2H). mp: 230-236° C.

Example 12: 2-methoxy-4-[(E)-[(5-methoxy-1,1-dioxo-1,2-benzothiazol-3-yl)-(2-morpholino ethyl)hydrazono]methyl]phenol

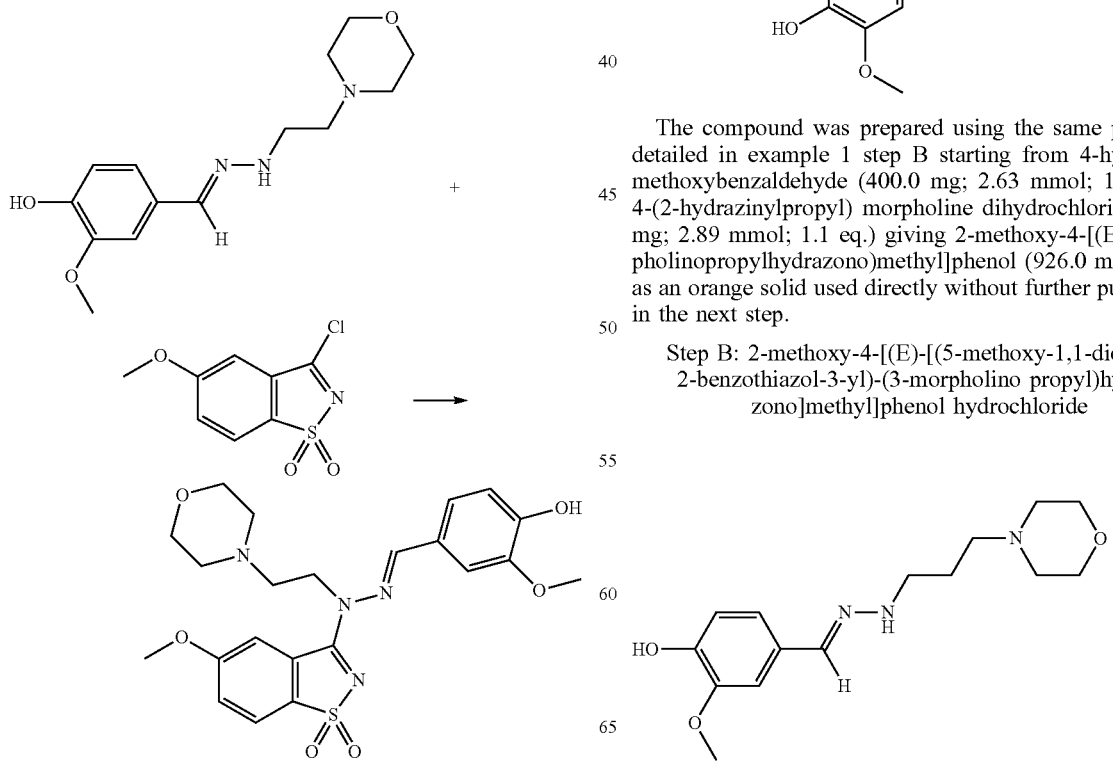

The compound was prepared using the same procedure detailed in example 1 step C starting from 3-chloro-5-methoxy-1,2-benzothiazole 1,1-dioxide (example 11, step A, 405.8 mg; 1.75 mmol; 1 eq.) and 2-methoxy-4-[(E)-(2-morpholinoethylhydrazono)methyl]phenol (example 4, step A, 734.0 mg; 2.63 mmol; 1.5 eq.) giving 2-methoxy-4-[(E)-[(5-methoxy-1,1-dioxo-1,2-benzothiazol-3-yl)-(2-morpholinoethyl)hydrazono]methyl]phenol (258.7 mg; 31%) as a beige powder. $^1$H NMR (DMSO-de, 400 MHz): δ 9.81 (s broad, 1H); 8.46 (s, 1H); 8.39 (d, J=2.4 Hz, 1H) 7.99 (d, J=8.4 Hz, 1H); 7.43 (d, J=2 Hz, 1H); 7.40 (dd, J=2.4 Hz, J=8.4 Hz, 1H); 7.30 (dd, J=2 Hz, J=8.4 Hz, 1H); 6.92 (d, J=8 Hz, 1H); 4.46 (t, J=6.4 Hz, 2H); 3.92 (s, 3H); 3.88 (s, 3H); 3.54 (t, J=4.8 Hz, 4H); 2.66 (t, J=6.8 Hz, 2H); 2.49 (m, 4H). mp: 210-216° C.

Example 13: 2-methoxy-4-[(E)-[(5-methoxy-1,1-dioxo-1,2-benzothiazol-3-yl)-(3-morpholino propyl)hydrazono]methyl]phenol hydrochloride Step A: 2-methoxy-4-[(E)-(3-morpholinopropylhydrazono)methyl]phenol

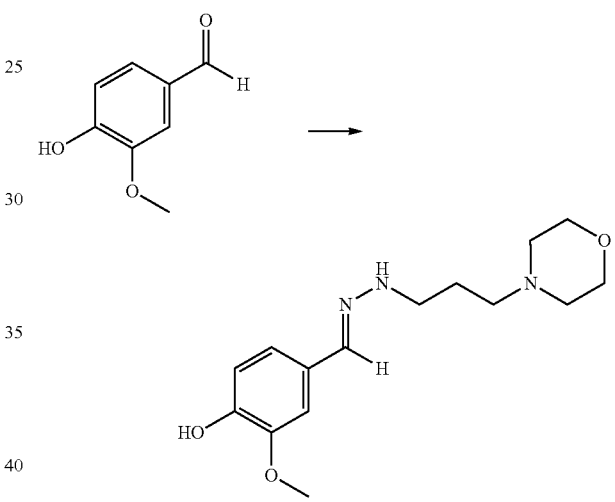

The compound was prepared using the same procedure detailed in example 1 step B starting from 4-hydroxy-3-methoxybenzaldehyde (400.0 mg; 2.63 mmol; 1 eq.) and 4-(2-hydrazinylpropyl) morpholine dihydrochloride (671.4 mg; 2.89 mmol; 1.1 eq.) giving 2-methoxy-4-[(E)-(3-morpholinopropylhydrazono)methyl]phenol (926.0 mg; quant.) as an orange solid used directly without further purification in the next step.

Step B: 2-methoxy-4-[(E)-[(5-methoxy-1,1-dioxo-1,2-benzothiazol-3-yl)-(3-morpholino propyl)hydrazono]methyl]phenol hydrochloride

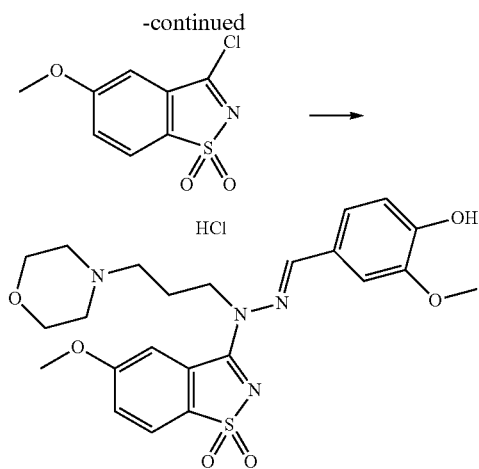

The compound was prepared using the same procedure detailed in example 1 step C starting from 3-chloro-5-methoxy-1,2-benzothiazole 1,1-dioxide (example 11, step A, 405.4 mg; 1.75 mmol; 1 eq.) and 2-methoxy-4-[(E)-(3-morpholinopropylhydrazono)methyl]phenol (770.0 mg; 2.62 mmol; 1.5 eq.) giving 2-methoxy-4-[(E)-[(5-methoxy-1-dioxo-1,2-benzothiazol-3-yl)-(3-morpholinopropyl)hydrazono]methyl]phenol hydrochloride (316.7 mg; 34%) as a yellow powder. $^1$H NMR (DMSO-$d_6$, 400 MHz): δ 10.56 (s broad, 1H); 9.84 (s, 1H); 8.49 (s, 1H); 8.40 (d, J=2.4 Hz, 1H); 8.01 (d, J=8.4 Hz, 1H); 7.47 (d, J=1.6 Hz, 1H); 7.42 (dd, J=2.4 Hz, J=8.4 Hz, 1H); 7.34 (dd, J=2 Hz, J=8 Hz, 1H); 6.95 (d, J=8 Hz, 1H); 4.41 (t, J=7.6 Hz, 2H); 3.95 (m, 2H); 3.92 (s, 3H); 3.88 (s, 3H); 3.73 (m, 2H); 3.43 (m, 2H); 3.28 (m, 2H); 3.09 (m, 2H); 2.18 (m, 2H). mp: 227-253° C.

Example 14: 4-[(E)-[3-hydroxypropyl-(5-methoxy-1,1-dioxo-1,2-benzothiazol-3-yl) hydrazono]methyl]-2-methoxy-phenol

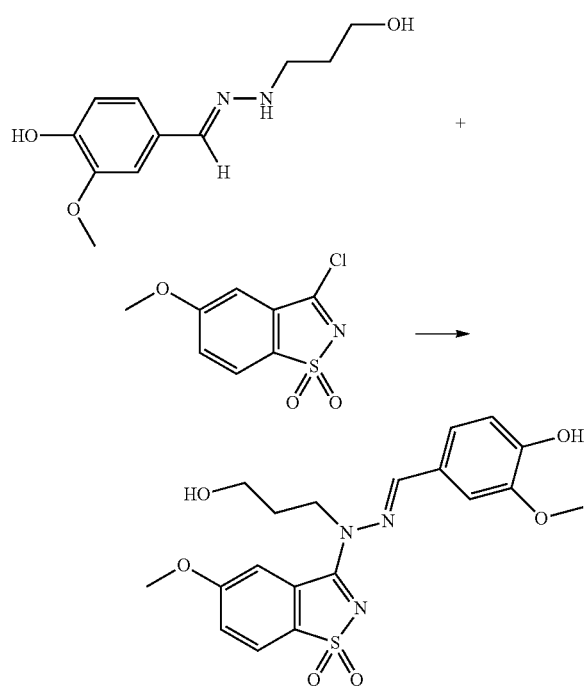

The compound was prepared using the same procedure detailed in example 1 step C starting from 3-chloro-5-methoxy-1,2-benzothiazole 1,1-dioxide (example 11, step A, 405.6 mg; 1.75 mmol; 1 eq) and 4-[(E)-(3-hydroxypropylhydrazono)methyl]-2-methoxy-phenol (example 5, step A, 589.0 mg; 2.63 mmol; 1.5 eq.) giving 4-[(E)-[3-hydroxypropyl-(5-methoxy-1,1-dioxo-1,2-benzothiazol-3-yl)hydrazono]methyl]-2-methoxy-phenol (202.4 mg; 27%) as a yellow powder. $^1$H NMR (DMSO-$d_6$, 400 MHz): δ 9.78 (s, 1H); 8.42 (s, 1H); 8.40 (d, J=2.4 Hz, 1H); 7.98 (d, J=8.4 Hz, 1H); 7.44 (d, J=2 Hz, 1H); 7.40 (dd, J=2.4 Hz, J=8.8 Hz, 1H); 7.30 (dd, J=1.6 Hz, J=8. Hz, 1H); 6.92 (d, J=8 Hz, 1H); 4.71 (t, J=4.8 Hz, 1H); 4.36 (t, J=7.6 Hz, 2H); 3.92 (s, 3H); 3.88 (s, 3H); 3.55 (q, J=6 Hz, 2H); 1.87 (m, 2H). mp: 195-197° C.

Example 15: 2-methoxy-4-[(E)-[(5-methoxy-1,1-dioxo-1,2-benzothiazol-3-yl)-(2-methoxy ethyl)hydrazono]methyl]phenol

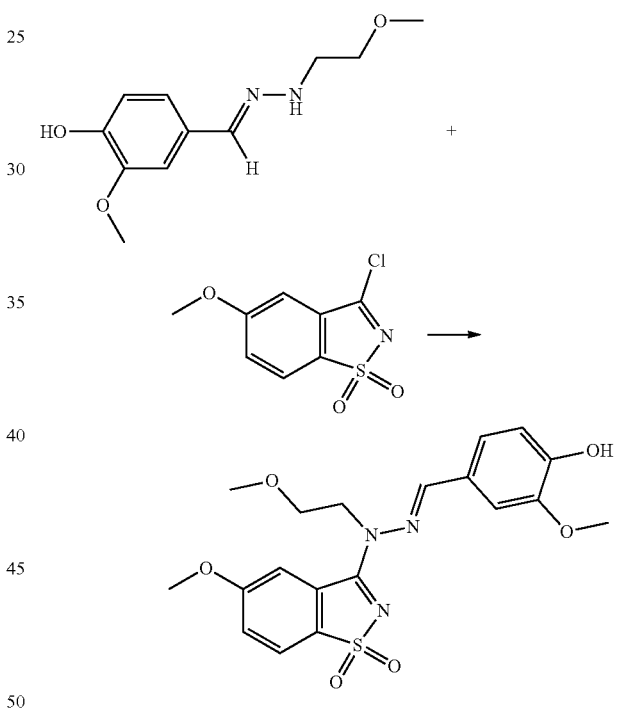

The compound was prepared using the same procedure detailed in example 1 step C starting from 3-chloro-5-methoxy-1,2-benzothiazole 1,1-dioxide (example 11, step A, 200.0 mg; 0.86 mmol; 1 eq) and 2-methoxy-4-[(E)-(2-methoxyethylhydrazono)methyl]phenol (example 7, step A, 283.9 mg; 0.95 mmol; 1.1 eq.) giving 2-methoxy-4-[(E)-[(5-methoxy-1,1-dioxo-1,2-benzothiazol-3-yl)-(2-methoxyethyl)hydrazono]methyl]phenol (236.9 mg; 64%) as a yellow powder. $^1$H NMR (DMSO-$d_6$, 400 MHz): δ 9.78 (s, 1H); 8.48 (s, 1H); 8.39 (d, J=2.4 Hz, 1H); 7.99 (d, J=10 Hz, 1H); 7.42 (s, 1H); 7.40 (dd, J=2.4 Hz, J=8.8 Hz, 1H); 7.29 (dd, J=1.6 Hz, J=8 Hz, 1H); 6.92 (d, J=8 Hz, 1H); 4.52 (t, J=5.6 Hz, 2H); 3.92 (s, 3H); 3.88 (s, 3H); 3.72 (t, J=5.6 Hz, 2H); 3.24 (s, 3H). mp: 212° C.

Example 16: 4-[(E)-[(5,7-dimethoxy-1,1-dioxo-1,2-benzothiazol-3-yl)-methyl-hydrazono] methyl]-2-methoxy-phenol Step A: 3-chloro-5,7-dimethoxy-1,2-benzothiazole 1,1-dioxide

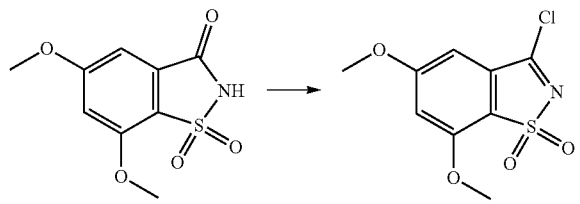 [SMILES: COc1cc(OC)c2c(c1)C(=O)NS2(=O)=O ; COc1cc(OC)c2c(c1)C(Cl)=NS2(=O)=O]

The compound was prepared using the same procedure detailed in example 1 step A starting from 5,7-dimethoxy-2,3-dihydro-1λ⁶,2-benzothiazole-1,1,3-trione (1.00 g; 4.11 mmol; 1 eq.) to give 3-chloro-5,7-dimethoxy-1,2-benzothiazole 1,1-dioxide (1.08 g; quant.) as a beige solid used without further purification in the next step. $^1$H NMR (DMSO-$d_6$, 300 MHz): δ 7.07 (d, J=1.8 Hz, 1H); 7.02 (d, J=2.1 Hz, 1H); 3.99 (s, 3H); 3.94 (s, 3H).

Step B: 4-[(E)-[(5,7-dimethoxy-1,1-dioxo-1,2-benzothiazol-3-yl)-methyl-hydrazono]methyl]-2-methoxy-phenol

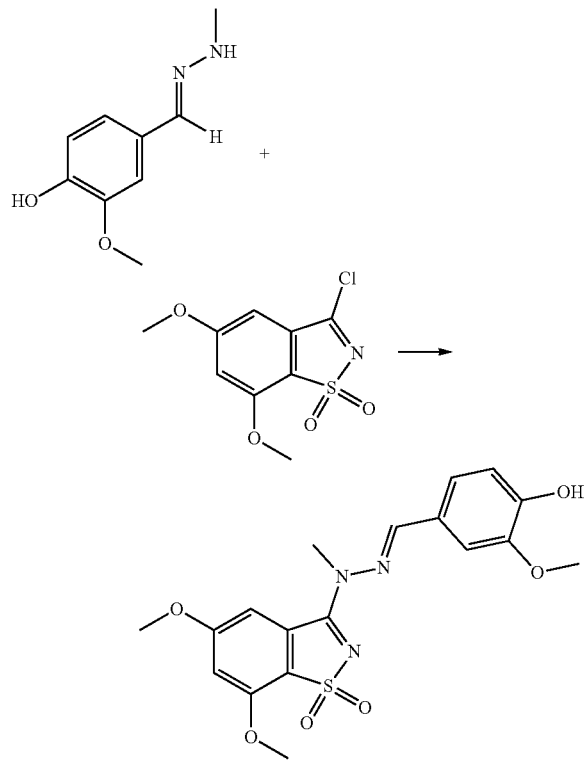

The compound was prepared using the same procedure detailed in example 1 step C starting from 3-chloro-5,7-dimethoxy-1,2-benzothiazole 1,1-dioxide (172.1 mg; 0.66 mmol; 1 eq.) and 2-methoxy-4-[(E)-(methylhydrazono)methyl]phenol (example 1, step B, 237.0 mg; 1.32 mmol; 2 eq.) giving 4-[(E)-[(5,7-dimethoxy-1,1-dioxo-1,2-benzothiazol-3-yl)-methyl-hydrazono]methyl]-2-methoxy-phenol (235.0 mg; 82%) as a beige solid. $^1$H NMR (DMSO-$d_6$, 400 MHz): δ 9.80 (s, 1H); 8.32 (s, 1H); 8.02 (d, J=2 Hz, 1H); 7.40 (d, J=1.6 Hz, 1H); 7.28 (dd, J=1.6 Hz, J=8 Hz, 1H); 6.99 (d, J=2 Hz, H); 6.92 (d, J=8.4 Hz, 1H); 3.99 (s, 3H); 3.94 (s, 3H); 3.86 (s, 3H); 3.72 (s, 3H). mp >260° C.

Example 17: 4-[(E)-[(5,7-dimethoxy-1,1-dioxo-1,2-benzothiazol-3-yl)-(2-hydroxyethyl) hydrazono] methyl]-2-methoxy-phenol

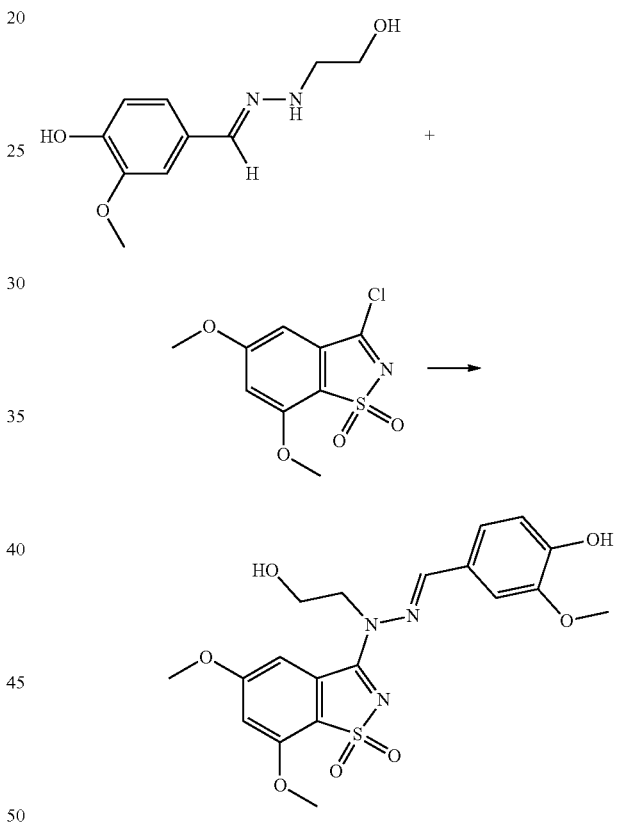

The compound was prepared using the same procedure detailed in example 1 step C starting from 3-chloro-5,7-dimethoxy-1,2-benzothiazole 1,1-dioxide (example 16, step A, 171.9 mg; 0.66 mmol; 1 eq.) and 4-[(E)-(2-hydroxyethylhydrazono)methyl]-2-methoxy-phenol (example 2, step A, 276.3 mg; 1.31 mmol; 2 eq.) giving 4-[(E)-[(5,7-dimethoxy-1,1-dioxo-1,2-benzothiazol-3-yl)-(2-hydroxyethyl)hydrazono]methyl]-2-methoxy-phenol (66.0 mg; 23%) as a yellow powder. $^1$H NMR (DMSO-$d_6$, 400 MHz): δ 9.82 (s, broad, 1H); 8.55 (s, 1H); 7.96 (d, J=2 Hz, 1H); 7.40 (d, J=2 Hz, 1H); 7.28 (dd, J=2 Hz, J=8.4 Hz, 1H); 7.00 (d, J=1.6 Hz, H); 6.94 (d, J=8 Hz, 1H); 5.18 (t, J=5.2 Hz, 1H); 4.36 (t, J=5.6 Hz, 2H); 3.99 (s, 3H); 3.93 (s, 3H); 3.86 (s, 3H); 3.75 (m, 2H). mp >260° C.

Example 18: 4-[(E)-[(5,7-dimethoxy-1,1-dioxo-1,2-benzothiazol-3-yl)-(2-morpholino-ethyl)hydrazono]methyl]-2-methoxy-phenol hydrochloride

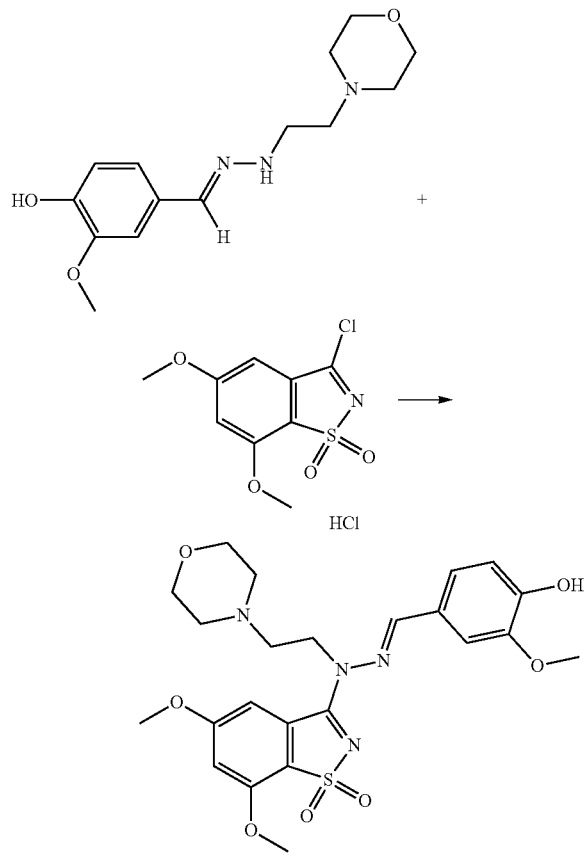

The compound was prepared using the same procedure detailed in example 1 step C starting from 3-chloro-5,7-dimethoxy-1,2-benzothiazole 1,1-dioxide (example 16, step A, 229.3 mg; 0.88 mmol; 1 eq.) and 2-methoxy-4-[(E)-(2-morpholinoethylhydrazono) methyl]phenol (example 4, step A, 367.2 mg; 1.31 mmol; 1.5 eq.) giving 4-[(E)-[(5,7-dimethoxy-1,1-dioxo-1,2-benzothiazol-3-yl)-(2-morpholinoethyl)hydrazono]methyl]-2-methoxy-phenol hydrochloride (139.0 mg; 29%) as an off-white powder. $^1$H NMR (DMSO-d$_6$, 400 MHz): δ 11.70 (s broad, 1H); 9.86 (s, 1H); 8.78 (s, 1H); 7.98 (d, J=2 Hz, 1H); 7.50 (s, 1H); 7.38 (d, J=7.6 Hz, 1H); 7.04 (d, J=1.6 Hz, 1H); 6.95 (d, J=8.4 Hz, 1H); 4.74 (m, 2H); 4.01 (s, 3H); 3.99 (m, 2H); 3.95 (s, 3H); 3.86 (s, 3H); 3.80 (m, 2H); 3.57 (m, 2H); 3.48 (m, 2H); 3.26 (m, 2H). mp: 262° C.

Example 19: 4-[(E)-[(5,7-dimethoxy-1,1-dioxo-1,2-benzothiazol-3-yl)-(2-methoxyethyl) hydrazono]methyl]-2-methoxy-phenol

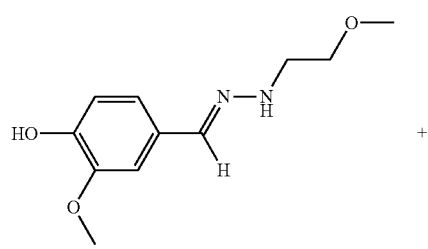

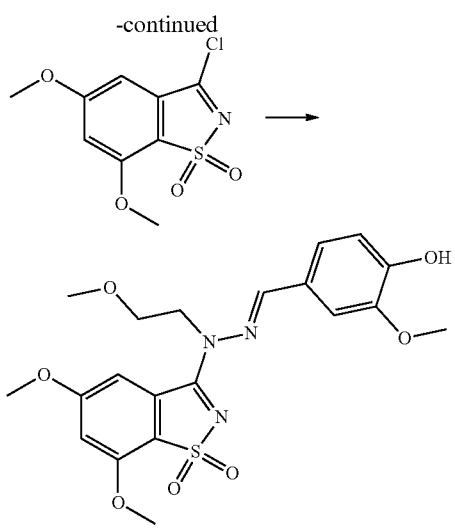

The compound was prepared using the same procedure detailed in example 1 step C starting from 3-chloro-5,7-dimethoxy-1,2-benzothiazole 1,1-dioxide (example 16, step A, 100.0 mg; 0.38 mmol; 1 eq.) and 2-methoxy-4-[(E)-(2-methoxyethylhydrazono) methyl]phenol (example 7, step A, 125.7 mg; 0.42 mmol; 1.1 eq.) giving 4-[(E)-[(5,7-dimethoxy-1,1-dioxo-1,2-benzothiazol-3-yl)-(2-methoxyethyl)hydrazono]methyl]-2-methoxy-phenol. (59.9 mg; 34%) as an orange powder $^1$H NMR (DMSO-d$_6$, 400 MHz): δ 9.76 (s, 1H); 8.45 (s, 1H); 7.96 (d, J=2 Hz, 1H); 7.39 (d, J=1.6 Hz, 1H); 7.27 (dd, J=2 Hz, J=8 Hz, 1H); 7.00 (d, J=2 Hz, 1H); 6.91 (d, J=8 Hz, 1H); 4.49 (t, J=5.6 Hz, 2H); 3.99 (s, 3H); 3.93 (s, 3H); 3.86 (s, 3H); 3.69 (t, J=5.6 Hz, 2H); 3.29 (s, 3H). mp: 238° C.

Example 20: 4-[(E)-[(5-fluoro-7-methyl-1,1-dioxo-1,2-benzothiazol-3-yl)-methyl-hydrazono] methyl]-2-methoxy-phenol Step A:
3-chloro-5-fluoro-7-methyl-1,2-benzothiazole 1,1-dioxide

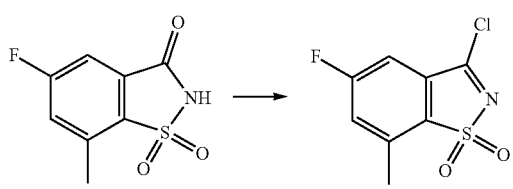

The compound was prepared using the same procedure detailed in example 1 step A starting from 5-fluoro-7-methyl-2,3-dihydro-1λ$^6$,2-benzothiazole-1,1,3-trione (1.00 g; 4.65 mmol; 1 eq.) to give 3-chloro-5-fluoro-7-methyl-1,2-benzothiazole 1,1-dioxide (500.0 mg; 46%) as a brown solid. $^1$H NMR (DMSO-d$_6$, 300 MHz): δ 7.72 (m, 1H); 7.69 (m, 1H); 2.58 (s, 3H).

Step B: 4-[(E)-[(5-fluoro-7-methyl-1,1-dioxo-1,2-benzothiazol-3-yl)-methyl-hydrazono]methyl]-2-methoxy-phenol

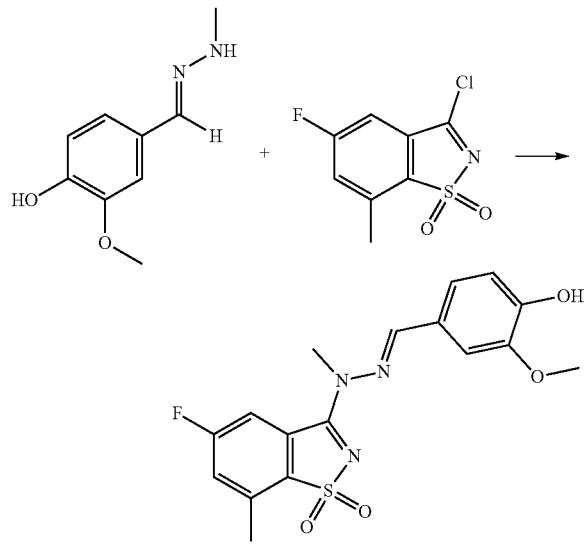

The compound was prepared using the same procedure detailed in example 1 step C starting from 3-chloro-5-fluoro-7-methyl-1,2-benzothiazole 1,1-dioxide (150.0 mg; 0.64 mmol; 1 eq.) and 2-methoxy-4-[(E)-(methylhydrazono)methyl]phenol (example 1, step B, 231.4 mg; 1.28 mmol; 2 eq.) giving 4-[(E)-[(5-fluoro-7-methyl-1,1-dioxo-1,2-benzothiazol-3-yl)-methyl-hydrazono]methyl]-2-methoxy-phenol (136.0 mg; 56%) as a yellow powder. $^1$H NMR (DMSO-$d_6$, 400 MHz): δ 9.81 (s, 1H); 8.48 (d, J=9.2 Hz, 1H); 8.36 (s, 1H); 7.62 (d, J=8.4 Hz, 1H); 7.41 (s, 1H); 7.25 (d, J=7.2 Hz, 1H); 6.93 (d, J=8.4 Hz, 1H); 3.88 (s, 3H); 3.75 (s, 3H); 2.60 (s, 3H). mp >260° C.

Example 21: 2-methoxy-4-[(E)-[(7-methoxy-1,1-dioxo-1,2-benzothiazol-3-yl)-methyl-hydrazono]methyl]phenol Step A: 2-methoxy-N-(1-methyl-1-phenyl-ethyl)benzenesulfonamide

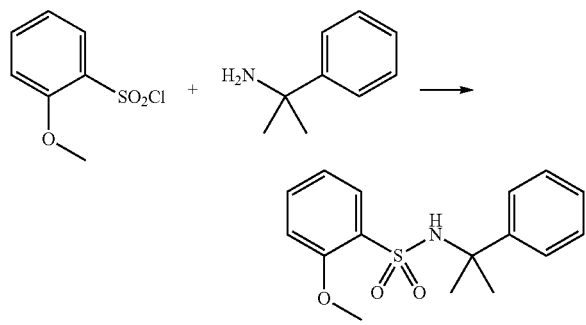

To a stirred suspension of cumylamine (1.22 mL; 8.48 mmol; 2.4 eq.) and TEA (591 μL; 4.24 mmol; 1.2 eq.) in DCM (10 mL) at 0° C. was slowly added 2-methoxybenzenesulfonyl chloride (730.0 mg; 3.53 mmol; 1 eq.) in solution into DCM (3.00 mL) (over 2 minutes). The mixture was stirred at rt for 3 h. The reaction mixture was diluted with DCM and acidified by HCl 1N. The organic layer was dried over MgSO$_4$ and concentrated under vacuum to give 2-methoxy-N-(1-methyl-1-phenyl-ethyl)benzenesulfonamide (874.0 mg; 81%) as a white powder. $^1$H NMR (DMSO-$d_6$, 300 MHz): δ 7.49 (m, 3H); 7.32 (m, 2H); 7.14 (m, 4H); 6.95 (t, J=7.8 Hz, 1H); 3.87 (s, 3H); 1.43 (s, 6H).

Step B: N,N-diethyl-3-methoxy-2-[(1-methyl-1-phenyl-ethyl)sulfamoyl]benzamide

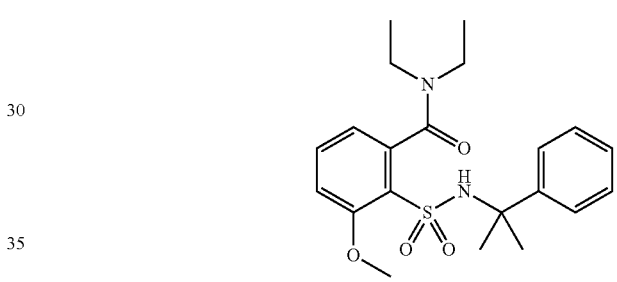

To a solution (in a flame-dried three-necked flask under Argon) of 2-methoxy-N-(1-methyl-1-phenyl-ethyl)benzenesulfonamide (870.0 mg; 2.85 mmol; 1 eq.) and TMEDA (946 μL; 6.27 mmol; 2.2 eq.) in THF (25 mL) cooled to −74° C. was added dropwise a solution of s-Buli (4.48 mL; 1.6 mol/L in hexane; 6.27 mmol; 2.2 eq.). The resulting yellow solution was allowed to stir for 2 hours. Then, diethylcarbamoyl chlorid (433 μl; 3.42 mmol; 1.2 eq.) was added dropwise (T maintained between −70° C. and −65° C.) and the mixture was allowed to warm slowly to room temperature over 45 min. Saturated NH$_4$Cl was added and the mixture was extracted with EtOAc. The combined organic layers were washed with brine, dried over MgSO$_4$ and concentrated under vacuum. The crude residue was purified by chromatography (column SiO$_2$ 25 g, flow rate 50 mL/min, gradient from 100% cyclohexane to 50/50 cyclohexane/EtOAc) to give N,N-diethyl-3-methoxy-2-[(1-methyl-1-phenyl-ethyl)sulfamoyl]benzamide (170.0 mg; 15%) as a white powder. $^1$H NMR (DMSO-de, 300 MHz): δ 7.49 (dd, J=7.5 Hz, J=8.4 Hz, 1H); 7.43 (s, 1H); 7.36 (m, 2H); 7.14 (m, 3H); 7.02 (dd, J=1 Hz, J=8.4 Hz, 1H); 6.70 (dd, J=1 Hz, J=7.5 Hz, 1H); 3.86 (s, 3H); 3.46 (m, 1H); 3.20 (m, 1H); 2.88 (q, J=7.2 Hz, 2H); 1.50 (s, 3H); 1.43 (s, 3H); 1.05 (t, J=6.9 Hz, 3H); 0.91 (t, J=7.2 Hz, 3H).

Step C:
N,N-diethyl-3-methoxy-2-sulfamoyl-benzamide

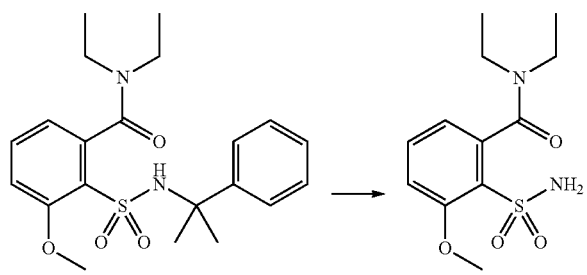 [SMILES: CCN(CC)C(=O)c1cccc(OC)c1S(=O)(=O)NC(C)(C)c1ccccc1 ; CCN(CC)C(=O)c1cccc(OC)c1S(N)(=O)=O]

N,N-diethyl-3-methoxy-2-[(1-methyl-1-phenyl-ethyl)sulfamoyl]benzamide (170.0 mg; 0.42 mmol; 1 eq.) was dissolved into DCM (2 mL) and the mixture was cooled to 0° C. TFA (1 mL) was added and the mixture was stirred at 0° C. The reaction mixture was concentrated under vacuum and co-evaporated 3 times with DCM to give N,N-diethyl-3-methoxy-2-sulfamoyl-benzamide as a white solid used directly in the next step. $^1$H NMR (DMSO-d$_6$, 300 MHz): δ 7.54 (dd, J=8.4 Hz, J=7.5 Hz, 1H); 7.20 (m, 3H); 6.77 (dd, J=1 Hz, J=7.5 Hz, 1H); 3.92 (s, 3H); 3.55 (m, 1H); 3.18 (m, 1H); 3.01 (m, 2H); 1.09 (t, J=6.9 Hz, 3H); 0.95 (t, J=7.2 Hz, 3H).

Step D:
7-methoxy-1,1-dioxo-1,2-benzothiazol-3-one

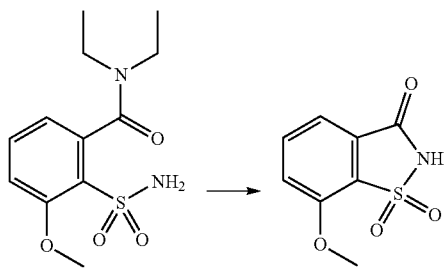 [SMILES: CCN(CC)C(=O)c1cccc(OC)c1S(N)(=O)=O ; COc1cccc2c1S(=O)(=O)NC2=O]

N,N-diethyl-3-methoxy-2-sulfamoyl-benzamide (120.3 mg; 0.42 mmol; 1 eq.) was dissolved into AcOH (2 mL) and heated under reflux for 2 h. AcOH was removed under vacuum and the residue was triturated into aqueous HCl 1N, filtered, washed with water and dried under vacuum at 50° C. The solid was further purified by trituration in heptane to give after drying under vacuum 7-methoxy-1,1-dioxo-1,2-benzothiazol-3-one (50.0 mg; 56%) as a white solid. $^1$H NMR (DMSO-d$_6$, 300 MHz): δ 7.88 (dd, J=7.5 Hz, J=8.4 Hz, 1H); 7.61 (d, J=8.1 Hz, 1H); 7.51 (d, J=7.2 Hz, 1H); 4.01 (s, 3H).

Step E: 3-chloro-7-methoxy-1,2-benzothiazole 1,1-dioxide

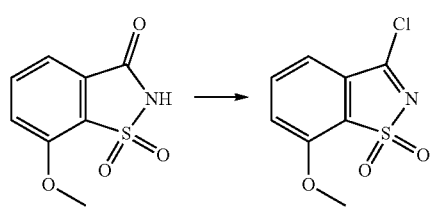

The compound was prepared using the same procedure detailed in example 1 step A starting from 7-methoxy-1,1-dioxo-1,2-benzothiazol-3-one (50.0 mg; 0.23 mmol; 1 eq.) to give 3-chloro-7-methoxy-1,2-benzothiazole 1,1-dioxide (54.0 mg; 99%) as a white powder. $^1$H NMR (DMSO-d$_6$, 300 MHz): δ 7.90 (dd, J=7.5 Hz, J=8.4 Hz, 1H); 7.63 (d, J=8.4 Hz, 1H); 7.52 (d, J=7.5 Hz, 1H); 4.02 (s, 3H).

Step F: 2-methoxy-4-[(E)-[(7-methoxy-1,1-dioxo-1,2-benzothiazol-3-yl)-methyl-hydrazono]methyl]phenol

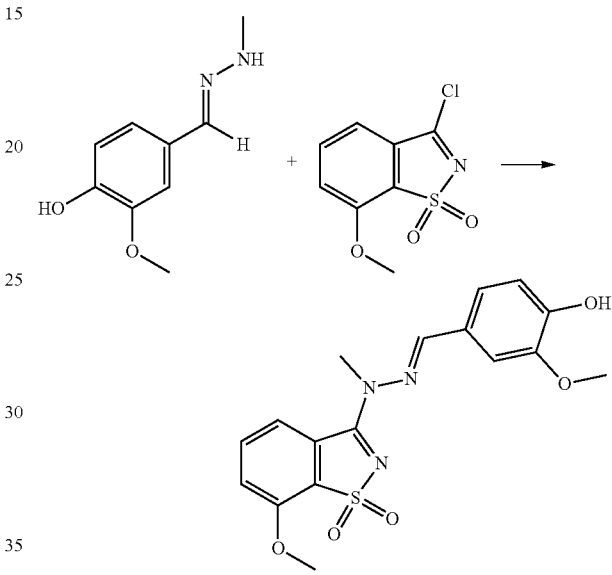

The compound was prepared using the same procedure detailed in example 1 step C starting from 3-chloro-7-methoxy-1,2-benzothiazole 1,1-dioxide (54.0 mg; 0.23 mmol; 1 eq.) and 2-methoxy-4-[(E)-(methylhydrazono)methyl]phenol (example 1, step B, 63.0 mg; 0.35 m mol; 1.5 eq.) giving 2-methoxy-4-[(E)-[(7-methoxy-1,1-dioxo-1,2-benzothiazol-3-yl)-methyl-hydrazono]methyl] phenol (60.0 mg; 68%) as a yellow powder. $^1$H NMR (DMSO-d$_6$, 400 MHz): δ 9.76 (s, 1H); 8.43 (d, J=7.6 Hz, 1H); 8.33 (s, 1H); 7.86 (t, J=8 Hz, 1H); 7.5 (d, J=8.4 Hz, 1H); 7.40 (d, J=2 Hz, 1H); 7.30 (dd, J=2 Hz, J=8 Hz, 1H); 6.94 (d, J=8.4 Hz, 1H); 3.99 (s, 3H); 3.88 (s, 3H); 3.74 (s, 3H). mp >260° C.

Example 22: 4-[(E)-[2-hydroxyethyl-(7-methoxy-1,1-dioxo-1,2-benzothiazol-3-yl) hydrazono]methyl]-2-methoxy-phenol

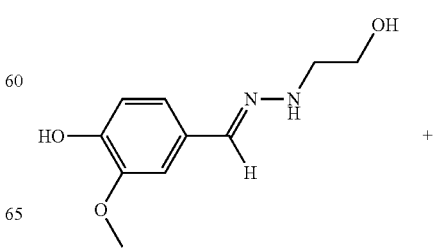

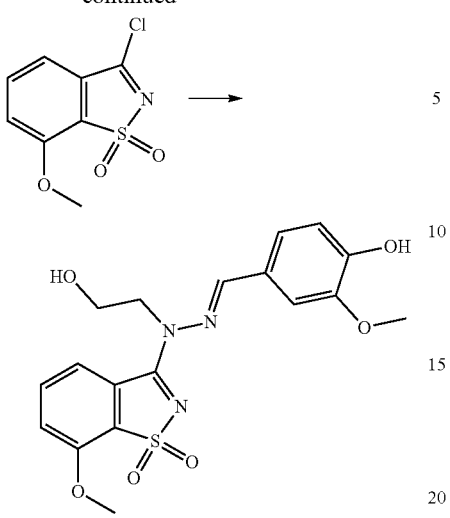

The compound was prepared using the same procedure detailed in example 1 step C starting from 3-chloro-7-methoxy-1,2-benzothiazole 1,1-dioxide (example 21, step E, 100.0 mg; 0.43 mmol; 1 eq.) and 4-[(E)-(2-hydroxyethylhydrazono)methyl]-2-methoxy-phenol (example 2, step A, 136.1 mg; 0.65 mmol; 1.5 eq.) giving 4-[(E)-[2-hydroxyethyl-(7-methoxy-1,1-dioxo-1,2-benzothiazol-3-yl)hydrazono]methyl]-2-methoxy-phenol (123.0 mg; 70%) as a yellow solid. $^1$H NMR (DMSO-d$_6$, 400 MHz): δ 9.83 (s, 1H); 8.57 (s, 1H); 8.38 (d, J=8 Hz, 1H); 7.86 (t, J=8 Hz, 1H); 7.51 (d, J=8 Hz, 1H); 7.40 (d, J=1.6 Hz, 1H); 7.29 (dd, J=1.6 Hz, J=8 Hz, 1H); 6.96 (d, J=8 Hz, 1H); 5.20 (t, J=5.6 Hz, 1H); 4.38 (t, J=6 Hz, 2H); 3.99 (s, 3H); 3.88 (s, 3H); 3.76 (m, 2H). mp >260° C.

Example 23: 2-methoxy-4-[(E)-[(7-methoxy-1,1-dioxo-1,2-benzothiazol-3-yl)-(2-morpholino ethyl)hydrazono]methyl]phenol hydrochloride

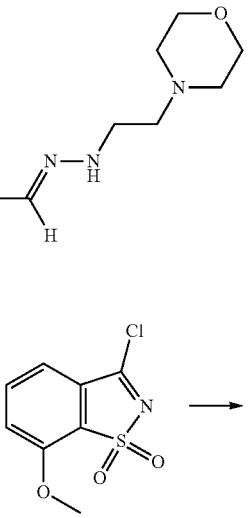

The compound was prepared using the same procedure detailed in example 1 step C starting from 3-chloro-7-methoxy-1,2-benzothiazole 1,1-dioxide (example 21, step E, 100.0 mg; 0.43 mmol; 1 eq.) and 2-methoxy-4-[(E)-(2-morpholinoethylhydrazono)methyl]phenol (example 4, step A 180.9 mg; 0.65 mmol; 1.5 eq.) giving 2-methoxy-4-[(E)-[(7-methoxy-1,1-dioxo-1,2-benzothiazol-3-yl)-(2-morpholinoethyl)hydrazono]methyl]phenol hydrochloride (105.0 mg; 45%) as a pale yellow powder. $^1$H NMR (DMSO-d$_6$, 400 MHz): δ 11.83 (s broad, 1H); 9.87 (s, 1H); 8.82 (s, 1H); 8.41 (d, J=7.6 Hz, 1H); 7.90 (t, J=8 Hz, 1H); 7.54 (m, 2H); 7.42 (d, J=8 Hz, 1H); 6.98 (d, J=8 Hz, 1H); 4.76 (m, 2H); 4.00 (s, 3H); 3.97 (m, 2H); 3.87 (s, 3H); 3.84 (m, 2H); 3.47 (m, 6H). mp >260° C.

Example 24: 2-methoxy-4-[(E)-[(7-methoxy-1,1-dioxo-1,2-benzothiazol-3-yl)-(2-methoxy ethyl)hydrazono]methyl]phenol

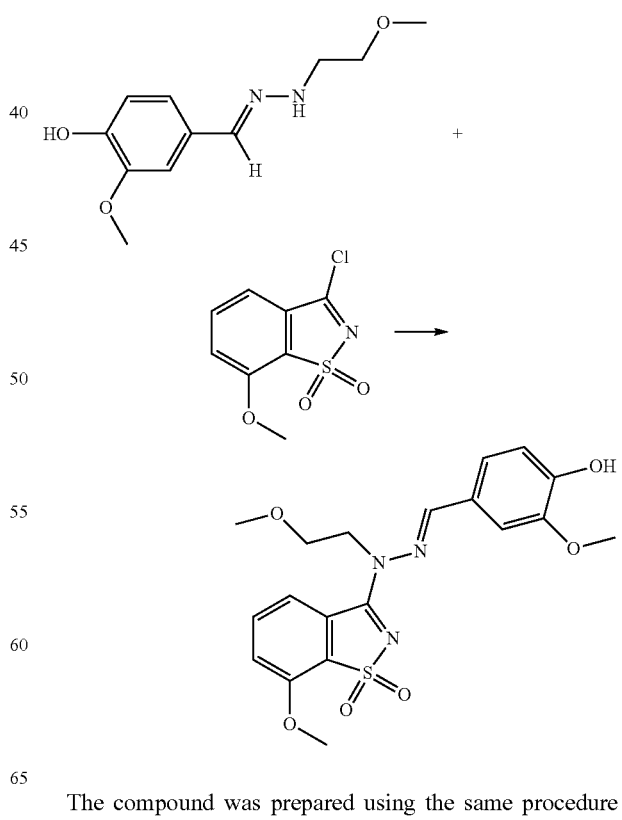

The compound was prepared using the same procedure detailed in example 1 step C starting from 3-chloro-7- methoxy-1,2-benzothiazole 1,1-dioxide (example 21, step E, 150.0 mg; 0.65 mmol; 1 eq.) and 2-methoxy-4-[(E)-(2-methoxyethylhydrazono)methyl]phenol (example 7, step A, 159.7 mg; 0.71 mmol; 1.1 eq.) giving 2-methoxy-4-[(E)-[(7-methoxy-1,1-dioxo-1,2-benzothiazol-3-yl)-(2-methoxy-ethyl)hydrazono]methyl]phenol (91.9 mg; 33%) as pale yellow solid. $^1$H NMR (DMSO-$d_6$, 400 MHz): δ 9.77 (s, 1H); 8.46 (s, 1H); 8.37 (d, J=8 Hz, 1H); 7.86 (t, J=8 Hz, 1H); 7.51 (d, J=8.4 Hz, 1H); 7.39 (d, J=2 Hz, 1H); 7.28 (dd, J=2 Hz, J=8.4 Hz, 1H); 6.93 (d, J=8 Hz, 1H); 4.51 (t, J=5.6 Hz, 2H); 3.99 (s, 3H); 3.88 (s, 3H); 3.70 (t, J=5.6 Hz, 2H); 3.29 (s, 3H). mp: 225-227° C.

Example 25: 2-methoxy-4-[(E)-[methyl-(5-methyl-1,1-dioxo-1,2-benzothiazol-3-yl)hydrazono] methyl] phenol Step A: 4-methyl-N-(1-methyl-1-phenyl-ethyl)benzenesulfonamide

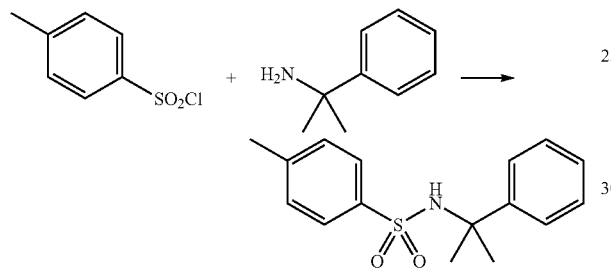

The compound was prepared using the same procedure detailed in example 21 step A starting from cumylamine (4.53 mL; 0.03 mol; 1.2 eq.) and 4-toluenesulfonyl chloride (5.00 g; 0.03 mol; 1 eq.) to give 4-methyl-N-(1-methyl-1-phenyl-ethyl)benzenesulfonamide (5.00 g; 66%) as a white powder. $^1$H NMR (DMSO-$d_6$, 300 MHz): δ 7.98 (s, 1H); 7.49 (d, J=8.1 Hz, 2H); 7.31 (dd, J=1.2 Hz, J=7.8 Hz, 2H); 7.15 (m, 5H); 2.34 (s, 3H); 1.44 (s, 6H).

Step B: N,N-diethyl-5-methyl-2-[(1-methyl-1-phenyl-ethyl)sulfamoyl]benzamide

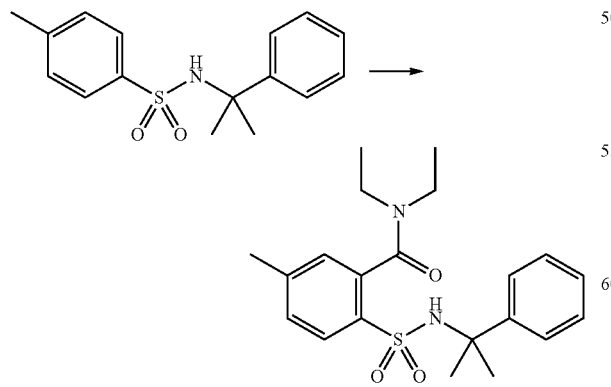

The compound was prepared using the same procedure detailed in example 21 step B starting from 4-methyl-N-(1-methyl-1-phenyl-ethyl)benzenesulfonamide (5.00 g; 17.28 mmol; 1 eq.) to give N,N-diethyl-5-methyl-2-[(1-methyl-1-phenyl-ethyl)sulfamoyl]benzamide (3.93 g; 58%) as a colorless gum. $^1$H NMR (CDCl$_3$, 300 MHz): δ 7.29 (dd, J=2.1 Hz, J=8.4 Hz, 2H); 7.01 (m, 5H); 6.83 (m, 1H): 6.21 (s, 1H); 3.59 (m, 1H); 3.49 (m, 1H); 3.13 (m, 2H); 2.36 (s, 3H); 1.79 (s, 3H); 1.56 (s, 3H); 1.28 (t, J=7.2 Hz, 3H); 1.08 (t, J=7.2 Hz, 3H).

Step C: N,N-diethyl-5-methyl-2-sulfamoyl-benzamide

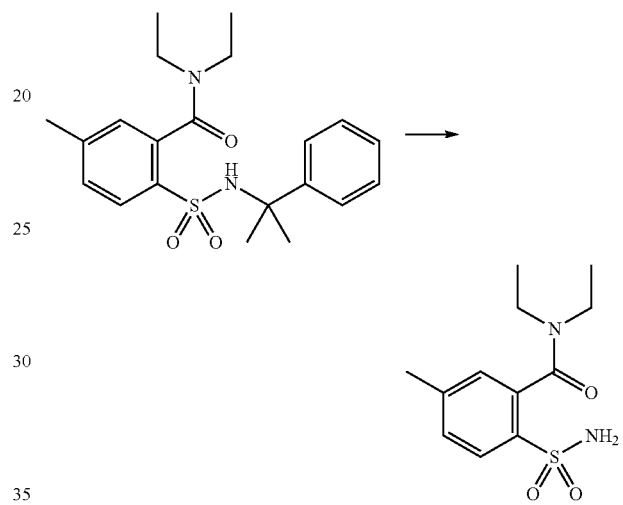

The compound was prepared using the same procedure detailed in example 21 step C starting from N,N-diethyl-5-methyl-2-[(1-methyl-1-phenyl-ethyl)sulfamoyl]benzamide (4.20 g; 10.81 mmol; 1 eq.) to give N,N-diethyl-5-methyl-2-sulfamoyl-benzamide (2.92 g; 99%) as a colorless oil used without further purification in the next step.

Step D: 5-methyl-1,1-dioxo-1,2-benzothiazol-3-one

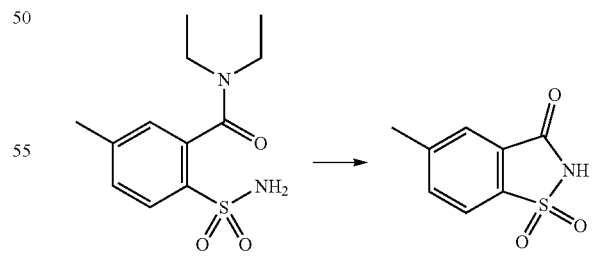

The compound was prepared using the same procedure detailed in example 21 step D starting from N,N-diethyl-5-methyl-2-sulfamoyl-benzamide (2.92 g; 10.81 mmol; 1 eq.) to give 5-methyl-1,1-dioxo-1,2-benzothiazol-3-one (1.54 g; 72%) as a white powder. $^1$H NMR (DMSO-$d_6$, 300 MHz): δ 8.04 (d, J=7.8 Hz, 1H); 7.82 (m, 2H); 2.50 (s, 3H).

Step E: 3-chloro-5-methyl-1,2-benzothiazole 1,1-dioxide

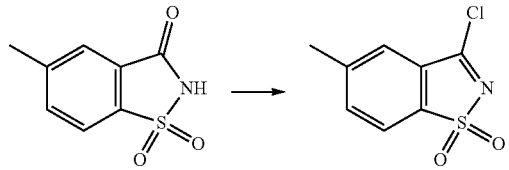

The compound was prepared using the same procedure detailed in example 1 step A starting from 5-methyl-1,1-dioxo-1,2-benzothiazol-3-one (1.54 g; 0.01 mol; 1 eq.) to give 3-chloro-5-methyl-1,2-benzothiazole 1,1-dioxide (1.54 g; 91%) as a white powder used without further purification in the next step.

Step F: 2-methoxy-4-[(E)-[methyl-(5-methyl-1,1-dioxo-1,2-benzothiazol-3-yl)hydrazono]methyl]phenol

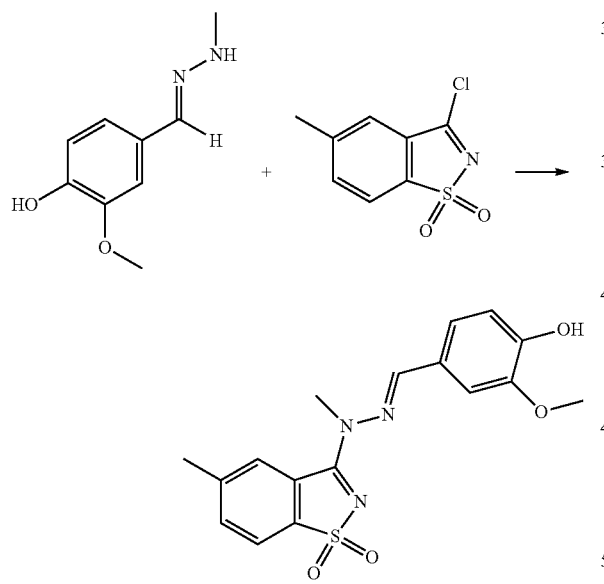

The compound was prepared using the same procedure detailed in example 1 step C starting from 3-chloro-5-methyl-1,2-benzothiazole 1,1-dioxide (185.5 mg; 0.86 mmol; 1 eq.) and 2-methoxy-4-[(E)-(methylhydrazono)methyl]phenol (example 1, step B, (232.5 mg; 1.29 mmol; 1.5 eq.) giving 2-methoxy-4-[(E)-[methyl-(5-methyl-1,1-dioxo-1,2-benzothiazol-3-yl)hydrazono] methyl]phenol (60.0 mg; 19%) as a yellow powder. $^1$H NMR (DMSO-d$_6$, 400 MHz): δ 9.78 (s, 1H); 8.76 (s, 1H); 8.36 (s, 1H); 7.94 (d, J=7.6 Hz, 1H); 7.70 (dd, J=1.6 Hz, J=7.6 Hz, 1H); 7.45 (d, J=1.6 Hz, 1H); 7.28 (dd, J=2. Hz, J=8 Hz, 1H); 6.95 (d, J=8 Hz, 1H); 3.92 (s, 3H); 3.77 (s, 3H); 2.53 (s, 3H). mp: 253° C.

Example 26: 2-methoxy-4-[(E)-[(5-methyl-1,1-dioxo-1,2-benzothiazol-3-yl)-(2-morpholino ethyl)hydrazono]methyl]phenol hydrochloride

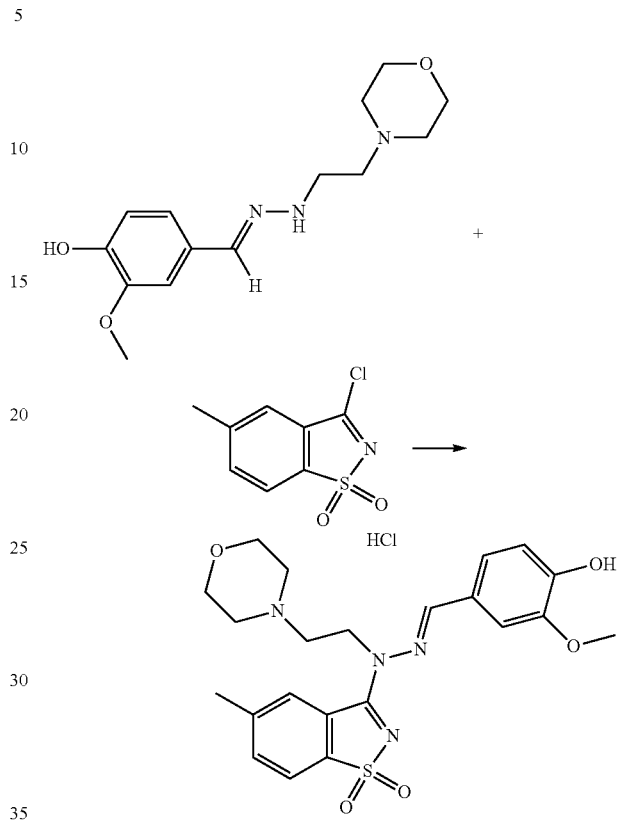

The compound was prepared using the same procedure detailed in example 1 step C starting from 3-chloro-5-methyl-1,2-benzothiazole 1,1-dioxide (example 25, step E, 175.0 mg; 0.81 mmol; 1 eq.) and 2-methoxy-4-[(E)-(2-morpholinoethylhydrazono)methyl]phenol (example 4, step A, 340.0 mg; 1.22 mmol; 1.5 eq.) giving 2-methoxy-4-[(E)-[(5-methyl-1,1-dioxo-1,2-benzothiazol-3-yl)-(2-morpholinoethyl)hydrazono]methyl]phenol hydrochloride (56.0 mg; 14%) as a yellow powder. $^1$H NMR (DMSO-d$_6$, 400 MHz): δ 11.15 (s broad, 1H); 9.86 (s, 1H); 8.72 (m, 2H); 7.97 (d, J=8 Hz, 1H); 7.72 (d, J=7.6 Hz, 1H); 7.49 (d, J=2 Hz, 1H); 7.39 (m, 1H); 6.97 (d, J=8 Hz, 1H); 4.78 (m, 2H); 4.10 (m, 2H); 3.91 (s, 3H); 3.77 (m, 2H); 3.50 (m, 6H); 2.54 (s, 3H). mp >260° C.

Example 27: 4-[(E)-[2-hydroxyethyl-(5-methyl-1,1-dioxo-1,2-benzothiazol-3-yl)hydrazono] methyl]-2-methoxy-phenol

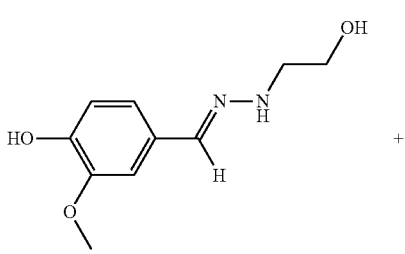

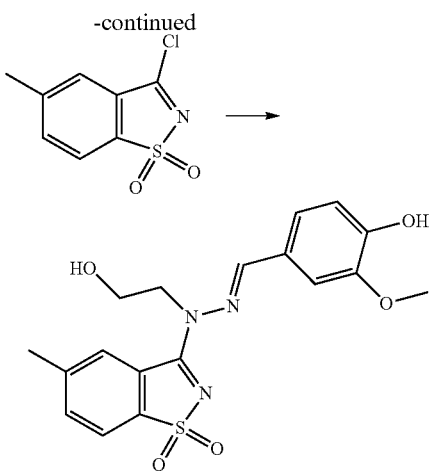

The compound was prepared using the same procedure detailed in example 1 step C starting from 3-chloro-5-methyl-1,2-benzothiazole 1,1-dioxide (example 25, step E, 150.0 mg; 0.70 mmol; 1 eq.) and 4-[(E)-(2-hydroxyethyl-hydrazono)methyl]-2-methoxy-phenol (example 2, step A, 160.9 mg; 0.77 mmol; 1.1 eq.) giving 4-[(E)-[2-hydroxy-ethyl-(5-methyl-1,1-dioxo-1,2-benzothiazol-3-yl)hydrazono]methyl]-2-methoxy-phenol (17.6 mg; 6%) as a yellow solid. $^1$H NMR (DMSO-d$_6$, 400 MHz): δ 9.81 (s, 1H); 8.69 (d, J=1.6 Hz, 1H); 8.57 (s, 1H); 7.94 (d, J=8.4 Hz, 1H); 7.69 (dd, J=1.6 Hz, J=8 Hz, 1H); 7.44 (d, J=2 Hz, 1H); 7.27 (dd, J=2 Hz, J=8 Hz, 1H); 6.96 (d, J=8 Hz, 1H); 5.14 (t, J=5.6 Hz, 1H); 4.42 (t, J=5.6 Hz, 2H); 3.91 (s, 3H); 3.77 (m, 2H); 2.52 (s, 3H).

Example 28: 2-methoxy-4-[(E)-[2-methoxyethyl-(5-methyl-1,1-dioxo-1,2-benzothiazol-3-yl) hydrazono]methyl]phenol

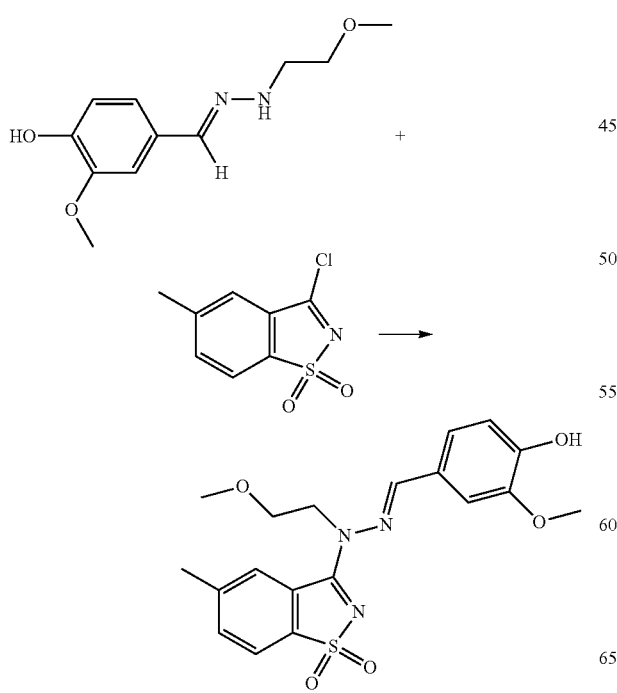

The compound was prepared using the same procedure detailed in example 1 step C starting from 3-chloro-5-methyl-1,2-benzothiazole 1,1-dioxide (example 25, step E, 130.0 mg; 0.60 mmol; 1 eq.) and 2-methoxy-4-[(E)-(2-methoxyethylhydrazono)methyl]phenol (example 7, step A, 148.7 mg; 0.66 mmol; 1.1 eq.) giving 2-methoxy-4-[(E)-[2-methoxyethyl-(5-methyl-1,1-dioxo-1,2-benzothiazol-3-yl) hydrazono]methyl]phenol (40.9 mg; 16%) as pale yellow solid. $^1$H NMR (DMSO-de, 400 MHz): δ 9.79 (s, 1H); 8.70 (s, 1H); 8.49 (s, 1H); 7.94 (d, J=7.6 Hz, 1H); 7.69 (d, J=7.6 Hz, 1H); 7.44 (d, J=1.6 Hz, 1H); 7.27 (dd, J=2 Hz, J=8 Hz, 1H); 6.94 (d, J=8.4 Hz, 1H); 4.55 (t, J=5.6 Hz, 2H); 3.91 (s, 3H); 3.70 (t, J=5.6 Hz, 2H); 3.29 (s, 3H); 2.50 (s, 3H).

Example 29: 4-[(E)-[2-hydroxyethyl-(7-methoxy-5-methy-1,1-dioxo-1,2-benzothiazol-3-yl) hydrazono] methyl]-2-methoxy-phenol Step A:
5-bromo-2-methoxy-4-methyl-benzenesulfonate

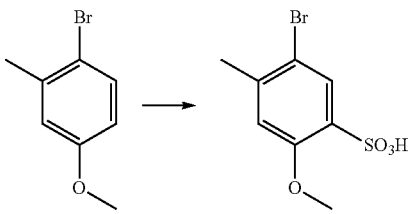

2-bromo-5-methoxytoluene (14.25 mL; 0.10 mol; 1 eq.) was cautiously added dropwise over a period of 10 minutes to sulfuric acid (42 mL; 0.79 mol; 7.83 eq.) at room temperature (exothermic, temperature rise from 20° C. to 40° C.). and the reaction mixture was stirred for 16 hours. The reaction mixture was poured carefully onto 1 liter of cold water. The water was removed under vacuum, then the residue was triturated with cyclohexane, filtered, washed with EtOAc and Et$_2$O and dried under vacuum to give 5-bromo-2-methoxy-4-methyl-benzenesulfonate (24.50 g; 87%) as a white powder. $^1$H NMR (DMSO-d$_6$, 300 MHz): δ 7.70 (s, 1H); 6.99 (s, 1H); 3.74 (s, 3H); 2.32 (s, 3H).

Step B: 2-methoxy-4-methyl-benzenesulfonate

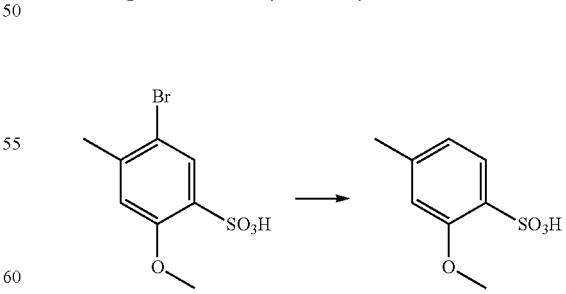

5-bromo-2-methoxy-4-methyl-benzenesulfonate (24.50 g; 87.15 mmol; 1 eq.) was dissolved into MeOH (250 mL) in a Parr reactor. Pd/C 10% (50% wet, 2.50 g; 11.75 mmol; 0.13 eq.) was added and mixture was stirred at 60° C. under hydrogen pressure (70 psi) for 7 h. The reaction mixture was filtered over Whatman and concentrated to dryness (orange solid). The crude product was slurred in DCM and cooled to 0° C. The precipitate was filtered and washed by DCM to give 2-methoxy-4-methyl-benzenesulfonate (13.56 g; 77%) as a white powder. ¹H NMR (DMSO-d₆, 300 MHz): δ 7.54 (d, J=7.8 Hz, 1H); 6.89 (s, 1H); 6.67 (dd, J=0.6 Hz, J=7.8 Hz, 1H); 3.74 (s, 3H); 2.29 (s, 3H).

Step C: 2-methoxy-4-methyl-benzenesulfonyl chloride

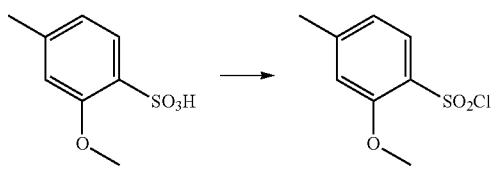

Thionyl chloride (34 mL; 468.69 mmol; 6.99 eq.) was cautiously added to 2-methoxy-4-methyl-benzenesulfonate (13.56 g; 67.05 mmol; 1 eq.) over a period of 10 minutes. The reaction mixture was then stirred under reflux for 2 hours. Excess of thionyl chloride was removed by evaporation under reduced pressure and the residue was partitioned between water and DCM. The aqueous layer was then extracted with DCM. The combined organic layers were evaporated to dryness to give 2-methoxy-4-methyl-benzenesulfonyl chloride (5.60 g; 36%) as a yellow oil which crystallized (product used in the next step without further purification). ¹H NMR (DMSO-d₆, 300 MHz): δ 7.54 (d, J=7.8 Hz, 1H); 6.81 (s, 1H); 6.67 (dd, J=0.9 Hz, J=7.8 Hz, 1H); 3.73 (s, 3H); 2.28 (s, 3H).

Step D: 2-methoxy-4-methyl-N-(1-methyl-1-phenyl-ethyl)benzenesulfonamide

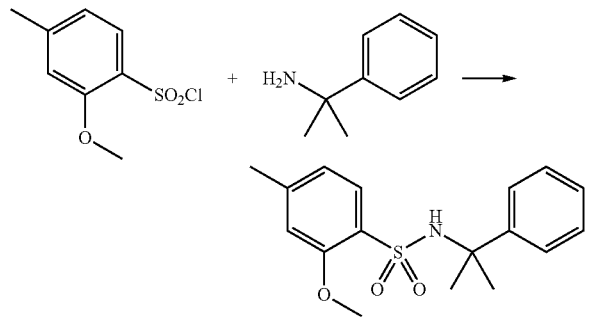

The compound was prepared using the same procedure detailed in example 21 step A starting from cumylamine (4.38 mL; 0.03 mol; 1.2 eq.) and 2-methoxy-4-methyl-benzenesulfonyl chloride (5.60 g; 0.03 mol; 1 eq.) to give 2-methoxy-4-methyl-N-(1-methyl-1-phenyl-ethyl) benzenesulfonamide (4.77 g; 59%) as a white powder. ¹H NMR (DMSO-d₆, 300 MHz): δ7.44 (s, 1H); 7.40 (d, J=7.5 Hz, 1H); 7.33 (dd, J=1.2 Hz, J=8.1 Hz, 2H); 7.15 (m, 3H); 6.88 (s, 1H); 6.77 (m, 1H); 3.85 (s, 3H); 2.33 (s, 3H); 1.41 (s, 6H).

Step E: N,N-diethyl-3-methoxy-5-methyl-2-[(1-methyl-1-phenyl-ethyl)sulfamoyl]benzamide

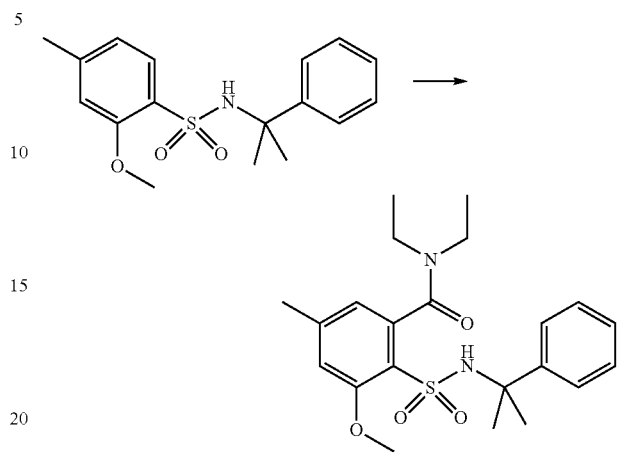

The compound was prepared using the same procedure detailed in example 21 step B starting from 2-methoxy-4-methyl-N-(1-methyl-1-phenyl-ethyl)benzenesulfonamide (4.77 g; 0.01 mol; 1 eq.) to give N,N-diethyl-3-methoxy-5-methyl-2-[(1-methyl-1-phenyl-ethyl)sulfamoyl]benzamide (0.73 g; 12%) as a white powder. ¹H NMR (DMSO-d₆, 300 MHz): δ 7.37 (m, 2H); 7.32 (s, 1H); 7.13 (m, 3H); 6.86 (s, 1H); 6.53 (s, 1H); 3.84 (s, 3H); 3.43 (m, 1H); 3.24 (m, 1H); 2.92 (m, 2H); 2.32 (s, 3H); 1.48 (s, 3H); 1.42 (s, 3H); 1.05 (t, J=7.2 Hz, 3H); 0.92 (t, J=7.2 Hz, 3H).

Step F: N,N-diethyl-3-methoxy-5-methyl-2-sulfamoyl-benzamide

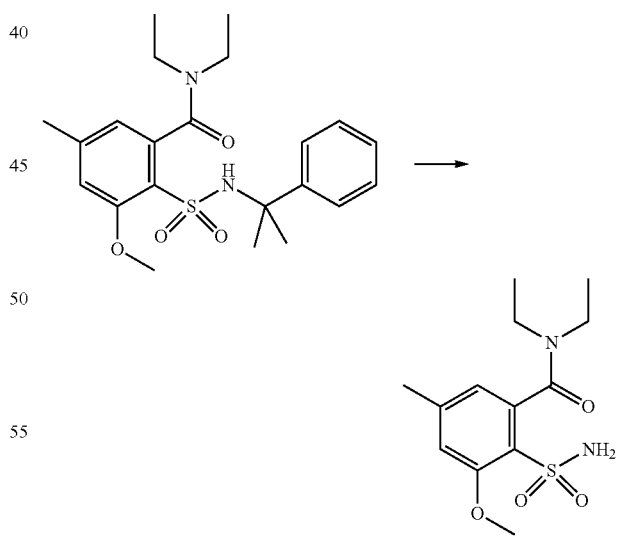

The compound was prepared using the same procedure detailed in example 21 step C starting from N,N-diethyl-3-methoxy-5-methyl-2-[(1-methyl-1-phenyl-ethyl)sulfamoyl] benzamide (730.0 mg; 1.74 mmol; 1 eq.) to give N,N-diethyl-3-methoxy-5-methyl-2-sulfamoyl-benzamide (523.0 mg; 99%) as a white syrup, used directly in the next step without further purification.

Step G: 7-methoxy-5-methyl-1,1-dioxo-1,2-benzo-thiazol-3-one

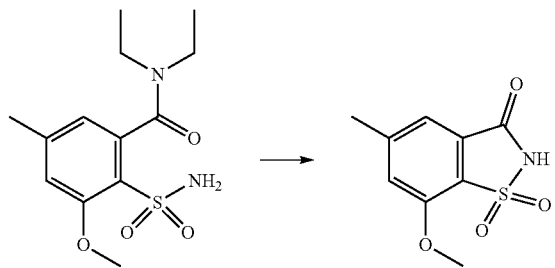 [SMILES: CCN(CC)C(=O)c1cc(C)cc(OC)c1S(N)(=O)=O ; COc1cc(C)cc2c1S(=O)(=O)NC2=O]

The compound was prepared using the same procedure detailed in example 21 step D starting N,N-diethyl-3-methoxy-5-methyl-2-sulfamoyl-benzamide (523.0 mg; 1.74 mmol; 1 eq.) to give 7-methoxy-5-methyl-1,1-dioxo-1,2-benzothiazol-3-one (360.0 mg; 91%) as a white powder. $^1$H NMR (DMSO-d$_6$, 300 MHz): δ 7.46 (s, 1H); 7.35 (s, 1H); 3.99 (s, 3H); 2.48 (s, 3H).

Step H: 3-chloro-7-methoxy-5-methyl-1,2-benzothiazole 1,1-dioxide

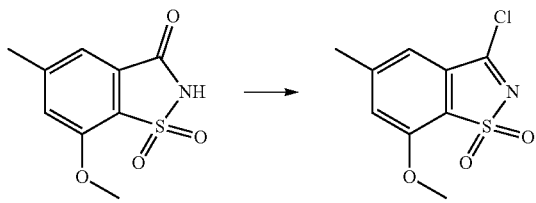

The compound was prepared using the same procedure detailed in example 1 step A starting from 7-methoxy-5-methyl-1,1-dioxo-1,2-benzothiazol-3-one (360.0 mg; 1.58 mmol; 1 eq.) to give 3-chloro-7-methoxy-5-methyl-1,2-benzothiazole 1,1-dioxide (380.0 mg; 98%) as a white powder used directly in the next step without further purification.

Step I: 4-[(E)-[2-hydroxyethyl-(7-methoxy-5-methyl-1,1-dioxo-1,2-benzothiazol-3-yl) hydrazono]methyl]-2-methoxy-phenol

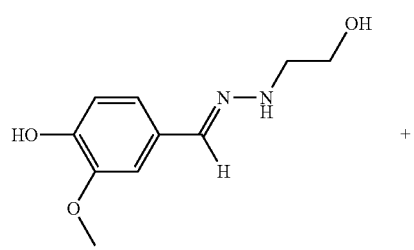

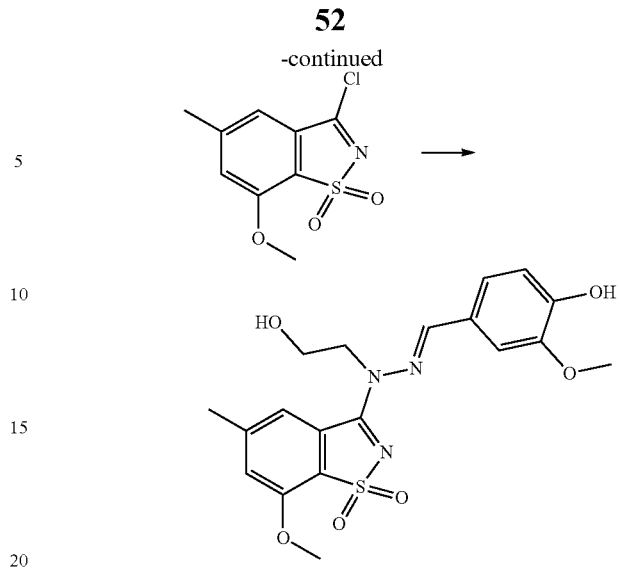

The compound was prepared using the same procedure detailed in example 1 step C starting from 3-chloro-7-methoxy-5-methyl-1,2-benzothiazole 1,1-dioxide (50.0 mg; 0.20 mmol; 1 eq.) and 4-[(E)-(2-hydroxyethylhydrazono)methyl]-2-methoxy-phenol (example 2, step A, 64.2 mg; 0.31 mmol; 1.5 eq.) giving 4-[(E)-[2-hydroxyethyl-(7-methoxy-5-methyl-1,1-dioxo-1,2-benzothiazol-3-yl)hydrazono]methyl]-2-methoxy-phenol (76.0 mg; 89%) as a yellow powder. $^1$H NMR (DMSO-d$_6$, 400 MHz): δ 9.79 (s, 1H); 8.53 (s, 1H); 8.24 (s, 1H); 7.41 (d, J=1.6 Hz, 1H); 7.37 (s, 1H); 7.25 (dd, J=2 Hz, J=7.6 Hz, 1H); 6.94 (d, J=8 Hz, 1H); 5.13 (t, J=5.6 Hz, 1H); 4.38 (t, J=5.6 Hz, 2H); 3.97 (s, 3H); 3.90 (s, 3H); 3.74 (m, 2H); 2.50 (s, 3H).

Example 30: 2-methoxy-4-[(E)-[2-methoxyethyl-(7-methoxy-5-methyl-1,1-dioxo-1,2-benzothiazol-3-yl)hydrazono]methyl]phenol

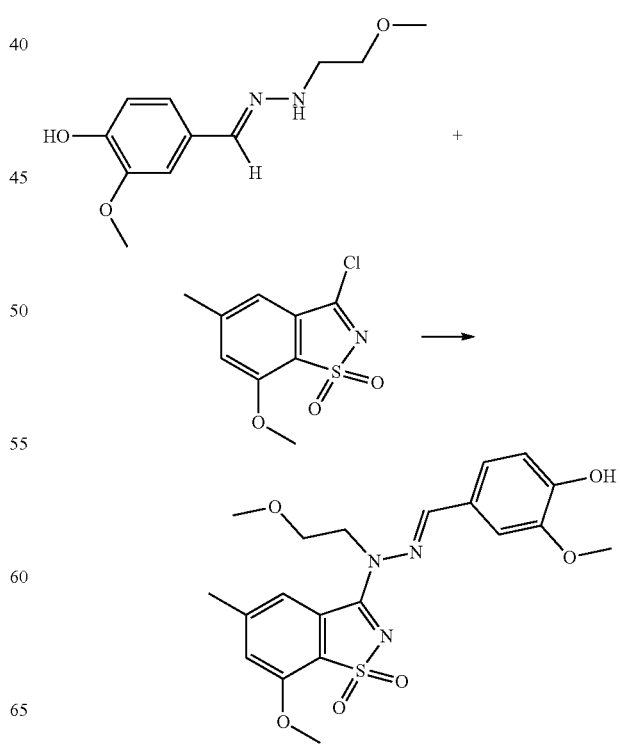

The compound was prepared using the same procedure detailed in example 1 step C starting from 3-chloro-7-methoxy-5-methyl-1,2-benzothiazole 1,1-dioxide (example 29, step H, 50.0 mg; 0.20 mmol; 1 eq.) and 2-methoxy-4-[(E)-(3-morpholinopropylhydrazono) methyl]phenol (example 13, step A, 68.5 mg; 0.31 mmol; 1.5 eq.) giving, 2-methoxy-4-[(E)-[2-methoxyethyl-(7-methoxy-5-methyl-1,1-dioxo-1,2-benzothiazol-3-yl)hydrazono]methyl] phenol (58.0 mg; 64%) as a yellow powder. $^1$H NMR (DMSO-$d_6$, 400 MHz): δ 9.77 (s, 1H); 8.45 (s, 1H); 8.24 (s, 1H); 7.41 (d, J=2 Hz, 1H); 7.37 (s, 1H); 7.25 (dd, J=2 Hz, J=8 Hz, 1H); 6.93 (d, J=8 Hz, 1H); 4.51 (t, J=5.6 Hz, 2H); 3.98 (s, 3H); 3.87 (s, 3H); 3.69 (t, J=5.6 Hz, 2H); 3.29 (s, 3H); 2.50 (s, 3H). mp: 261° C.

Example 31: 2-methoxy-4-[(E)-[(7-methoxy-5-methyl-1,1-dioxo-1,2-benzothiazol-3-yl)-methyl-hydrazono]methyl]phenol

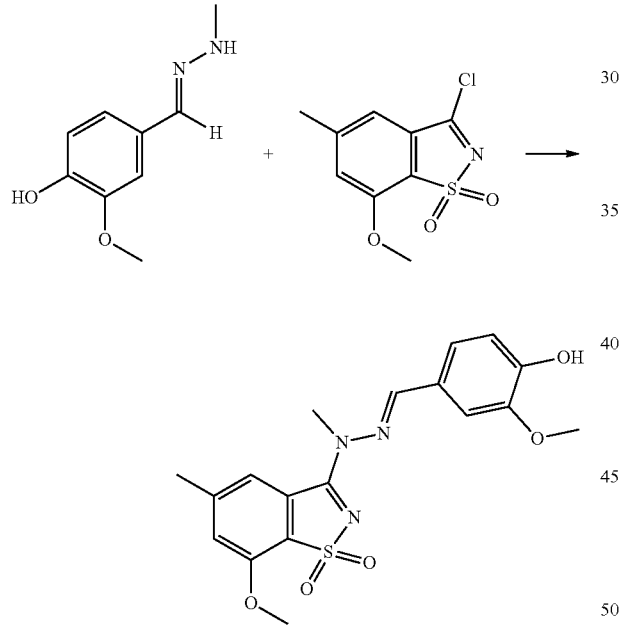

The compound was prepared using the same procedure detailed in example 1 step C starting from 3-chloro-7-methoxy-5-methyl-1,2-benzothiazole 1,1-dioxide (example 29, step H, 50.0 mg; 0.20 mmol; 1 eq.) and 2-methoxy-4-[(E)-(methylhydrazono)methyl]phenol (example 1, step B, 55.0 mg; 0.31 mmol; 1.5 eq.) giving 2-methoxy-4-[(E)-[(7-methoxy-5-methyl-1,1-dioxo-1,2-benzothiazol-3-yl)-methyl-hydrazono]methyl]phenol (57.0 mg; 72%) as a yellow powder. $^1$H NMR (DMSO-$d_6$, 400 MHz): δ 9.76 (s, 1H); 8.32 (s, 1H); 8.30 (s, 1H); 7.41 (d, J=2 Hz, 1H); 7.36 (s, 1H); 7.26 (dd, J=2 Hz, J=8 Hz, 1H); 6.94 (d, J=8 Hz, 1H); 3.95 (s, 3H); 3.93 (s, 3H); 3.73 (s, 3H); 2.50 (s, 3H).

Example 32: 2-methoxy-4-[(E)-[(7-methoxy-5-methyl-1,1-dioxo-1,2-benzothiazol-3-yl)-(2-morpholinoethyl)hydrazono]methyl]phenol hydrochloride

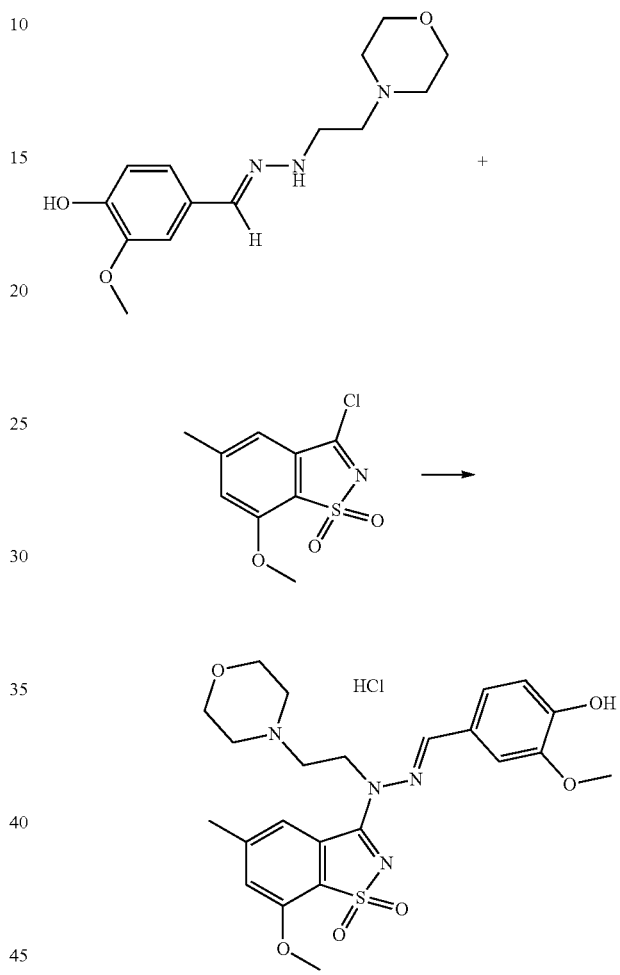

The compound was prepared using the same procedure detailed in example 1 step C starting from 3-chloro-7-methoxy-5-methyl-1,2-benzothiazole 1,1-dioxide (example 29, step H, 50.0 mg; 0.20 mmol; 1 eq.) and 2-methoxy-4-[(E)-(2-morpholinoethyl hydrazono)methyl]phenol (example 4, step A, 94.8 mg; 0.31 mmol; 1.5 eq.) giving 2-methoxy-4-[(E)-[(7-methoxy-5-methyl-1,1-dioxo-1,2-benzothiazol-3-yl)-(2-morpholinoethyl) hydrazono]methyl] phenol hydrochloride (60.0 mg; 54%) as a yellow powder. $^1$H NMR (DMSO-$d_6$, 400 MHz): δ 10.97 (s, broad, 1H); 9.84 (s, 1H); 8.64 (s, 1H); 8.26 (s, 1H); 7.46 (d, J=1.6 Hz, 1H); 7.41 (s, 1H); 7.39 (d, J=8 Hz, 1H); 6.96 (d, J=8 Hz, 1H); 4.75 (m, 2H); 4.08 (m, 2H); 3.98 (s, 3H); 3.90 (s, 3H); 3.72 (m, 2H); 3.62 (m, 2H); 3.49 (m, 2H); 3.26 (m, 2H); 2.52 (s, 3H).

Example 33: 2-methoxy-4-[(E)-[methyl-(6-methyl-1,1-dioxo-1,2-benzothiazol-3-yl)hydrazono] methyl] phenol Step A: 6-methyl-1,1-dioxo-1,2-benzothiazol-3-one

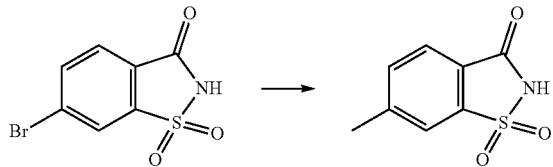

PdCl$_2$(dppf).DCM complex (38.9 mg; 0.05 mmol; 0.05 eq.) and trimethylboroxine (199 µL; 1.43 mmol; 1.5 eq.) were added to a solution of 6-bromosaccharine (250.0 mg; 0.95 mmol; 1 eq.) in ethylene glycol dimethyl ether (2.5 mL) under Argon. A solution of K$_2$CO$_3$ (197.8 mg; 1.43 mmol; 1.50 eq.) in water (1 mL) was then added and the reaction was stirred 15 minutes at 120° C. under MW irradiation. The mixture was filtered over Whatman. The filtrate was concentrated under reduced pressure. Water was added and the mixture was extracted twice with EtOAc. Then aqueous layer was acidified with HCl 1N and extracted twice with EtOAc. Organic layers were combined, dried over MgSO$_4$, filtered and concentrated under reduced pressure to give 6-methyl-1,1-dioxo-1,2-benzothiazol-3-one (156.0 mg; 79%) as a pale yellow powder, used directly in the next step without further purification. $^1$H NMR (DMSO-d$_6$, 300 MHz): δ 8.03 (d, J=7.8 Hz, 1H); 7.82 (d, J=0.6 Hz, 1H); 7.79 (dd, J=0.6 Hz, J=7.5 Hz, 1H); 2.50 (s, 3H).

Step B: 3-chloro-6-methyl-1,2-benzothiazole 1,1-dioxide

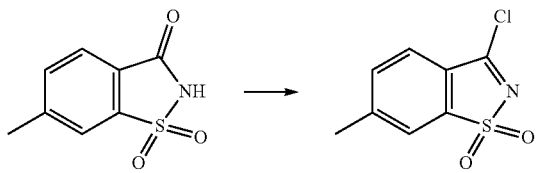

The compound was prepared using the same procedure detailed in example 1 step A starting from 6-methyl-1,1-dioxo-1,2-benzothiazol-3-one (150.0 mg; 0.76 mmol; 1 eq.) to give 3-chloro-6-methyl-1,2-benzothiazole 1,1-dioxide (177.0 mg; quant.) as a brown oil, used without further purification in the next step. $^1$H NMR (DMSO-d$_6$, 300 MHz): δ 8.05 (d, J=8.1 Hz, 1H); 7.84 (d, J=0.9 Hz, 1H); 7.82 (dd, J=0.9 Hz, J=8.1 Hz, 1H); 2.50 (s, 3H).

Step C: 2-methoxy-4-[(E)-[methyl-(6-methyl-1,1-dioxo-1,2-benzothiazol-3-yl)hydrazono]methyl] phenol

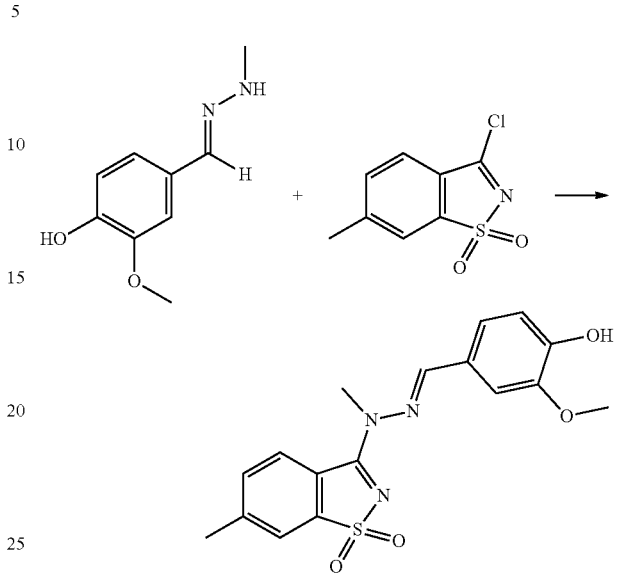

The compound was prepared using the same procedure detailed in example 1 step C starting from 3-chloro-6-methyl-1,2-benzothiazole 1,1-dioxide (164.0 mg; 0.76 mmol; 1 eq.) and 2-methoxy-4-[(E)-(methylhydrazono) methyl]phenol (example 1, step B, 205.6 mg; 1.14 mmol; 1.5 eq.) giving 2-methoxy-4-[(E)-[methyl-(6-methyl-1,1-dioxo-1,2-benzothiazol-3-yl)hydrazono] methyl]phenol (72.0 mg; 24%) as a brown powder. $^1$H NMR (DMSO-d$_6$, 400 MHz): δ 9.78 (s, 1H); 8.76 (s, 1H); 8.36 (s, 1H); 7.94 (d, J=8 Hz, 1H); 7.69 (d, J=8 Hz, 1H); 7.45 (s, 1H); 7.28 (d, J=8 Hz, 1H); 6.94 (d, J=8 Hz, 1H); 3.92 (s, 3H); 3.77 (s, 3H); 2.53 (s, 3H).

Example 34: 3-[[(E)-(4-hydroxy-3-methoxy-phenyl)methyleneamino]-methyl-amino]-1,1-dioxo-1,2-benzothiazole-6-carboxylic acid Step A: methyl 3-[[(E)-(4-hydroxy-3-methoxy-phenyl)methyleneamino]-methyl-amino]-1,1-dioxo-1,2-benzothiazole-6-carboxylate

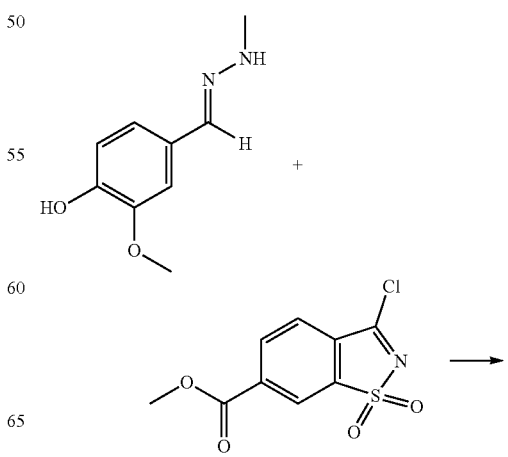

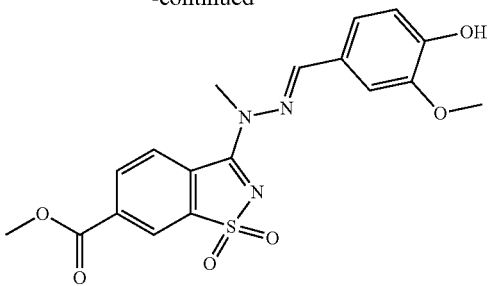

The compound was prepared using the same procedure detailed in example 1 step C starting from methyl 3-chloro-1,1-dioxo-1$\lambda^6$,2-benzothiazole-6-carboxylate (250.0 mg; 0.96 mmol; 1 eq.) and 2-methoxy-4-[(E)-(methylhydrazono)methyl]phenol (example 1, step B, 346.9 mg; 1.93 mmol; 2 eq.) giving methyl 3-[[(E)-(4-hydroxy-3-methoxy-phenyl)methyleneamino]-methyl-amino]-1,1-dioxo-1,2-benzothiazole-6-carboxylate (274.3 mg; 71%) as yellow solid. $^1$H NMR (DMSO-d$_6$, 300 MHz): δ 9.80 (s, 1H); 9.02 (d, J=8.1 Hz, 1H); 8.46 (dd, J=1.5 Hz, J=8.1 Hz, 1H); 8.40 (s, 2H); 7.41 (s, 1H); 7.36 (d, J=8.1 Hz, 1H); 6.94 (d, J=8.1 Hz, 1H); 3.95 (s, 3H); 3.90 (s, 3H); 3.79 (s, 3H).

Step B: 3-[[(E)-(4-hydroxy-3-methoxy-phenyl)methyleneamino]-methyl-amino]-1,1-dioxo-1,2-benzothiazole-6-carboxylic acid

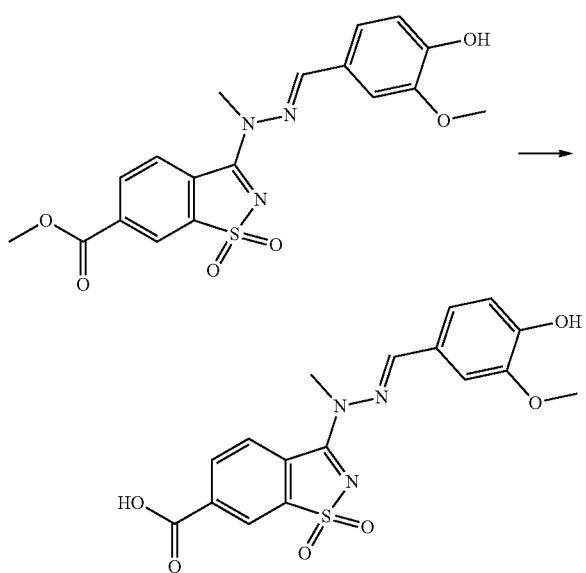

To a solution of methyl 3-[[(E)-(4-hydroxy-3-methoxy-phenyl)methyleneamino]-methyl-amino]-1,1-dioxo-1,2-benzothiazole-6-carboxylate (250.0 mg; 0.62 mmol; 1 eq.) in THF (7.5 mL), lithium hydroxide (29.7 mg; 1.24 mmol; 2 eq.) solubilized in water (5 mL) was added. The reaction mixture was stirred 5 h at rt. The reaction mixture was concentrated under vacuum and HCl 1N was added. The solid was filtered, dried under vacuum and triturated in acetonitrile. The solid was filtered to give 3-[[(E)-(4-hydroxy-3-methoxy-phenyl)methyleneamino]-methyl-amino]-1,1-dioxo-1,2-benzothiazole-6-carboxylic acid (145.6 mg; 59%) as yellow solid. $^1$H NMR (DMSO-d$_6$, 400 MHz): δ 13.9 (s broad, 1H); 9.79 (s, 1H); 9.00 (d, J=8.4 Hz, 1H); 8.43 (d, J=8 Hz, 1H); 8.40 (s, 1H); 8.36 (s, 1H); 7.43 (s, 1H); 7.36 (d, J=8 Hz, 1H); 6.95 (d, J=8 Hz, 1H); 3.90 (s, 3H); 3.79 (s, 3H). mp >260° C.

Example 35: 2-methoxy-4-[(E)-[(5-methoxy-1,1-dioxo-1,2-benzothiazol-3-yl)-methyl-hydrazono]methyl]phenol Step A: 1-(5-methoxy-1,1-dioxo-1,2-benzothiazol-3-yl)-1-methyl-hydrazine

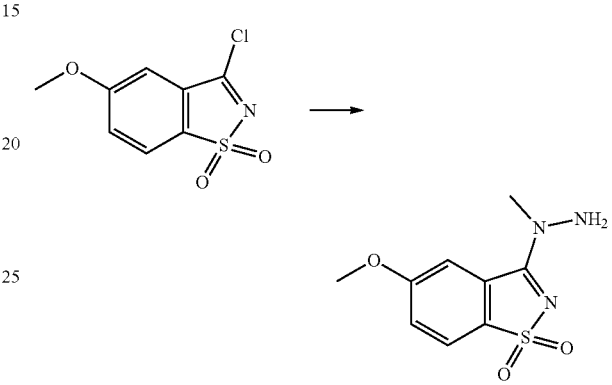

3-chloro-5-methoxy-1,2-benzothiazole 1,1-dioxide (example 11, step A, 200.0 mg; 0.86 mmol; 1. eq.) was dissolved into dry THF (1.2 mL) and then added dropwise to a solution of methyl hydrazine (51 µl; 0.95 mmol; 1.1 eq.) in THF (3 mL). The resulting mixture was stirred under reflux for 45 min. The precipitate was filtered and washed with water, with NaOH 1N, and again with water (until pH of filtrate was neutral). The solid was dried at 40° C. in an oven under vacuum to give 1-(5-methoxy-1,1-dioxo-1,2-benzothiazol-3-yl)-1-methyl-hydrazine (80.7 mg; 39%) as a white powder. $^1$H NMR (DMSO-d$_6$, 300 MHz): δ 8.52 (d, J=1.5 Hz, 1H); 7.84 (d, J=8.1 Hz, 1H); 7.32 (dd, J=1.5 Hz, J=8.1 Hz, 1H); 5.58 (s broad, 2H); 3.86 (s, 3H); 3.32 (s, 3H).

Step B: 2-methoxy-4-[(E)-[(5-methoxy-1,1-dioxo-1,2-benzothiazol-3-yl)-methyl-hydrazono]methyl]phenol

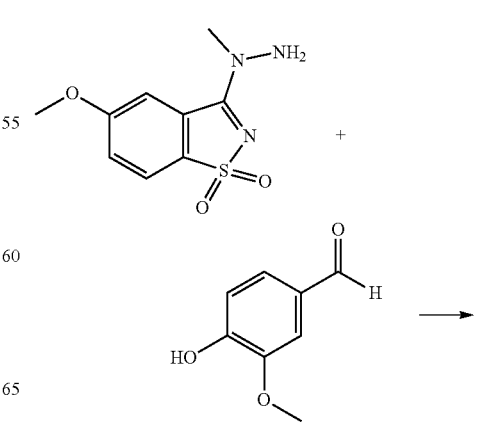

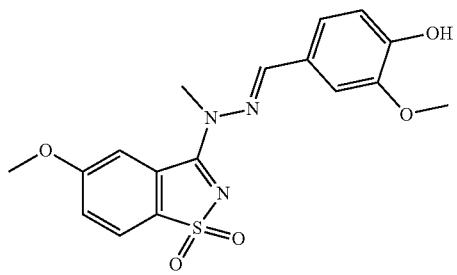

1-(5-methoxy-1,1-dioxo-1,2-benzothiazol-3-yl)-1-methyl-hydrazine (80.0 mg; 0.33 mmol; 1 eq.) and 4-hydroxy-3-methoxybenzaldehyde (55.5 mg; 0.36 mmol; 1.1 eq.) were suspended into 1,4-dioxane (1.20 mL) and were heated under reflux for 7 h. Dioxane was removed under vacuum. The residual solid was filtered and washed with EtOH to give 2-methoxy-4-[(E)-[(5-methoxy-1,1-dioxo-1,2-benzothiazol-3-yl)-methyl-hydrazono]methyl]phenol (92.2 mg; 73%) as a pale yellow powder. $^1$H NMR (DMSO-d$_6$, 400 MHz): δ 9.77 (s, 1H); 8.45 (d, J=2 Hz, 1H); 8.36 (s, 1H); 7.99 (d, J=8.4 Hz, 1H); 7.43 (d, J=1.6 Hz, 1H); 7.40 (dd, J=2 Hz, J=8.4 Hz, 1H); 7.30 (dd, J=2 Hz, J=8 Hz, 1H); 6.92 (d, J=8 Hz, 1H), 3.93 (s, 3H); 3.87 (s, 3H); 3.76 (s, 3H). mp: 299-300° C.

Example 36: 4-[(E)-[(1,1-dioxo-1,2-benzothiazol-3-yl)-isopropyl-hydrazono]methyl]-2-methoxy-phenol Step A: 4-[(E)-(isopropylhydrazono)methyl]-2-methoxy-phenol The compound was prepared using the same procedure detailed in example 1 step B starting from 4-hydroxy-3-methoxybenzaldehyde (100.0 mg; 0.66 mmol; 1 eq.) and isopropylhydrazine hydrochloride (80.0 mg; 0.72 mmol; 1.1 eq.) giving 4-[(E)-(isopropylhydrazono)methyl]-2-methoxy-phenol (125.1 mg, 91%) as an orange solid, used without further purification in the following step. $^1$H NMR (DMSO-d$_6$, 300 MHz): δ 11.49 (br s, 1H); 10.06 (s broad, 1H); 8.61 (s, 1H); 7.34 (d, J=1.8 Hz, 1H); 7.25 (dd, J=1.9 Hz, J=8.2 Hz, 1H); 6.92 (d, J=8.3 Hz, H); 3.82 (s, 3H); 3.60 (quin, J=6.0 Hz, 1H); 1.31 (d, J=6.4 Hz, 6H).

Step B: 4-[(E)-[(1,1-dioxo-1,2-benzothiazol-3-yl)-isopropyl-hydrazono]methyl]-2-methoxy-phenol

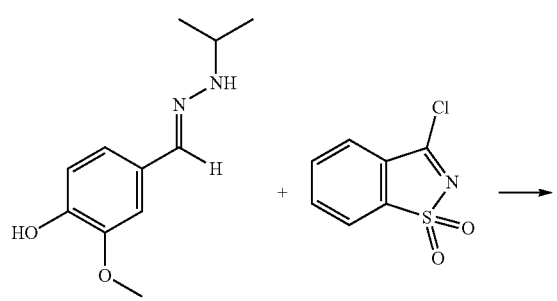

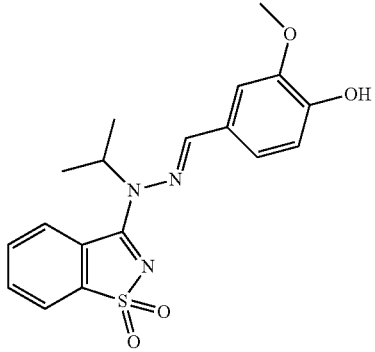

The compound was prepared using the same procedure detailed in example 1 step C starting from 4-[(E)-(isopropylhydrazono)methyl]-2-methoxy-phenol (120.0 mg; 0.58 mmol; 1.1 eq.) and 3-chloro-1,2-benzothiazole 1,1-dioxide (Example 1, step A, 105.6 mg; 0.52 mmol; 1 eq.) giving 4-[(E)-[(1,1-dioxo-1,2-benzothiazol-3-yl)-isopropyl-hydrazono]methyl]-2-methoxy-phenol (31.3 mg, 16%) as a pale yellow powder. $^1$H NMR (DMSO-de, 400 MHz): δ 8.62 (s, 1H); 8.30 (m, 1H); 8.03 (m, 1H); 7.80 (m, 2H); 7.50 (d, J=2.0 Hz, 1H); 7.38 (dd, J=1.9 Hz, J=8.3 Hz, 1H); 6.94 (d, J=8.1 Hz, 1H); 5.11 (quin, J=6.8 Hz, 1H); 3.87 (s, 3H); 1.50 (d, J=6.8 Hz, 6H). mp: 80-84° C.

Example 37: 4-[(E)-[(1,1-dioxo-1,2-benzothiazol-3-yl)-(2,2,2-trifluoroethyl)-hydrazono] methyl]-2-methoxy-phenol Step A: 2-methoxy-4-[(E)-(2,2,2-trifluoroethylhydrazono)methyl]phenol

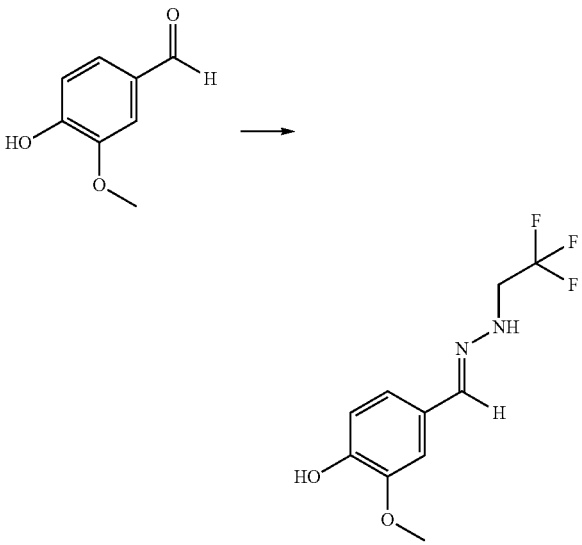

The compound was prepared using the same procedure detailed in example 1 step B starting from 4-hydroxy-3-methoxybenzaldehyde (200.0 mg; 1.31 mmol; 1 eq.) and 2,2,2,-trifluoroethylhydrazine (182 μL; 1.45 mmol; 1.1 eq.) giving 2-methoxy-4-[(E)-(2,2,2-trifluoroethylhydrazono)methyl]phenol (302.1 mg, 93%) as a grey solid, used without further purification in the following step. $^1$H NMR (CHLOROFORM-d, 300 MHz): δ 7.63 (s, 1H); 7.24 (s, 1H); 6.89 (m, 2H); 5.45 (t, J=5.9 Hz, 1H); 3.93 (s, 3H); 3.84 (dq, J=6.1 Hz, J=9.0 Hz, 2H).

Step B: 4-[(E)-[(1,1-dioxo-1,2-benzothiazol-3-yl)-(2,2,2-trifluoroethyl)hydrazono]methyl]-2-methoxyphenol

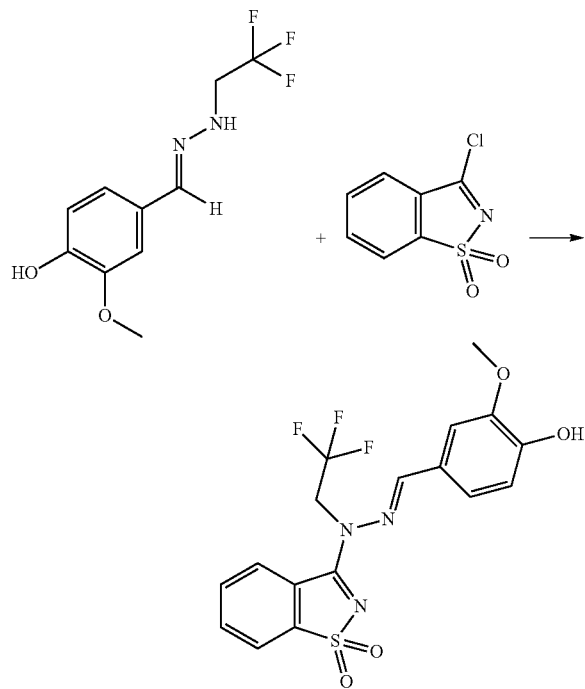

The compound was prepared using the same procedure detailed in example 1 step C starting from 2-methoxy-4-[(E)-(2,2,2-trifluoroethylhydrazono)methyl]phenol (302.0 mg; 1.22 mmol; 1.1 eq.) and 3-chloro-1,2-benzothiazole 1,1-dioxide (Example 1, step A, 223.0 mg; 1.11 mmol; 1 eq.) giving 4-[(E)-[(1,1-dioxo-1,2-benzothiazol-3-yl)-(2,2,2-trifluoroethyl)hydrazono]methyl]-2-methoxy-phenol (195.7 mg, 43%) as an orange powder. $^1$H NMR (DMSO-$d_6$, 400 MHz): δ 9.86 (s, 1H); 8.86 (m, 1H); 8.58 (s, 1H); 8.15 (m, 1H); 7.94 (m, 2H); 7.41 (d, J=1.8 Hz, 1H); 7.31 (dd, J=2.0 Hz, J=8.1 Hz, 1H); 6.96 (d, J=8.1 Hz, 1H); 5.40 (q, J=8.9 Hz, 2H); 3.89 (s, 3H). mp: 244-253° C.

Example 38: 4-[(1,1-dioxo-1,2-benzothiazol-3-yl)-[(E)-(4-hydroxy-3-methoxy-phenyl) methyleneamino]amino]benzoic acid Step A: 4-[(2E)-2-[(4-hydroxy-3-methoxy-phenyl)methylene]hydrazino]benzoic acid

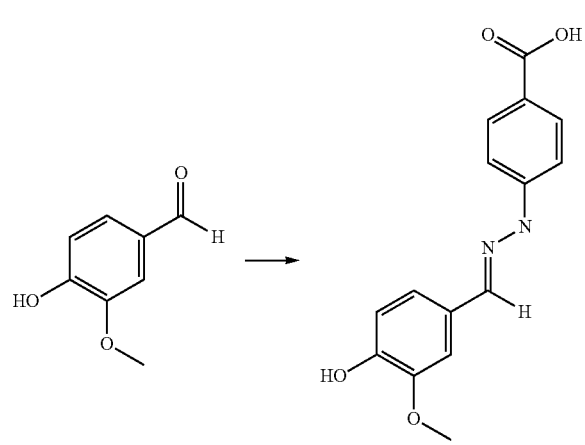 [SMILES: COc1cc(C=O)ccc1O ; COc1cc(/C=N/Nc2ccc(C(=O)O)cc2)ccc1O]

The compound was prepared using the same procedure detailed in example 1 step B starting from 4-hydroxy-3-methoxybenzaldehyde (150.0 mg; 0.99 mmol; 1 eq.) and 4-hydrazinobenzoic acid (165.0 mg; 1.08 mmol; 1.1 eq.) giving 4-[(2E)-2-[(4-hydroxy-3-methoxy-phenyl)methylene]hydrazino]benzoic acid (365.7 mg, quant.) as a brown solid, used without further purification in the following step. $^1$H NMR (DMSO-$d_6$, 300 MHz): δ 10.43 (s, 1H); 7.78 (m, 3H); 7.26 (d, J=1.7 Hz, 1H); 7.01 (m, 3H); 6.82 (d, J=8.1 Hz, 1H); 3.83 (s, 3H).

Step B: 4-[(1,1-dioxo-1,2-benzothiazol-3-yl)-[(E)-(4-hydroxy-3-methoxy-phenyl) methyleneamino]amino]benzoic acid

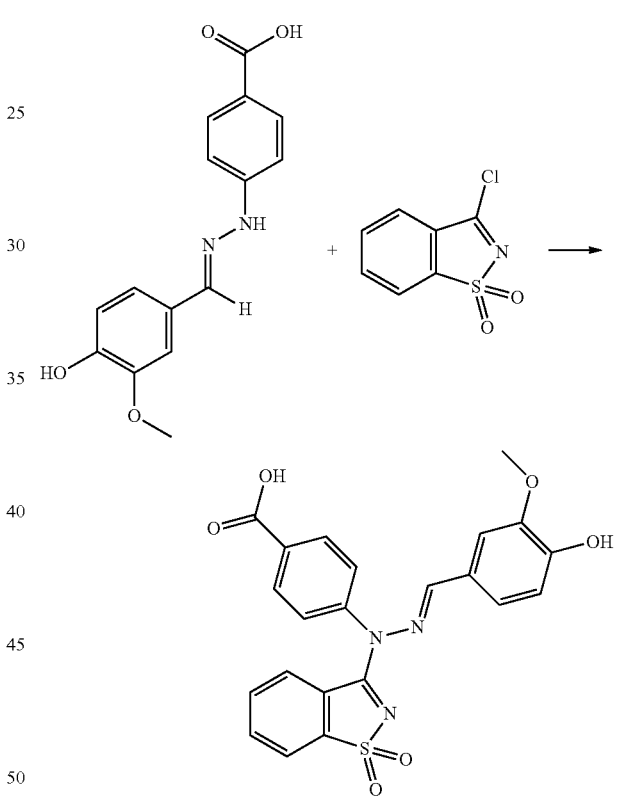

The compound was prepared using the same procedure detailed in example 1 step C starting from 2-methoxy-4-[(E)-(2,2,2-trifluoroethylhydrazono)methyl]phenol (283.0 mg; 0.99 mmol; 1.1 eq.) and 3-chloro-1,2-benzothiazole 1,1-dioxide (Example 1, step A, 181.2 mg; 0.90 mmol; 1 eq.) giving 4-[(1,1-dioxo-1,2-benzothiazol-3-yl)-[(E)-(4-hydroxy-3-methoxy-phenyl)methyleneamino]amino]benzoic acid (33.1 mg, 8%) as a beige powder. $^1$H NMR (DMSO-$d_6$, 400 MHz): δ 10.92 (s, 1H); 8.23 (m, 1H); 8.16 (m, 1H); 8.00 (m, 3H); 7.83 (d, J=8.8 Hz, 2H); 7.56 (d, J=1.8 Hz, 1H); 7.51 (d, J=8.1 Hz, 1H); 7.39 (dd, J=1.8 Hz, J=8.4 Hz, 1H); 7.15 (d, J=8.8 Hz, 2H); 3.89 (s, 3H). mp: 225-234° C.

Example 39: 4-[(E)-[(1,1-dioxo-6-phenyl-1,2-benzo-thiazol-3-yl)-methyl-hydrazono]-methyl]-2-methoxy-phenol Step A: 1,1-dioxo-6-phenyl-1,2-benzothiazol-3-one

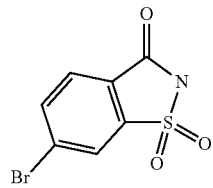 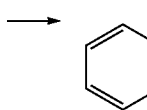

PdCl$_2$(dppf) (77.90 mg; 0.10 mmol; 0.05 eq.) and phenylboric acid (279.14 mg; 2.29 mmol; 1.20 eq.) were added to a solution of 6-bromo-1,1-dioxo-1,2-benzothiazol-3-one (500.00 mg; 1.91 mmol; 1.00 eq.) in ethylene glycol dimethyl ether (5.00 ml). A solution of K$_2$CO$_3$ (395.50 mg; 2.86 mmol; 1.50 eq.) in water (1.67 ml) was added and the reaction was stirred 10 minutes at 120° C. under microwave irradiation. The mixture was then filtered over Whatmann and the filtrate concentrated under reduced pressure. Water was added to the residue and the resulting aqueous phase was washed twice with EtOAc. Then, the aqueous phase was acidified with HCl 1N and extracted twice with EtOAc. Organic layers were combined, dried over MgSO$_4$, filtered and concentrated under reduced pressure to give 1,1-dioxo-6-phenyl-1,2-benzothiazol-3-one (409.0 mg; 83%) as an orange powder. $^1$H NMR (DMSO-d$_6$, 300 MHz): δ 8.25 (m, 2H); 8.19 (m, 1H); 7.83 (m, 2H); 7.52 (m, 3H).

Step B: 3-chloro-6-phenyl-1,2-benzothiazole 1,1-dioxide

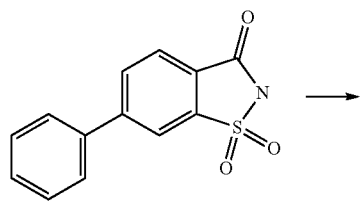

The compound was prepared using the same procedure detailed in example 1 step A starting from 1,1-dioxo-6-phenyl-1,2-benzothiazol-3-one (409.0 mg; 1.58 mmol; 1.00 eq.) to give 3-chloro-6-phenyl-1,2-benzothiazole 1,1-dioxide (437.0 mg; quantitatif) as a brown solid, used without further purification in the following step. $^1$H NMR (DMSO-d$_6$, 300 MHz): δ 8.21 (m, 1H); 7.88 (m, 2H); 7.51 (m, 3H); 7.21 (m, 2H).

Step C: 4-[(E)-[(1,1-dioxo-6-phenyl-1,2-benzothiazol-3-yl)-methyl-hydrazono]methyl]-2-methoxy-phenol

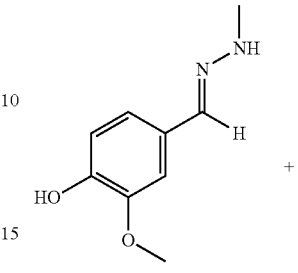

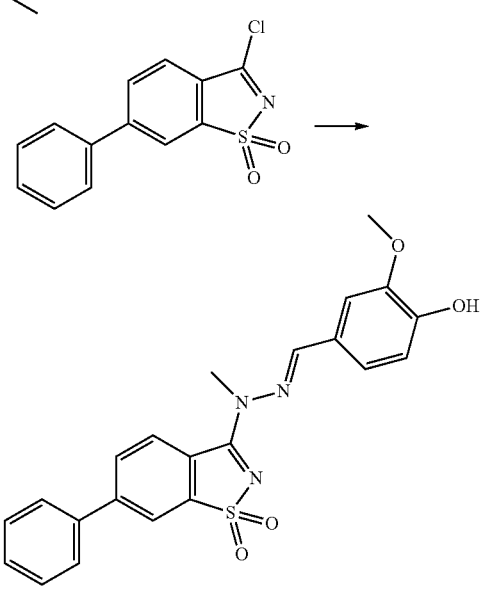

The compound was prepared using the same procedure detailed in example 1 step C starting from 3-chloro-6-phenyl-1,2-benzothiazole 1,1-dioxide (192.7 mg; 0.69 mmol; 1.00 eq.) and 2-methoxy-4-[(E)-(methylhydrazono)methyl]phenol (example 1, step B, 250.0 mg; 1.39 mmol; 2 eq.) giving 4-[(E)-[(1,1-dioxo-6-phenyl-1,2-benzothiazol-3-yl)-methyl-hydrazono]methyl]-2-methoxy-phenol (11.0 mg; 4%) as a yellow powder. $^1$H NMR (DMSO-d$_6$, 400 MHz): δ 9.74 (s broad, 1H); 9.13 (d, J=1.5 Hz, 1H); 8.40 (s, 1H); 8.15 (d, J=6.0 Hz, 1H); 8.08 (dd, J=1.5 Hz, J=6.0 Hz, 1H); 7.71 (m, 2H); 7.53 (m, 3H); 7.33 (dd, J=1.9 Hz, J=8.3 Hz, 1H); 7.30 (d, J=2.0 Hz, 1H); 6.90 (d, J=8.1 Hz, 1H); 3.81 (s, 3H), 3.46 (s, 3H).

Example 40: 2-methoxy-4-[(E)-[(6-methoxy-1,1-dioxo-1,2-benzothiazol-3-yl)-methyl hydrazono]methyl]phenol Step A: 3-chloro-6-methoxy-1,2-benzothiazole 1,1-dioxide

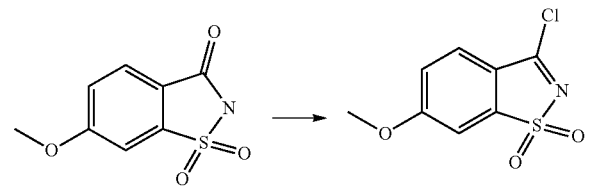

The compound was prepared using the same procedure detailed in example 1 step A starting from 6-methoxy-1,1-dioxo-1,2-benzothiazol-3-one (1.00 g; 4.69 mmol; 1.00 eq.) to give 3-chloro-6-methoxy-1,2-benzothiazole 1,1-dioxide dioxide (1.23 g; quantitatif) as an orange solid, used without further purification in the following step. ¹H NMR (DMSO-d₆, 300 MHz): δ 7.92 (d, J=8.6 Hz, 1H); 7.77 (d, J=2.1 Hz, 1H); 7.42 (dd, J=2.3 Hz, J=8.6 Hz, 1H); 3.95 (s, 3H).

Step B: 2-methoxy-4-[(E)-[(6-methoxy-1,1-dioxo-1,2-benzothiazol-3-yl)-methylhydrazono]methyl]phenol

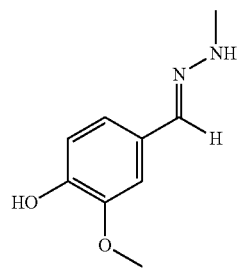
+
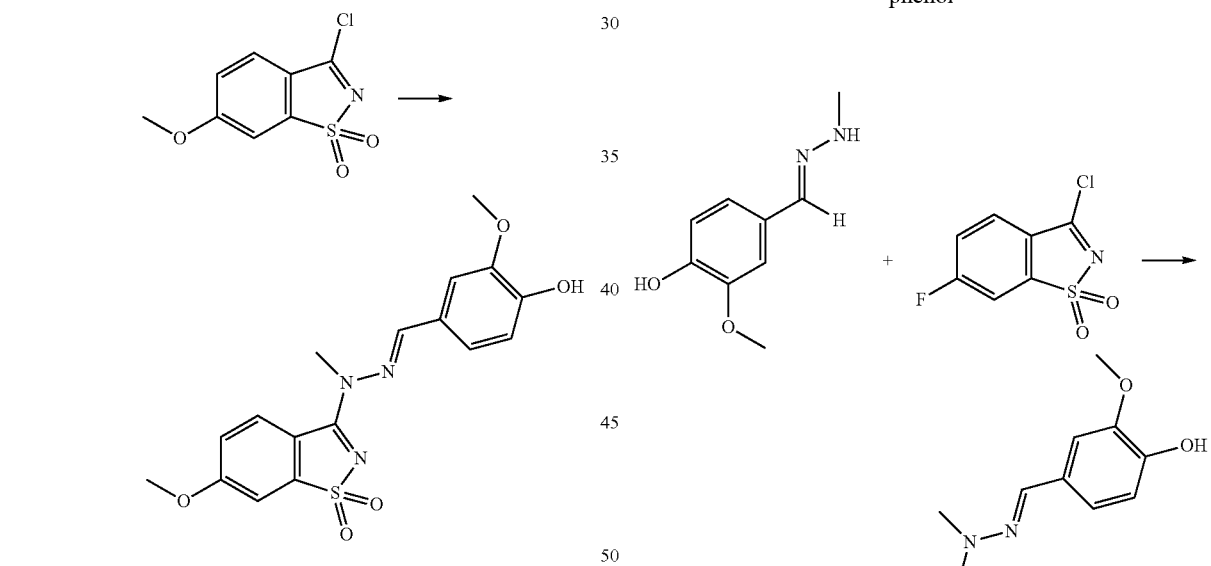

The compound was prepared using the same procedure detailed in example 1 step C starting from 3-chloro-6-methoxy-1,2-benzothiazole 1,1-dioxide (200.0 mg; 0.86 mmol; 1.00 eq.) and 2-methoxy-4-[(E)-(methylhydrazono)methyl]phenol (example 1, step B, 171.1 mg; 0.95 mmol; 1.10 eq.) giving 2-methoxy-4-[(E)-[(6-methoxy-1,1-dioxo-1,2-benzothiazol-3-yl)-methyl-hydrazono]methyl]phenol (37.6 mg; 11%) as a yellow powder. ¹H NMR (DMSO-d₆, 400 MHz): δ 9.74 (s, 1H); 8.77 (d, J=8.8 Hz, 1H); 8.34 (s, 1H); 7.64 (d, J=2.4 Hz, 1H); 7.43 (dd, J=2.5 Hz, J=8.9 Hz, 1H); 7.40 (d, J=2.0 Hz, 1H); 7.32 (dd, J=2.0 Hz, J=8.1 Hz, 1H); 6.94 (d, J=8.1 Hz, 1H); 3.96 (s, 3H); 3.88 (s, 3H); 3.74 (s, 3H).

Example 41: 4-[(E)-[(6-fluoro-1,1-dioxo-1,2-benzothiazol-3-yl)-methyl-hydrazono]-methyl]-2-methoxy-phenol Step A: 3-chloro-6-fluoro-1,2-benzothiazole 1,1-dioxide

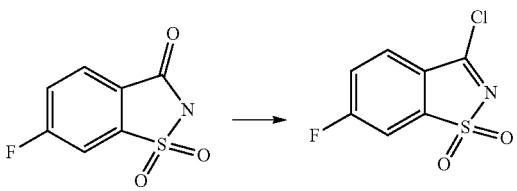 [SMILES: O=C1NS(=O)(=O)c2cc(F)ccc21 ; O=S1(=O)N=C(Cl)c2ccc(F)cc21]

The compound was prepared using the same procedure detailed in example 1 step A starting from 6-fluoro-1,1-dioxo-1,2-benzothiazol-3-one (500.0 mg; 2.37 mmol; 1.00 eq.) to give 3-chloro-6-fluoro-1,2-benzothiazole 1,1-dioxide dioxide (212.00 mg; 41%) as a pale brown solid. ¹H NMR (DMSO-d₆, 300 MHz): δ 8.25 (dd, J=2.2 Hz, J=7.3 Hz, 1H); 8.06 (dd, J=4.4 Hz, J=8.7 Hz, 1H); 7.78 (m, 1H).

Step B: 4-[(E)-[(6-fluoro-1,1-dioxo-1,2-benzothiazol-3-yl)-methyl-hydrazono]methyl]-2-methoxy-phenol

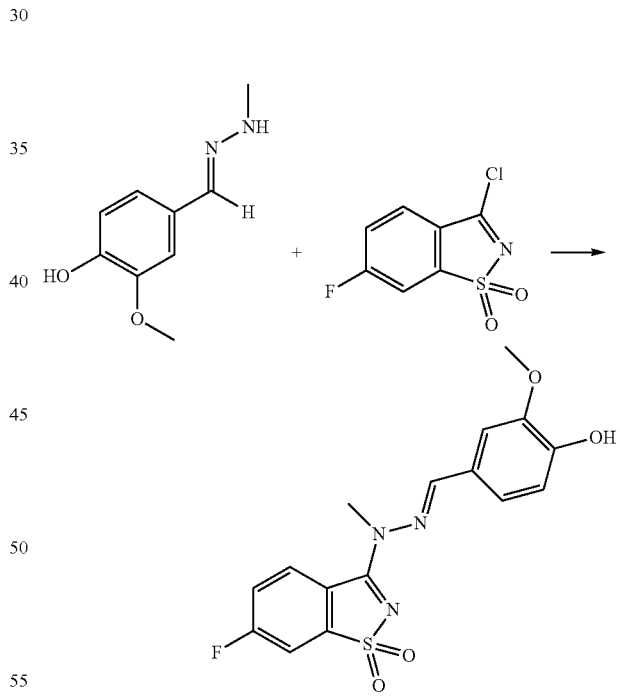

The compound was prepared using the same procedure detailed in example 1 step C starting from 3-chloro-6-fluoro-1,2-benzothiazole 1,1-dioxide (50.0 mg; 0.23 mmol; 1.00 eq.) and 2-methoxy-4-[(E)-(methylhydrazono)methyl]phenol (example 1, step B, 45.0 mg; 0.25 mmol; 1.10 eq.) giving 4-[(E)-[(6-fluoro-1,1-dioxo-1,2-benzothiazol-3-yl)-methyl-hydrazono]methyl]-2-methoxy-phenol (41.0 mg; 50%) as a yellow powder. ¹H NMR (DMSO-d₆, 300 MHz): δ 9.81 (brs, 1H); 8.92 (m, 1H); 8.37 (s, 1H); 8.14 (dd, J=6.8 Hz, J=2.3 Hz, 1H); 7.80 (m, 1H); 7.39 (d, J=1.5 Hz, 1H); 7.32

(dd, J=1.5 Hz, J=8.3 Hz, 1H); 6.92 (d, J=8.1 Hz, 1H); 3.88 (s, 3H); 3.77 (s, 3H). mp: 260-266° C.

Example 42: 4-[(E)-[(5-fluoro-1,1-dioxo-1,2-benzothiazol-3-yl)-methyl-hydrazono]-methyl]-2-methoxy-phenol Step A: 3-chloro-5-fluoro-1,2-benzothiazole 1,1-dioxide

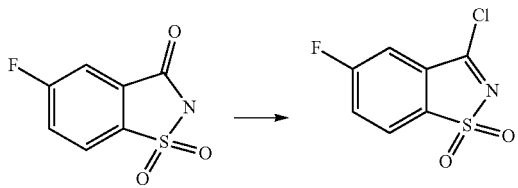 [SMILES: O=C1NS(=O)(=O)c2ccc(F)cc21 ; O=S1(=O)N=C(Cl)c2cc(F)ccc21]

The compound was prepared using the same procedure detailed in example 1 step A starting from 5-fluoro-1,1-dioxo-1,2-benzothiazol-3-one (500.0 mg; 2.37 mmol; 1.00 eq.) to give 3-chloro-5-fluoro-1,2-benzothiazole 1,1-dioxide dioxide (276.00 mg; 53%) as a brown solid. $^1$H NMR $^1$H NMR (DMSO-d$_6$, 300 MHz): δ 8.27 (m, 1H); 7.84 (m, 2H).

Step B: 4-[(E)-[(5-fluoro-1,1-dioxo-1,2-benzothiazol-3-yl)-methyl-hydrazono]methyl]-2-methoxy-phenol

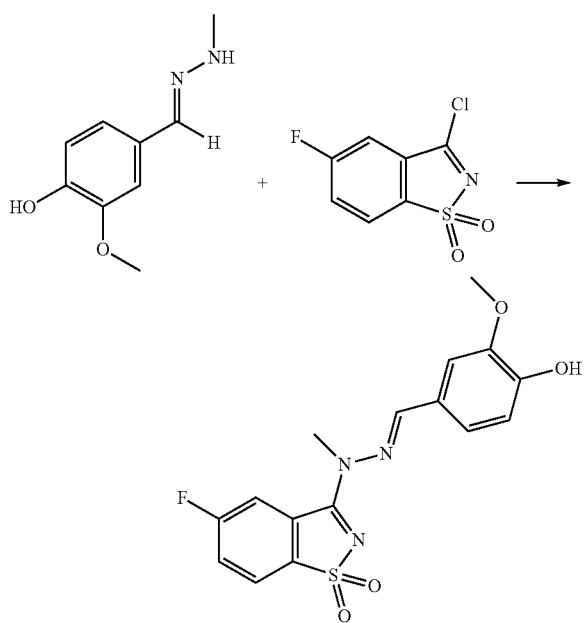

The compound was prepared using the same procedure detailed in example 1 step C starting from 3-chloro-5-fluoro-1,2-benzothiazole 1,1-dioxide (50.0 mg; 0.23 mmol; 1.00 eq.) and 2-methoxy-4-[(E)-(methylhydrazono)methyl]phenol (example 1, step B, 45.0 mg; 0.25 mmol; 1.10 eq.) giving 4-[(E)-[(5-fluoro-1,1-dioxo-1,2-benzothiazol-3-yl)-methyl-hydrazono]methyl]-2-methoxy-phenol (28.0 mg; 34%) as a yellow powder. $^1$H NMR $^1$H NMR (DMSO-d, 300 MHz): δ 9.83 (s, 1H); 8.65 (m, 1H); 8.38 (s, 1H); 8.17 (dd, J=5.3 Hz, J=8.2 Hz, 1H); 7.75 (m, 1H); 7.42 (d, J=1.7 Hz, 1H); 7.27 (dd, J=1.8 Hz, J=8.2 Hz, 1H); 6.93 (d, J=8.1 Hz, 1H); 3.89 (s, 3H); 3.77 (s, 3H). mp: 239-241° C.

Assays

YAP-TEAD AlphaLISA Assay for IC$_{50}$ Value Determination.

This assay demonstrates the ability of compounds of the invention to inhibit the YAP-TEAD interaction YAP-TEAD binding and inhibition was assessed by monitoring the engagement of YAP2 peptide (human YAP2-His6 (50-114) produced in *E. coli*) with TEAD (human TEAD1-GST (GST-TEAD1 (209-426) produced in *E. coli*) using the AlphaLisa technology (Perkin-Elmer). Specifically, in a 384 well (Axygen) 5 µl of compounds were dispensed in 100% DMSO following a semi log serial dilution, with a top concentration of 10$^m$M (10 concentrations). A '3 partners solution' was prepared by mixing AlphaScreen Glutathione Donor beads 15 µg/ml (PerkinElmer), Anti-6×His AlphaLisA Acceptor beads 15 µg/ml (PerkinElmer) and Human YAP2 9 nM in 100 mM NaCl, 25 mM Hepes, 0.1% BSA, 0.5% NoNidet®P40 buffer. In the 384 assay plate (Proxiplate, Perkin-Elmer)) 2 µl of compound at each concentration, 6 µl of buffer, 6 µl of hTEAD1-GST 9 nM and 6 µl of '3 partner solution' were mixed. After 2 h equilibration at room temperature in the dark the plates were read on an Envision instrument (Excitation @ 680 nm/Emission @ 570 nm, Perkin Elmer).

Results were expressed as % inhibition=100×((HighControl−Cpd)/(HighControl−LowControl)), were High control is the maximum response obtained with all components and Low control is the basal response obtained with all components without GST-Tead1.

Cpd is the response obtained for test compounds.

IC$_{50}$ (half maximal inhibitory concentration) was determined by fitting the concentration response curves using a 3-parameter curve fit equation and determining concentration corresponding to 50% inhibition.

The compounds of the present invention were tested for their capacity to inhibit YAP-TEAD interaction as described herein. The Examples were tested in the above assay and found to have IC$_{50}$ of about 0.083 µM to about 11.623 µM.

Results of YAP/TEAD AlphaLisa assay are given in Table 1.

TABLE 1

| IC$_{50}$ value determination in YAP-TEAD AlphaLISA assay | | |
|---|---|---|
| EX | IC$_{50}$ (µM) | Max Act. (%) |
| 1 | 0.886 | 92 |
| 2 | 0.949 | 93 |
| 3 | 5.003 | 88 |
| 4 | 0.615 | 97 |
| 5 | 5.498 | 88 |
| 6 | 7.036 | 95 |
| 7 | 4.582 | 94 |
| 8 | 1.100 | 94 |
| 9 | 11.623 | 96 |
| 10 | 4.996 | 92 |
| 11 | 0.475 | 94 |
| 12 | 0.583 | 95 |
| 13 | 2.122 | 95 |
| 14 | 1.626 | 90 |
| 15 | 2.890 | 89 |
| 16 | 0.095 | 86 |
| 17 | 0.150 | 90 |
| 18 | 0.084 | 97 |
| 19 | 0.626 | 92 |
| 20 | 3.411 | 95 |
| 21 | 0.123 | 89 |

TABLE 1-continued

IC$_{50}$ value determination in YAP-TEAD AlphaLISA assay

| EX | IC$_{50}$ (µM) | Max Act. (%) |
|---|---|---|
| 22 | 0.083 | 97 |
| 23 | 0.305 | 99 |
| 24 | 0.902 | 92 |
| 25 | 0.568 | 90 |
| 26 | 0.399 | 95 |
| 27 | 0.891 | 91 |
| 28 | 2.647 | 94 |
| 29 | 0.130 | 91 |
| 30 | 0.878 | 90 |
| 31 | 0.131 | 92 |
| 32 | 0.139 | 95 |
| 33 | 0.766 | 90 |
| 34 | 4.569 | 97 |
| 35 | 0.354 | 77 |
| 36 | 77.960 | 77 |
| 37 | 70.750 | 74 |
| 38 | 105.020 | 99 |
| 39 | 62.210 | 61 |
| 40 | 16.250 | 91 |
| 41 | 5.740 | 85 |
| 42 | 2.470 | 84 |

Effect of Compounds on the Cell-Based TEAD-GAL4 Transactivation Assay

To identify inhibitors of YAP-TEAD interaction, a transient transactivation assays was carried out into HEK293 cell line (HEK293 GripTite™ 293 MSR (Invitrogen R795-07)) using plasmids containing the full length TEAD1 sequences, the full length YAP mutant (S127A, S397A) and a luciferase gene reporter. All expression constructs were performed into pSG5 backbone plasmid in which the SV40 promoter was replaced by the CMV promoter. The TEAD1 construct was prepared by cloning the full length human TEAD1 cDNA in fusion with the Gal4 DNA Binding Domain (AA 1-148) into pSG5_CMV to create the TEAD1 (FL)_hum_pSG5Gal4_CMV. The full length YAP mutant (S127A, S397A) was also cloned into pSG5_CMV to create the YAP(FL)_hum_pSG5_mutS127A_S397A_CMV. The reporter plasmid GAL4(5×RE)_TK(−105/+56)_pGL3-Basic contains 5 copies of the GAL4 responsive element (5'-TCGGAGGACAGTACTCC-3') upstream of the thymidine kinase (TK) promoter (−105/+56) inserted in a pGL3-Basic vector. To evaluate the selectivity of our compounds in blocking the YAP-TEAD interaction, a counter-screening protein-protein interaction transactivation assays was also established. Briefly, two other expression plasmids, the pBD-P53 which express the P53 (AA 72-390) in fusion with Gal4 and the pAD-SV40T which express the SV40 large T antigen (AA 84-708,AgT), were created. HEK293 cells were seeded at 5×10$^4$ cells/well in 96 well plates (assay plates) in DMEM medium containing 4.5 g/L D-glucose, 10% high inactivated (HI) fetal bovine serum 1% Glutamax, 1% non-essential amino acid and 1% sodium pyruvate and 0.5% penicillin/streptomycin 37° C. in a humidified atmosphere of 8% CO2. After 24 h, transfections are performed using Jet-PEI as transfectant (101B-010 Polyplus Transfection), according to the instructions of the manufacturer (N/P=10) and a ratio YAP/TEAD=10 (per well: 50 ng of YAP(FL), 5 ng of TEAD(FL) and 50 ng of reporter plasmid). Six hours after cell transfection, the plates ('assay plate') were washed with 100 µl PBS per well and cell were treated with compounds in semi-log from 0.1 µM to 30 µM or DMSO 0.5% as control in DMEM 4.5 g/L D-Glucose without phenol red, 0.3% BSA, 1% glutamax, 1% NEAA, 1% sodium pyruvate. Twenty-four hours later, the luciferase activity was determined after addition of 100 µl of Steady Glo™ luciferase assay system (Promega E2550) according to the manufacturer's directions. Luciferase activity in cell extracts is measured by reading luminescence using the Envision device.

The cellular response was determined by fitting the concentration response curves using a 3-parameter curve fit equation and determining the concentration that inhibited the luciferase activity by 50%.

Compounds tested (Ex1, 2, 7—FIG. 1) inhibit the luciferase activity between 50% and 75% at 30 µM, under conditions where no inhibitory effect was observed in the in the counter screening assay (P53+AgT).

Inhibition of Malignant Mesothelioma Tumor Cell Growth

Figure 2:
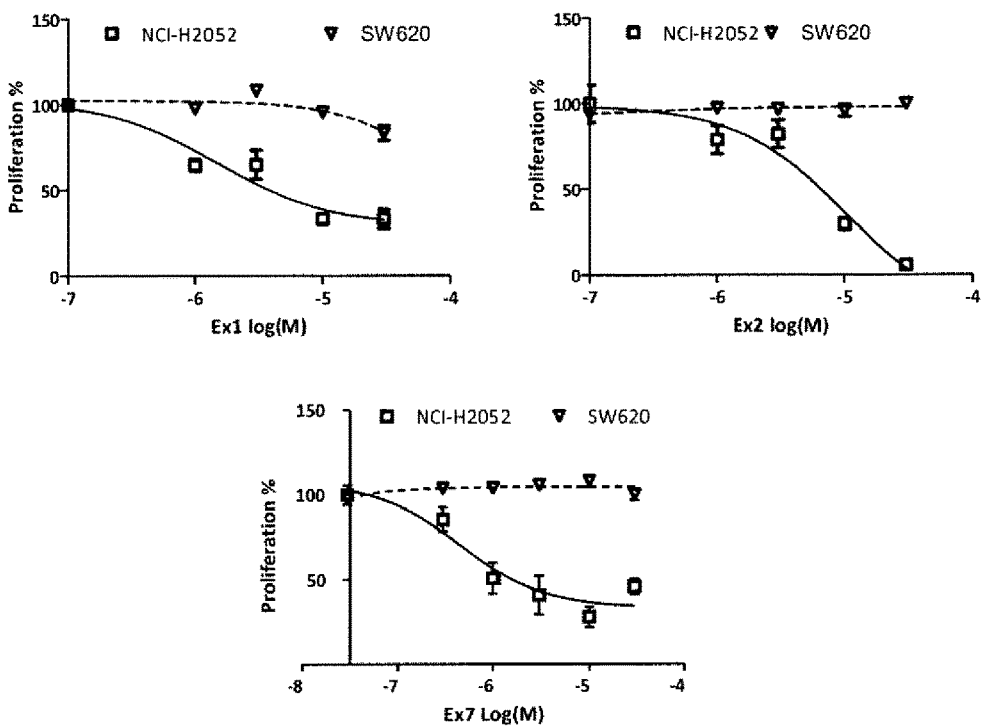
FIG. 2 represents the anti-proliferative activity of compounds of examples 1, 2 and 7 as compounds representatives of the inhibitor of the YAP/TAZ-TEAD interaction of the invention in mesothelioma cells NCI-H2052

The tumor cell growth inhibitory activity of the YAP-TEAD interaction inhibitors was evaluated in NCI-H2052 mesothelioma cell line harboring a NF2 mutation. This cell line was selected based on its mutational status and the ability of a siRNA directed against YAP, TAZ or TEAD1-4 to inhibit cell proliferation. The nuclear localization of YAP at confluence was also taken into account. Based on these observations we were able to classify several "YAP dependent cells" where YAP is clearly nuclear and in which a cell growth inhibition is observed by using siRNA (NCI-H2052, SKOV-3, ACHN, A549) and the "YAP independent cells" where YAP is preferentially located in the cytoplasm and in which no inhibition of cell growth is observed by using a siRNA (SW620, Met-5a). 10000 cells/well were plated in a 96-well black plate with clear flat bottom TC-Treated Imaging plate (Falcon #353219) in regular medium (as suggested from ATCC for each cell line) with serum, which was replaced the day after with starvation medium containing 1% serum. After one day growth in the starvation medium, cells were incubated with compounds. The starting concentration was 30 µM and serial dilutions in DMSO and medium were performed until 0.11p M to achieve a final DMSO concentration of 0.5%. The cells were then allowed to grow for 3 days, and then, EdU (Invitrogen, Molecular Probe) was added in each well at a final concentration of 10 µM and the cells were returned to the incubator for additional 24 h. Starvation medium was removed and 100 µl of PFA 4% containing Hoechst dye was adding in each well to fix the cells. Plates were then incubated at room temperature for 15 minutes, washed twice with PBS and the cells were permeabilized by adding 100 µl per well of triton-100 containing 0.3% BSA. After 20 minutes cells were washed with PBS and the EdU detection was performed according to the instructions of the manufacturer. Image acquisition was performed using the ImageXpress Micro and analysed using the MetaXpress software (Molecular Device). Results were expressed as a percent of inhibition (%) of the cell proliferation values obtained with 0.5% DMSO treatment alone. The cellular response was determined by fitting the concentration response curves using a 3 parameter curve fit equation and determining the concentration that inhibited cell growth between 50% and 100%. Compounds (Ex 1, 2, 7) inhibited NCI-H2052 mesothelioma cell proliferation (NF2 mutated cell line; FIG. 2) without showing any effect in the SW620 cell line, a "YAP-independent cell line", FIG. 2. In addition ours compounds inhibited SKOV-3, A549 and ACHN cell growth without affecting proliferation of the "YAP independent" cell line, Met-5a (data not shown).

Comparative Example

The same experiments were conducted with N-[(E)-(3,4-dimethoxyphenyl) methylene amino]-N-methyl-1,1-dioxo- 1,2-benzothiazol-3-amine (compound 40 of WO 2004/087153). This compound is the same as example 1 of the present invention, except that the methoxyphenol moiety is replaced with a dimethoxyphenyl moiety.

The dimethoxyphenyl compound of the prior art showed 30% inhibition at 1 mM concentration. Compared to the 92% inhibition at 0.886 μM for compound of example 1, this shows that the compounds of the prior art are not inhibitors of the YAPITAZ-TEAD interaction.

REFERENCES

Avruch et al., Cell Cycle 2012, 1090-1096
Badouel et al., Curr Opin Cell Biol 2009, 21, 837-43
Bianchi et al., Nat Genet 1994, 6, 185-192
Bianchi et al. Natl Acad. Sci. USA, 1995, 92, 10854-10858
Blanchet et al. Journal of Organic Chemistry, 72(9), 3199-3206; 2007
Bott et al., Nat Genet 2011, 43, 668-672
Carbone et al., Clin Cancer Res 2012, 18, 598-604
Chad et al., Cancer Res 2010, 70, 8517-25
Challenger et al. PCT Int. Appl., 9920323; 29 Apr. 1999
Courtin et al. Helvetica Chimica Acat, 66(1), 68-75; 1983
De Christofaro T, Eur J Cancer 2011, 926-933
Deguen et al., Int J Cancer 1998, 77, 554-560
Differding et al. Helvetica Chimica Acta, 72(6), 1248-52; 1989
Dong et al. Cell, 2007, 130: 1120-1133
Forbe et al., Nucleic Acids Res 2011, 39, D945-950
Gray et al. Tetrahedron Letters, 41(32), 6237-6240; 2000
Haffner et al. Bioorganic & Medicinal Chemistry Letters, 20(23), 6989-6992; 2010
Haffner et al. Bioorganic & Medicinal Chemistry Letters, 20(23), 6983-6988; 2010
Harvey et al., Nat Rev Cancer, 2013, 13, 246-257
Hong W et al., Cell Dev Biol 2012, 23, 785-793
Huang et al., Cell 2005, 122, 421-34
Kurian et al. Bioorganic & Medicinal Chemistry Letters, 24(17), 4176-4180; 2014
Lei et al., Mol Cell Biol 2008, 28, 2426-36)
Loghmani-Khouzani et al. Journal of Chemical Research, Synopses, (2), 80-81; 2001
Murakami et al., Cancer Res 2011, 71, 873-883
Park et al., Environ Health Perspect 2011, 119, 514-518
Perez-Serrano et al. Organic Letters, 1(8), 1183-1186; 1999
Ranjit et al. Journal of Organic Chemistry, 59(23), 7161-7163; 1994
Raw et al. Tetrahedron Letters, 52(50), 6775-6778; 2011
Ruttledge et al., Nat Genet 1994, 6, 180-184
Schneider et al. Organic Letters, 13(14), 3588-3591; 2011
Sekido et al., Cancer Res 1995, 55, 1227
Sekido et al., Pathol Int 2011, 61, 331-344
Steinhardt et al., Hum. Pathol 2008, 39, 1582-9
Thea et al. Journal of Organic Chemistry, 50(12), 2158-2165; 1985
Tumaneng K et al., Curr Biol, 2013, 22, R368-379
Wang L et al., Tumour Biol 2014, 14, 463-468
Wang et al., Cancer Sci 2010, 101, 1279-85
Yokoyama et al., Carcinogenesis 2008, 29, 2139-2146
Yu Fx et al., Genes Dev 2013, 27, 355-371
Zeng et al., Cancer Cell 2008, 13, 188-192
Zhao et al, Cancer Res 2009, 69, 1089-98
Zhao et al., Gens Dev 2008, 22, 1962-71
Zhao et al. Genes Dev 2007, 21: 2747-2761
Zhou et al., Oncogene 2011, 30, 2181-86

The invention claimed is:
1. A compound of formula (I)

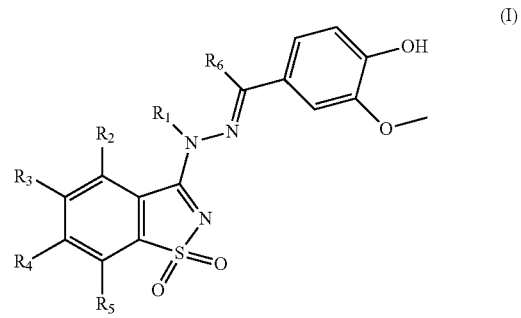

or a pharmaceutically acceptable salt thereof, wherein:
$R_1$ is alkyl or alkyl-$R_7$ or -aryl-$R_7$;
$R_2$, $R_3$, $R_4$, $R_5$ are independently H, halo, —B(O—$R_{11}$)$_2$, alkyl, alkoxyl, hydroxycarbonyl, —COO$R_{11}$, —CO—N$R_8R_9$ or aryl;
$R_6$ is H or alkyl; or
$R_1$ and $R_6$ are bound together to form a 5 or 6-member heterocycle;
$R_7$ is hydroxyl, alkylhydroxyl, —N$R_8R_9$, —CO—X—$R_{10}$, —CF$_3$, aryl;
$R_8$ and $R_9$ are independently H, alkyl or form together with the nitrogen atom a 3 to 6-member cyclic group;
X is —O— or —N$R_{11}$—;
$R_{10}$ is H, alkyl or hydroxyalkyl;
$R_{11}$ is H or alkyl.

2. A compound of formula:

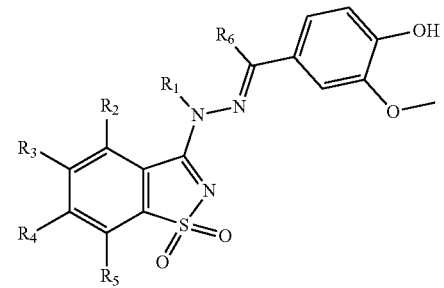

or a pharmaceutically acceptable salt thereof, wherein:
$R_1$ is H, alkyl or alkyl-$R_7$ or -aryl-$R_7$;
$R_2$, $R_4$, $R_5$ are independently H, halo, —B(O—$R_{11}$)$_2$, alkyl, alkoxyl, hydroxycarbonyl, —COO$R_{11}$, —CO—N$R_8R_9$ or aryl;
$R_3$ is halo, alkyl, alkoxyl, or hydroxycarbonyl;
$R_6$ is H or alkyl; or
$R_1$ and $R_6$ are bound together to form a 5 or 6-member heterocycle;
$R_7$ is hydroxyl, alkylhydroxyl, —N$R_8R_9$, —CO—X—$R_{10}$, —CN, —CF$_3$, aryl;
$R_8$ and $R_9$ are independently H, alkyl or form together with the nitrogen atom a 3 to 6-member cyclic group;
X is —O— or —N$R_{11}$—;
$R_{10}$ is H, alkyl or hydroxyalkyl;
$R_{11}$ is H or alkyl.

3. A compound of formula:

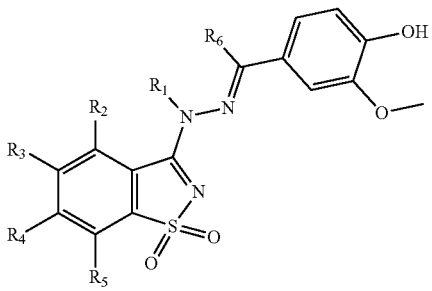

or a pharmaceutically acceptable salt thereof, wherein:
$R_1$ is H, alkyl or alkyl-$R_7$ or -aryl-$R_7$;
$R_2$, $R_3$, $R_4$, are independently H, halo, —B(O—$R_{11}$)$_2$, alkyl, alkoxyl, hydroxycarbonyl, —COOR$_{11}$, —CO—NR$_8$R$_9$ or aryl;
$R_5$ is halo, alkyl, alkoxyl, or hydroxycarbonyl;
$R_6$ is H or alkyl; or
$R_1$ and $R_6$ are bound together to form a 5 or 6-member heterocycle;
$R_7$ is hydroxyl, alkylhydroxyl, —NR$_8$R$_9$, —CO—X—R$_{10}$, —CN, —CF$_3$, aryl;
$R_8$ and $R_9$ are independently H, alkyl or form together with the nitrogen atom a 3 to 6-member cyclic group;
X is —O— or —NR$_{11}$—;
$R_{10}$ is H, alkyl or hydroxyalkyl;
$R_{11}$ is H or alkyl.

4. A compound of formula:

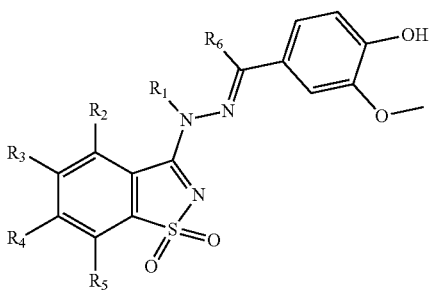

or a pharmaceutically acceptable salt thereof, wherein:
$R_1$ is H, alkyl or alkyl-$R_7$ or -aryl-$R_7$;
$R_2$, $R_3$, $R_5$ are independently H, halo, —B(O—$R_{11}$)$_2$, alkyl, alkoxyl, hydroxycarbonyl, —COOR$_1$, —CO—NR$_8$R$_9$ or aryl;
$R_4$ is halo, alkyl, alkoxyl, or hydroxycarbonyl;
$R_6$ is H or alkyl; or
$R_1$ and $R_6$ are bound together to form a 5 or 6-member heterocycle;
$R_7$ is hydroxyl, alkylhydroxyl, —NR$_8$R$_9$, —CO—X—R$_{10}$, —CN, —CF$_3$, aryl;
$R_8$ and $R_9$ are independently H, alkyl or form together with the nitrogen atom a 3 to 6-member cyclic group;
X is —O— or —NR$_{11}$—;
$R_{10}$ is H, alkyl or hydroxyalkyl;
$R_{11}$ is H or alkyl.

5. The compound of claim 1, which is selected from the group consisting of:
4-[(E)-[(1,1-dioxo-1,2-benzothiazol-3-yl)-methyl-hydrazono]methyl]-2-methoxy-phenol
4-[(E)-[(1,1-dioxo-1,2-benzothiazol-3-yl)-(2-hydroxyethyl)hydrazono]methyl]-2-methoxy-phenol
4-[(E)-[(1,1-dioxo-1,2-benzothiazol-3-yl)-ethyl-hydrazono]methyl]-2-methoxy-phenol
4-[(E)-[(1,1-dioxo-1,2-benzothiazol-3-yl)-(2-morpholinoethyl)hydrazono]methyl]-2-methoxy-phenol hydrochloride
4-[(E)-[(1,1-dioxo-1,2-benzothiazol-3-yl)-(3-hydroxypropyl)hydrazono]methyl]-2-methoxy-phenol
4-[(E)-[3-(dimethylamino)propyl-(1,1-dioxo-1,2-benzothiazol-3-yl)hydrazono]methyl]-2-methoxy-phenol hydrochloride
4-[(E)-[(1,1-dioxo-1,2-benzothiazol-3-yl)-(2-methoxyethyl)hydrazono]methyl]-2-methoxy-phenol
3-[(1,1-dioxo-1,2-benzothiazol-3-yl)-[(E)-(4-hydroxy-3-methoxy-phenyl)methylene amino]amino]propanoic acid
2-[(1,1-dioxo-1,2-benzothiazol-3-yl)-[(E)-(4-hydroxy-3-methoxy-phenyl)methylene amino]amino]-N-(2-hydroxyethyl)acetamide
4-[(E)-[(1,1-dioxo-1,2-benzothiazol-3-yl)-(3-methoxypropyl)hydrazono]methyl]-2-methoxy-phenol
4-[(E)-[(1,1-dioxo-1,2-benzothiazol-3-yl)-isopropyl-hydrazono]methyl]-2-methoxy-phenol
4-[(E)-[(1,1-dioxo-1,2-benzothiazol-3-yl)-(2,2,2-trifluoroethyl)hydrazono]methyl]-2-methoxy-phenol
4-[(1,1-dioxo-1,2-benzothiazol-3-yl)-[(E)-(4-hydroxy-3-methoxy-phenyl) methyleneamino]amino]benzoic acid
and pharmaceutically acceptable salts thereof.

6. The compound of claim 2, which is selected from the group consisting of:
4-[(E)-[2-hydroxyethyl-(5-methoxy-1,1-dioxo-1,2-benzothiazol-3-yl)hydrazono]methyl]-2-methoxy-phenol
2-methoxy-4-[(E)-[(5-methoxy-1,1-dioxo-1,2-benzothiazol-3-yl)-(2-morpholinoethyl) hydrazono]methyl] phenol
2-methoxy-4-[(E)-[(5-methoxy-1,1-dioxo-1,2-benzothiazol-3-yl)-(3-morpholino propyl)hydrazono]methyl] phenol hydrochloride
4-[(E)-[3-hydroxypropyl-(5-methoxy-1,1-dioxo-1,2-benzothiazol-3-yl)hydrazono]methyl]-2-methoxy-phenol
2-methoxy-4-[(E)-[(5-methoxy-1,1-dioxo-1,2-benzothiazol-3-yl)-(2-methoxyethyl) hydrazono]methyl]phenol
2-methoxy-4-[(E)-[methyl-(5-methyl-1,1-dioxo-1,2-benzothiazol-3-yl)hydrazono]methyl]phenol
2-methoxy-4-[(E)-[(5-methyl-1,1-dioxo-1,2-benzothiazol-3-yl)-(2-morpholinoethyl) hydrazono]methyl] phenol hydrochloride
4-[(E)-[2-hydroxyethyl-(5-methyl-1,1-dioxo-1,2-benzothiazol-3-yl)hydrazono]methyl]-2-methoxy-phenol
2-methoxy-4-[(E)-[2-methoxyethyl-(5-methyl-1,1-dioxo-1,2-benzothiazol-3-yl) hydrazono]methyl]phenol
2-methoxy-4-[(E)-[(5-methoxy-1,1-dioxo-1,2-benzothiazol-3-yl)-methyl-hydrazono]methyl]phenol
4-[(E)-[(5-fluoro-1,1-dioxo-1,2-benzothiazol-3-yl)-methyl-hydrazono]methyl]-2-methoxy-phenol
and pharmaceutically acceptable salts thereof.

7. The compound of claim 3, which is selected from the group consisting of:
4-[(E)-[(5,7-dimethoxy-1,1-dioxo-1,2-benzothiazol-3-yl)-methyl-hydrazono]methyl]-2-methoxy-phenol
4-[(E)-[(5,7-dimethoxy-1,1-dioxo-1,2-benzothiazol-3-yl)-(2-hydroxyethyl)hydrazono]methyl]-2-methoxy-phenol
4-[(E)-[(5,7-dimethoxy-1,1-dioxo-1,2-benzothiazol-3-yl)-(2-morpholinoethyl) hydrazono]methyl]-2-methoxy-phenol hydrochloride 4-[(E)-[(5,7-dimethoxy-1,1-dioxo-1,2-benzothiazol-3-yl)-(2-methoxyethyl)hydrazono]methyl]-2-methoxy-phenol 4-[(E)-[(5-fluoro-7-methyl-1,1-dioxo-1,2-benzothiazol-3-yl)-methyl-hydrazono]methyl]-2-methoxy-phenol 2-methoxy-4-[(E)-[(7-methoxy-1,1-dioxo-1,2-benzothiazol-3-yl)-methyl-hydrazono]methyl]phenol 4-[(E)-[2-hydroxyethyl-(7-methoxy-1,1-dioxo-1,2-benzothiazol-3-yl)hydrazono]methyl]-2-methoxy-phenol 2-methoxy-4-[(E)-[(7-methoxy-1,1-dioxo-1,2-benzothiazol-3-yl)-(2-morpholinoethyl) hydrazono]methyl]phenol hydrochloride 2-methoxy-4-[(E)-[(7-methoxy-1,1-dioxo-1,2-benzothiazol-3-yl)-(2-methoxyethyl) hydrazono]methyl]phenol 4-[(E)-[2-hydroxyethyl-(7-methoxy-5-methyl-1,1-dioxo-1,2-benzothiazol-3-yl) hydrazono]methyl]-2-methoxy-phenol 2-methoxy-4-[(E)-[2-methoxyethyl-(7-methoxy-5-methyl-1,1-dioxo-1,2-benzothiazol-3-yl)hydrazono]methyl]phenol 2-methoxy-4-[(E)-[(7-methoxy-5-methyl-1,1-dioxo-1,2-benzothiazol-3-yl)-methyl-hydrazono]methyl]phenol 2-methoxy-4-[(E)-[(7-methoxy-5-methyl-1,1-dioxo-1,2-benzothiazol-3-yl)-(2-morpholinoethyl)hydrazono]methyl]phenol hydrochloride and pharmaceutically acceptable salts thereof.

8. The compound of claim 4, which is selected from the group consisting of:

2-methoxy-4-[(E)-[methyl-(6-methyl-1,1-dioxo-1,2-benzothiazol-3-yl)hydrazono]methyl]phenol 3-[[(E)-(4-hydroxy-3-methoxy-phenyl)methyleneamino]-methyl-amino]-1,1-dioxo-1,2-benzothiazole-6-carboxylic acid 2-methoxy-4-[(E)-[(6-methoxy-1,1-dioxo-1,2-benzothiazol-3-yl)-methyl hydrazono]methyl]phenol 4-[(E)-[(6-fluoro-1,1-dioxo-1,2-benzothiazol-3-yl)-methyl-hydrazono]methyl]-2-methoxy-phenol and pharmaceutically acceptable salts thereof.

9. A pharmaceutical composition comprising a compound of claim 1 or one of its pharmaceutically acceptable salts and at least one pharmaceutically acceptable vehicle.

10. A method of treatment of malignant mesothelioma, which comprises administering a compound of claim 1 or a pharmaceutically acceptable salt thereof to a patient in need thereof.

11. A method of treatment of tumor cells where YAP is localized in the nucleus of said cells, which comprises administering a compound of claim 1 or a pharmaceutically acceptable salt thereof to a patient in need thereof.

12. The method of claim 11, wherein the tumor is lung, thyroid, ovarian, colorectal, prostate, pancreas, esophagus, liver, breast or skin tumor.

13. A pharmaceutical composition comprising a compound of claim 2 or one of its pharmaceutically acceptable salts and at least one pharmaceutically acceptable vehicle.

14. A pharmaceutical composition comprising a compound of claim 3 or one of its pharmaceutically acceptable salts and at least one pharmaceutically acceptable vehicle.

15. A pharmaceutical composition comprising a compound of claim 4 or one of its pharmaceutically acceptable salts and at least one pharmaceutically acceptable vehicle.

16. A method of treatment of malignant mesothelioma, which comprises administering a compound of claim 2 or a pharmaceutically acceptable salt thereof to a patient in need thereof.

17. A method of treatment of malignant mesothelioma, which comprises administering a compound of claim 3 or a pharmaceutically acceptable salt thereof to a patient in need thereof.

18. A method of treatment of malignant mesothelioma, which comprises administering a compound of claim 4 or a pharmaceutically acceptable salt thereof to a patient in need thereof.

* * * * *